(12) United States Patent
Osorio

(10) Patent No.: US 12,082,939 B2
(45) Date of Patent: *Sep. 10, 2024

(54) CONTINGENT CARDIO-PROTECTION FOR EPILEPSY PATIENTS

(71) Applicant: Flint Hills Scientific, L.L.C., Lawrence, KS (US)

(72) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/831,753

(22) Filed: Jun. 3, 2022

(65) Prior Publication Data

US 2022/0304616 A1 Sep. 29, 2022

Related U.S. Application Data

(60) Continuation of application No. 16/777,930, filed on Jan. 31, 2020, now Pat. No. 11,350,871, which is a
(Continued)

(51) Int. Cl.
*A61N 1/36* (2006.01)
*A61B 5/00* (2006.01)
(Continued)

(52) U.S. Cl.
CPC ........ *A61B 5/4094* (2013.01); *A61B 5/02405* (2013.01); *A61B 5/0245* (2013.01); *A61B 5/316* (2021.01); *A61B 5/349* (2021.01); *A61B 5/35* (2021.01); *A61B 5/352* (2021.01); *A61B 5/364* (2021.01); *A61B 5/7246* (2013.01); *A61B 5/7275* (2013.01); *A61N 1/36053* (2013.01); *A61N 1/36064* (2013.01)

(58) Field of Classification Search
CPC . A61B 5/04012; A61B 5/4094; A61B 5/7264; A61B 5/0402; A61B 5/0006; A61B 5/0205; A61B 5/0452; A61B 5/7275; A61B 5/7282; A61B 5/0245; A61B 5/7278; A61B 5/048; A61B 5/7246; A61B 5/00; A61B 5/0468; A61B 5/04525; A61B 5/02; A61B 5/4064; A61B 5/04; A61B 5/0004; A61B 5/486; A61B 5/72; A61B 5/7239; A61B 5/7242; A61B 5/7271; A61N 1/36064; A61N 1/36135; A61N 1/36132; A61N 1/08; A61N 1/37; A61N 1/3702; A61N 2005/0626; G06F 19/345; G06F 19/3437; G06F 19/3487; G06F 19/324; A61M 2230/04; A61M 2230/08; G08B 21/0453; G08B 21/0211; G06K 9/00885

See application file for complete search history.

(56) References Cited

U.S. PATENT DOCUMENTS 11,350,871 B2 * 6/2022 Osorio .............. A61N 1/36064

* cited by examiner

*Primary Examiner* — Deborah L Malamud
(74) *Attorney, Agent, or Firm* — CF3; Stephen Eisenmann

(57) ABSTRACT

Disclosed are methods and systems for treating epilepsy by stimulating a main trunk of a vagus nerve, or a left vagus nerve, when the patient has had no seizure or a seizure that is not characterized by cardiac changes such as an increase in heart rate, and stimulating a cardiac branch of a vagus nerve, or a right vagus nerve, when the patient has had a seizure characterized by cardiac changes such as a heart rate increase.

14 Claims, 37 Drawing Sheets

Related U.S. Application Data continuation-in-part of application No. 16/679,216, filed on Nov. 10, 2019, now Pat. No. 11,766,565, and a continuation-in-part of application No. 16/188,356, filed on Nov. 13, 2018, now Pat. No. 11,179,094, said application No. 16/679,216 is a continuation-in-part of application No. 15/437,155, filed on Feb. 20, 2017, now Pat. No. 10,682,515, said application No. 16/188,356 is a continuation of application No. 15/246,313, filed on Aug. 24, 2016, now Pat. No. 10,130,294, which is a continuation of application No. 14/583,099, filed on Dec. 25, 2014, now Pat. No. 9,451,894, said application No. 15/437,155 is a division of application No. 14/050,173, filed on Oct. 9, 2013, now Pat. No. 9,579,506, said application No. 14/583,099 is a continuation of application No. 13/899,267, filed on May 21, 2013, now Pat. No. 8,946,855, said application No. 14/050,173 is a continuation-in-part of application No. 13/601,099, filed on Aug. 31, 2012, now Pat. No. 9,314,633, said application No. 13/899,267 is a continuation of application No. 12/886,419, filed on Sep. 20, 2010, now Pat. No. 8,452,387, which is a continuation-in-part of application No. 12/884,051, filed on Sep. 16, 2010, now Pat. No. 8,571,643, said application No. 12/020,195 is a continuation-in-part of application No. 12/020,097, filed on Jan. 25, 2008, now Pat. No. 8,565,867, said application No. 13/601,099 is a continuation-in-part of application No. 12/020,195, filed on Jan. 25, 2008, now Pat. No. 8,260,426.

(51) Int. Cl.
| | |
|---|---|
| *A61B 5/024* | (2006.01) |
| *A61B 5/0245* | (2006.01) |
| *A61B 5/316* | (2021.01) |
| *A61B 5/349* | (2021.01) |
| *A61B 5/35* | (2021.01) |
| *A61B 5/352* | (2021.01) |
| *A61B 5/364* | (2021.01) |

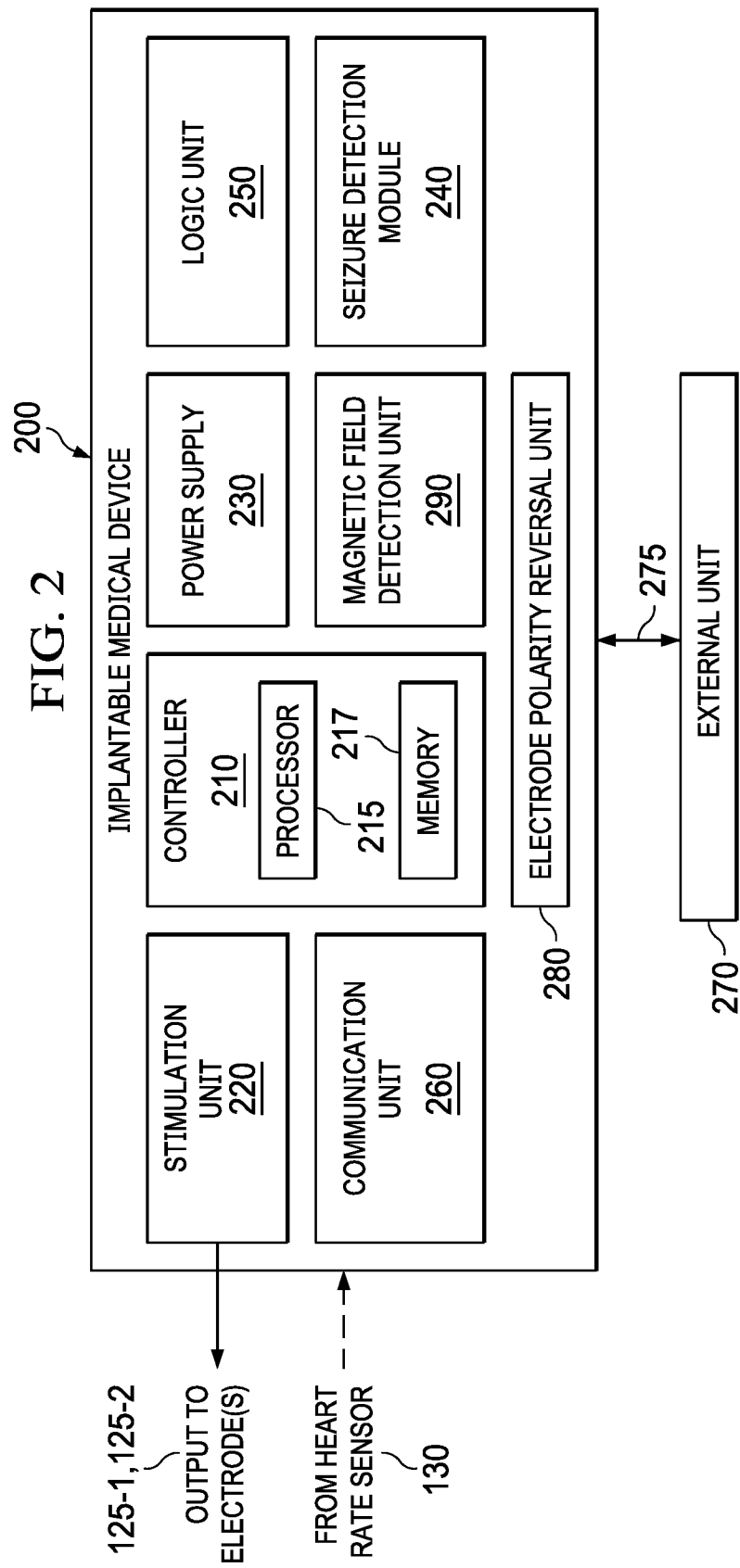

CONTINGENT CARDIO-PROTECTION FOR EPILEPSY PATIENTS

CROSS-REFERENCE TO RELATED APPLICATIONS

This presently being filed application is a continuation of and claims priority to co-pending U.S. patent application Ser. No. 16/777,930 entitled "Contingent Cardio-Protection For Epilepsy Patients", filed on Jan. 31, 2020, which is a continuation-in-part of and claims priority to co-pending U.S. patent application Ser. No. 16/188,356 entitled "Detecting or Validating a Detection of a State Change from a Template of Heart Rate Derivative Shape or Heart Beat Wave Complex", filed on Nov. 13, 2018, which is a continuation of and claims priority to U.S. patent application Ser. No. 15/246,313 entitled "Detecting or Validating a Detection of a State Change from a Template of Heart Rate Derivative Shape or Heart Beat Wave Complex", filed on Aug. 24, 2016 (Now U.S. Pat. No. 10,130,294) which is a continuation of and claims priority to U.S. patent application Ser. No. 14/583,099 entitled "Detecting or Validating a Detection of a State Change from a Template of Heart Rate Derivative Shape or Heart Beat Wave Complex", filed on Dec. 25, 2014 (Now U.S. Pat. No. 9,451,894) which is a continuation of and claims priority to U.S. patent application Ser. No. 13/899,267 entitled "Detecting or Validating a Detection of a State Change from a Template of Heart Rate Derivative Shape or Heart Beat Wave Complex", filed on May 21, 2013 (Now U.S. Pat. No. 8,948,855) which is a continuation of and claims priority to U.S. patent application Ser. No. 12/886,419 entitled "Detecting or Validating a Detection of a State Change from a Template of Heart Rate Derivative Shape or Heart Beat Wave Complex", filed on Sep. 20, 2010 (Now U.S. Pat. No. 8,452,387) which is a continuation-in-part of and claims priority to U.S. patent application Ser. No. 12/884,051 entitled "Detecting or Validating a Detection of a State Change from a Template of Heart Rate Derivative Shape or Heart Beat Wave Complex", filed on Sep. 16, 2010 (Now U.S. Pat. No. 8,571,643) and this presently being filed application is a continuation-in-part of and claims priority to co-pending U.S. patent application Ser. No. 16/679,216, entitled "Contingent Cardio-Protection For Epilepsy Patients", filed on Nov. 10, 2019 which is a continuation-in-part of and claims priority to co-pending U.S. patent application Ser. No. 15/437,155 entitled "Contingent Cardio-Protection For Epilepsy Patients", filed on Feb. 20, 2017, which claims priority to and is a divisional application of U.S. patent application Ser. No. 14/050,173 entitled "Contingent Cardio-Protection For Epilepsy Patients", filed on Oct. 9, 2013 (now U.S. Pat. No. 9,579,506), which claims priority to and is a continuation-in-part of U.S. patent application Ser. No. 13/601,099 entitled "Contingent Cardio-Protection For Epilepsy Patients", filed on Aug. 31, 2012 (now U.S. Pat. No. 9,314,633), which claims priority to and is a continuation-in-part of U.S. patent application Ser. No. 12/020,195 entitled "Method, Apparatus and System for Bipolar Charge Utilization during Stimulation by an Implantable Medical Device", filed on Jan. 25, 2008 (now U.S. Pat. No. 8,260,426) and claims priority to and is a continuation-in-part of U.S. patent application Ser. No. 12/020,097 entitled "Changeable Electrode Polarity Stimulation by an Implantable Medical Device", filed on Jan. 25, 2008 (now U.S. Pat. No. 8,565,867) all of which are incorporated herein by reference in their entireties.

BACKGROUND OF THE DISCLOSURE

This disclosure relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestation of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs), conduction (e.g., bundle branch block) and repolarization abnormalities (e.g., Q-T prolongation, which occurs primarily during (ictal) but also between seizures (inter-ictally). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharmaco-resistant epilepsies may, for example, account for abnormalities that increase the risk of sudden death such as prolongation of the Q-T interval which leads to often fatal tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympathetic-parasympathetic tone to normal levels, a therapeutic objective that may be accomplished by enhancing parasympathetic activity through among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures—remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos. 4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651,373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

This disclosure relates to medical device systems and methods capable of detecting or validating a detection and, in some embodiments, treating an occurring or impending state change.

Approximately 60 million people worldwide are affected with epilepsy, of whom roughly 23 million suffer from epilepsy resistant to multiple medications. In the USA alone, the annual cost of epilepsy care is USD 12 billion (in 1995 dollars), most of which is attributable to subjects with pharmaco-resistant state changes. Pharmaco-resistant state changes are associated with an increase mortality and morbidity (compared to the general population and to epileptics whose state changes are controlled by medications) and with markedly degraded quality of life for patients. State changes may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present disclosure is a signal applied from a medical device, e.g., a neurostimulator.

A "therapeutic signal" refers to a stimulation signal delivered to a patient's body with the intent of treating a medical condition through a suppressing (blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of the nervous system, stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic state changes) see Osorio et al., Ann Neurol 2005; Osorio & Frei IJNS 2009). The mechanisms thorough which this suppressing effect takes place are described in the foregeoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (wave annihilation) may be exerted through collision with identical, similar or dissimilar waves, a concept borrowed from wave mechanics, or through phase resetting (Winfree).

In some cases, electrotherapy may be provided by implanting an electrical device, i.e., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

Although non-contingent, programmed periodic stimulation (also referred to as "open-loop," "passive," or "non-feedback" stimulation (i.e., electrotherapy applied without reference to sensed information)) is the prevailing modality, contingent (also referred to as "closed-loop," "active," or "feedback" stimulation (i.e., electrotherapy applied in response to sensed information)) stimulation schemes have been proposed. Included in such proposed stimulation schemes are electrotherapy applied in response to an indication of an impending, occurring, or occurred state change, with the intent of reducing the duration, the severity, or both of a state change or a post-state change recovery period. However, such stimulation schemes would require reasonably sensitive techniques for indicating an impending, occurring, or occurred state change.

Even if closed-loop neurostimulation, or any other therapy for epilepsy, is not performed, reasonably sensitive and/or specific techniques for indicating an impending, occurring, or occurred state change would be desirable for warning of state changes to minimize risk of injuries and for logging to assess the state of the disease and assess the efficacy of therapies. Numerous studies have shown that self-reporting by patients, such as in state change diaries, generally only captures about half of all state changes having both electroencephalographic (EEG) and clinical signatures. Roughly a third of all patients do not identify any of their state changes. Detection of brain state changes may be accomplished using different body signals, but cortical electrical signals are most commonly used for this purpose. For multiple reasons (e.g., signal to noise ratio, stability of signals, etc.) intracranial and not scalp recordings are the modality of choice for prolonged (e.g., weeks to years) recording of cortical signals. However, since use of intracranial signals requires costly and burdensome surgical procedures that are associated with certain potentially serious complications, they are neither accessible nor acceptable to the majority of hundreds of thousands of patients that could benefit from them. Use of non-cerebral or extra-cerebral signals has emerged as a viable, useful, and highly cost-effective alternative to electrical cortical signals for the detection, warning, and logging of brain state changes, such as epileptic seizures.

In one aspect of the present disclosure, a method for indicating an occurrence of a state change is provided. In one aspect of the present disclosure, the method comprises obtaining a time series of cardiac data from a patient; determining a reference heart rate parameter from said cardiac data; determining a heart rate derivative shape from said time series of cardiac data, wherein said heart rate derivative shape comprises at least one characteristic selected from a number of phases relative to said reference heart rate parameter, a number of extrema of said heart rate derivative, a number of directions of change of said heart rate derivative, an area under the curve of at least one phase, a number of positive phases, or a number of negative phases; and indicating an occurrence of a state change based upon a determination that said heart rate derivative shape matches a state change template in said at least one characteristic, wherein said at least one characteristic of said state change template comprises two or more phases relative to said reference heart rate parameter, two or more extrema of said heart rate derivative, three or more directions of change of said heart rate derivative, a number of positive phases, or a number of negative phases, provided the total number of positive phases and negative phases is two or more.

In another aspect of the present disclosure, a method for indicating an occurrence of a state change is provided. In one aspect of the present disclosure, the method comprises obtaining data relating to at least a portion of a heart beat complex from a patient; comparing said at least said portion of said heart beat complex with a corresponding portion of a reference heart beat complex template of said patient; and indicating an occurrence of a state change based upon a determination that said heart beat complex fails to match said reference heart beat complex template.

In yet another aspect of the present disclosure, a computer readable program storage device is provided that is encoded with instructions that, when executed by a computer, perform a method described above.

In one aspect of the present disclosure, a medical device is provided comprising a computer readable program storage device as described above.

SUMMARY OF THE DISCLOSURE

In one aspect, the present disclosure relates to a method of treating a patient having epilepsy comprising receiving at least one body data stream, analyzing the at least one body data stream using a seizure or event detection algorithm to detect whether or not the patient is having and/or has had an epileptic seizure, receiving a cardiac signal of the patient, applying a first electrical signal to a vagus nerve of the patient based on a determination that the patient is not having and/or has not had an epileptic seizure characterized by a decrease in the patient's heart rate, wherein the first electrical signal is not a vagus nerve conduction blocking electrical signal, and applying a second electrical signal to a vagus nerve of the patient based on a determination that the patient is having and/or has had an epileptic seizure characterized by a decrease in the patient's heart rate, wherein the second electrical signal is a pulsed electrical signal that blocks action potential conduction in the vagus nerve.

In one aspect, the present disclosure relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing; in response to a determination that the patient has had an epileptic seizure, determining whether or not the seizure is characterized by a decrease in the patient's heart rate, applying a first electrical signal to a vagus nerve of the patient based on a determination that the patient has had an epileptic seizure characterized by a decrease in the patient's heart rate, wherein the first electrical signal is a pulsed electrical signal that blocks action potential conduction in the vagus nerve; and applying a second electrical signal to a vagus nerve of the patient based on one of a) a determination that the patient has not had an epileptic seizure, and b) a determination that the patient has had an epileptic seizure that is not characterized by a decrease in the patient's heart rate, wherein the second electrical signal is not a vagus nerve conduction blocking electrical signal.

In one aspect, the present disclosure relates to a system for treating a medical condition in a patient, comprising at least one electrode coupled to a vagus nerve of the patient, a programmable electrical signal generator, a sensor for sensing at least one body data stream, a seizure detection module capable of analyzing the at least one body data stream and determining, based on the analyzing, whether or not the patient is having and/or has had an epileptic seizure, a heart rate determination unit capable of determining a heart rate of a patient proximate in time to an epileptic seizure detected by the seizure detection module, and a logic unit for applying a first electrical signal to the vagus nerve using the at least one electrode based on a determination by the seizure detection module that the patient is having and/or has had an epileptic seizure characterized by a decrease in the patient's heart rate, wherein the first electrical signal is a pulsed electrical signal that blocks action potential conduction in the vagus nerve, and for applying a second electrical signal to the vagus nerve using the at least one electrode as a cathode based upon one of a) a determination that the patient is not having and/or has not had an epileptic seizure, and b) a determination that the patient is having and/or has had an epileptic seizure that is not characterized by a decrease in the patient's heart rate, wherein the second electrical signal is not a vagus nerve conduction blocking electrical signal. In one embodiment, the seizure detection module may comprise the heart rate determination unit.

In one aspect, the present disclosure relates to a method of treating a patient having epilepsy comprising applying a first electrical signal to a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by a decrease in the patient's heart rate, applying a second, closed-loop electrical signal to a vagus nerve of the patient based on a determination that the epileptic seizure is not characterized by a decrease in the patient's heart rate, and applying a third, closed-loop electrical signal to a vagus nerve of the patient based on a determination that the seizure is characterized by a decrease in the patient's heart rate, wherein the third electrical signal is applied to block action potential conduction on the vagus nerve.

In one aspect, the present disclosure relates to a method of controlling a heart rate of an epilepsy patient comprising sensing a kinetic signal of the patient; analyzing said kinetic signal to determine at least one kinetic index; receiving a cardiac signal of the patient; analyzing the cardiac signal to determine the patient's heart rate; determining if the patient's heart rate is commensurate with the at least one kinetic index; and applying a first electrical signal to a vagus nerve of the patient based on a determination that the patient's heart rate is not commensurate with the kinetic index. In one embodiment, the at least one kinetic index comprises at least one of an activity level or an activity type of the patient, and determining if the heart rate is commensurate with the kinetic index comprises determining if the heart rate is commensurate with the at least one of an activity level or an activity type.

In one aspect, the present disclosure relates to a method of controlling a heart rate of an epilepsy patient comprising sensing at least one of a kinetic signal and a metabolic (e.g., oxygen consumption) signal of the patient; receiving a cardiac signal of the patient; analyzing the cardiac signal to determine the patient's heart rate; determining if the patient's heart rate is commensurate with the at least one of a kinetic and a metabolic signal of the patient; and applying a first electrical signal to a vagus nerve of the patient based on a determination that the patient's heart rate is not commensurate with the at least one of a kinetic signal and a metabolic signal. In one embodiment, the method further comprises determining at least one of an activity level or an activity type of the patient based on the at least one of a kinetic and a metabolic signal, and determining if the heart rate is commensurate with the kinetic signal comprises determining if the heart rate is commensurate with the at least one of an activity level or an activity type.

In one aspect, the present disclosure relates to a method of treating a patient having epilepsy comprising sensing at least one body signal of the patient; determining whether or not the patient is having or has had an epileptic seizure based on the at least one body signal; sensing a cardiac signal of the patient; determining whether or not the seizure is associated with a change in the patient's cardiac signal; applying a first therapy to a vagus nerve of the patient based on a determination that the patient is having or has had an epileptic seizure that is not associated with a change in the patient's cardiac signal, wherein the first therapy is selected from an electrical, chemical, mechanical (e.g., pressure) or thermal signal. The method further comprises applying a second therapy to a vagus nerve of the patient based on a determination that the patient has had an epileptic seizure associated with a change in the patient's cardiac signal, wherein the second therapy is selected from an electrical, chemical, mechanical (e.g., pressure) or thermal signal. In some embodiments, a third therapy may be applied to a vagus nerve based a determination that the patient has not had an epileptic seizure, wherein the third therapy is selected form an electrical, chemical, mechanical or thermal signal.

BRIEF DESCRIPTION OF THE DRAWINGS

The disclosure may be understood by reference to the following description taken in conjunction with the accompanying drawings, in which like reference numerals identify like elements, and in which:

FIG. 2 illustrates a block diagram depiction of an implantable medical device of FIG. 1, in accordance with one illustrative embodiment of the present disclosure;

Figure 1A:
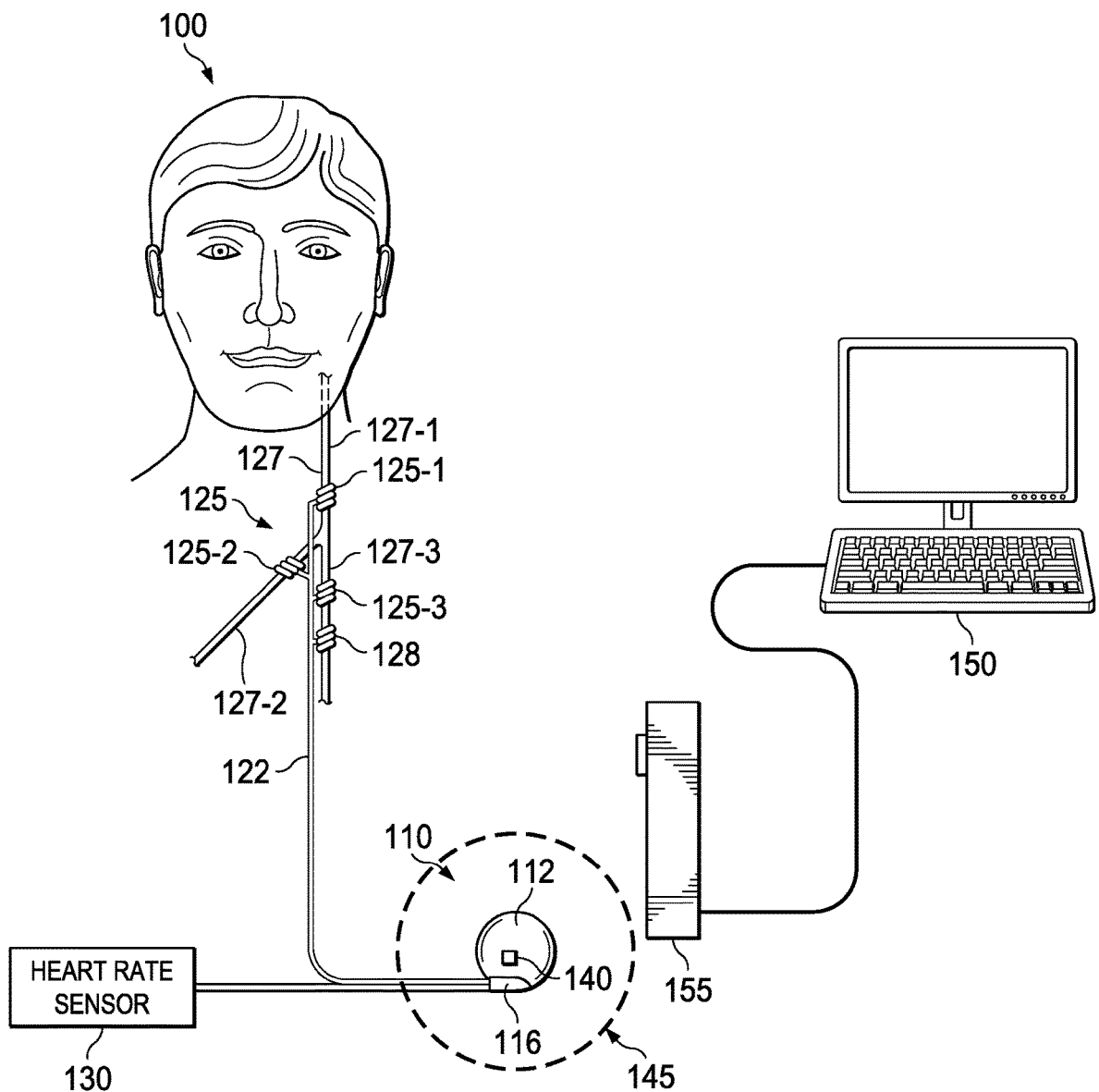
FIGS. 1A-1E provide stylized diagrams of an implantable medical device implanted into a patient's body for providing first and second electrical signals to a vagus nerve of a patient for treating epileptic seizures, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuroplasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization. The terms tachycardia and bradycardia are used here in a relative (i.e., any decrease or decrease in heart rate relative to a reference value) or in an absolute sense (i.e., a pathological change relative to a normative value). In particular, "tachycardia is used interchangeably with an increase heart rate and "bradycardia" may be used interchangeably with a decrease in heart rate.

A variety of stimulation therapies may be provided in embodiments of the present disclosure. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stair step pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. Sec, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

Cardiac signals suitable for use in embodiments of the present disclosure may comprise one or more of an electrical (e.g., EKG), acoustic (e.g., phonocardiogram or ultrasound/ECHO), force or pressure (e.g., apexcardiogram), arterial pulse pressure and waveform or thermal signals that may be recorded and analyzed to extract features such as heart rate, heart rate variability, rhythm (regular, irregular, sinus, ventricular, ectopic, etc.), morphology, etc.

It appears that sympatho-vagal imbalance (lower vagal and higher sympathetic tone) plays an important role in generation of a wide spectrum of ictal and interictal alterations in cardiac dynamics, ranging from rare unifocal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present disclosure provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECOG, kinetic (e.g., amplitude velocity, direction of movements) and cognitive (e.g., complex reaction time).

In one embodiment, the present disclosure provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
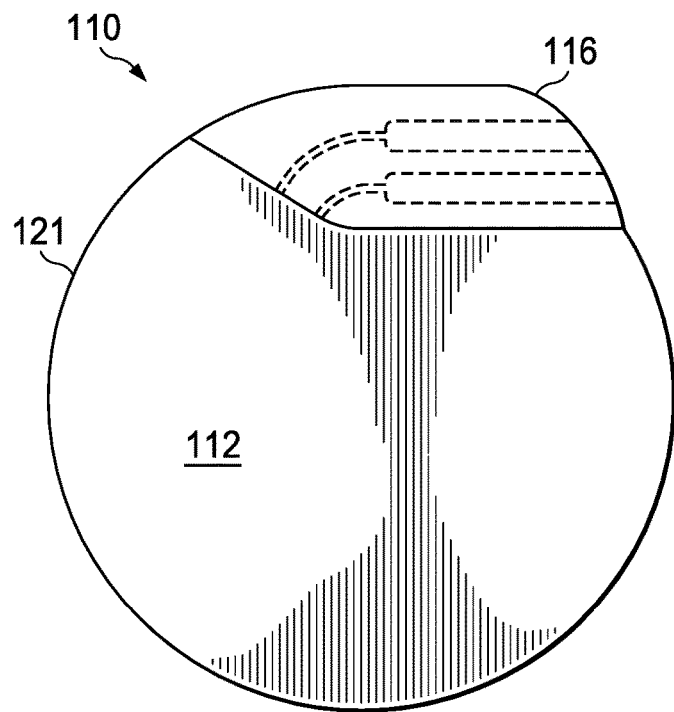

FIGS. 1A-1E depict a stylized implantable medical system 100 for implementing one or more embodiments of the present disclosure. FIGS. 1A and 1B illustrate an electrical signal generator 110 having main body 112 comprising a case or shell (commonly referred to as a "can") 121 (FIG. 1B) with a header 116 for connecting to a lead assembly 122. An electrode assembly 125, preferably comprising at least an electrode pair, is conductively connected to the distal end of an insulated, electrically conductive lead assembly 122, which preferably comprises a plurality of lead wires (at least one wire for each electrode of the electrode assembly 125). Lead assembly 122 is attached at its proximal end to one or more connectors on header 116 (FIG. 1B).

Electrode assembly 125 may be surgically coupled to a target tissue for delivery of a therapeutic electrical signal, which may be a pulsed electrical signal. The target tissue may be a cranial nerve, such as a vagus nerve 127 (FIGS. 1A, 1C-E) or another cranial nerve such as a trigeminal nerve. Electrode assembly 125 includes one or more electrodes 125-1, 125-2, 125-3, which may be coupled to the target tissue. The electrodes may be made from any of a variety of conductive metals known in the art, e.g., platinum, iridium, oxides of platinum or iridium, or combinations of the foregoing. In one embodiment, the target tissue is a vagus nerve 127, which may include an upper main trunk portion 127-1 above a cardiac branch 127-2, and a lower main trunk portion 127-3 below the cardiac branch.

Figure 1C:
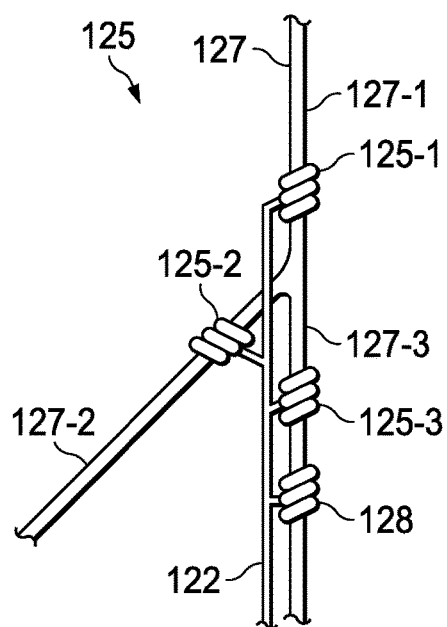

In one embodiment, at least one electrode may be coupled to the main trunk of the vagus nerve, and at least one electrode 125-2 may be coupled to a cardiac branch 127-2 of the vagus nerve (FIG. 1C). The at least one main trunk electrode may be coupled to an upper main trunk 127-1 (e.g., electrode 125-1, FIG. 1C) or a lower main trunk 127-3 (e.g., electrode 125-3). The at least one main trunk electrode (125-1, 125-3) may be used as a cathode to provide a first electrical signal to the upper (127-1) or lower (127-3) main trunk. Cardiac branch electrode 125-2 may be used as a cathode to provide a second electrical signal to cardiac branch 127-2. An additional electrode to function as the anode may be selected from one or more of the other electrodes in electrode assembly 125, can 121, or a dedicated anode.

In some embodiments (FIGS. 1D, 1E), electrode assembly 125 may include a main trunk electrode pair comprising a cathode 125-1*a* and an anode 125-1*b* for coupling to a main trunk of a vagus nerve 127. The main trunk electrode pair 125-1*a*, 125-1*b* may be coupled to an upper main trunk 127-1 of a vagus nerve (FIG. 1D), or to a lower main trunk 127-3 (FIG. 1E) for delivering a first electrical signal. Without being bound by theory, it is believed that few or no vagal afferent fibers in the lower main trunk 127-3 pass into cardiac branch 127-2 and, accordingly, that effects of the first electrical signal on cardiac function may be minimized by coupling electrode pair 125-1*a* and 125-1*b* to the lower main trunk 127-3 instead of upper main trunk 127-1. Cardiac effects may also be minimized by alternative embodiments in which the first electrical signal is applied to a lower main trunk 127-3 using a single electrode (e.g., 125-3, FIG. 1C) as a cathode and an anode that is not coupled to the vagus nerve 127 (e.g., by using can 121 as an anode).

In some embodiments (FIGS. 1D, 1E), electrode assembly 125 may include a cardiac branch electrode pair comprising a cathode 125-2*a* and an anode 125-2*b* for coupling to a cardiac branch of a vagus nerve. The second cardiac branch electrode pair may be used to provide a second electrical signal to a cardiac branch of the nerve to affect the cardiac function of the patient.

Referring again to FIGS. 1C-1E, a first electrical signal may be provided to generate afferent action potentials in a main trunk of a vagus nerve to modulate electrical activity of the patient's brain without significantly affecting the patient's heart rate. The second electrical signal may generate efferent action potentials to module the cardiac activity of the patient, and in particular to slow the patient's heart rate (e.g., to treat an epilepsy patient having seizures characterized by tachycardia) ictal and maintain or restore a sympathetic/parasympathetic balance to a non-pathological state. The first electrical signal may be applied to the main trunk of the vagus nerve in a variety of ways, so long as at least one electrode is coupled to the main trunk as a cathode. As noted, the cathode may be coupled to either an upper (127-1) or lower (127-3) main trunk, and an anode may be provided by any of the other electrodes on the vagus nerve (e.g., 125-1b, 125-2b, 125-3, FIGS. 1C-1E) or by a separate anode not coupled to the vagus nerve (e.g., can 121). In one alternative embodiment, an electrode 125-3 may be coupled to a lower main trunk 127-3 of the vagus nerve to function as an anode. In yet another embodiment, each individual electrode element in FIGS. 1A-E (e.g., 125-1, 125-2, 125-3, 125-1a, 125-1g, 125-2a, 125-2b) may comprise an electrode pair comprising both an anode and a cathode. In an additional embodiment, each individual electrode element may comprise three electrodes (e.g., one serving as cathode and the other two as anodes). Suitable electrode assemblies are available from Cyberonics, Inc., Houston, Texas, USA as the Model 302, PerenniaFlex and PerenniaDura electrode assemblies. In view of the present disclosure, persons of skill in the art will appreciate that many electrode designs could be used in embodiments of the present disclosure including unipolar electrodes.

Embodiments of the present disclosure may comprise electrical signals with either charge-balanced or non-charge-balanced pulses (e.g., monopolar/monophasic, direct current (DC)). Charge-balanced pulses involve a first phase in which the stimulation occurs (i.e., action potentials are induced in target nerve fibers), and a second phase in which the polarity of the electrodes are reversed (i.e., the stimulation phase cathode becomes the charge-balancing phase anode, and vice versa). The result is a pulse having two opposite-polarity phases of equal charge, such that no net charge flows across the electrode during a pulse. Charge-balancing is often used to avoid damage to the electrodes that may result if a pulse results in a net charge flowing across the electrodes.

In some instances, charge-balancing may involve a passive discharge phase as illustrated in, e.g., FIG. 1A of US Publication 2006/0173493, which is hereby incorporated by reference in its entirety. In passive charge-balancing, the charge-balancing phase typically involves allowing a capacitor having a charge equal to the charge applied to the nerve during the stimulation phase to discharge through the polarity-reversed electrodes. Passive charge-balancing typically uses much lower initial current than the stimulation phase, with the current declining to zero over a much longer time period than the pulse width of the stimulation phase. A lower current is typically selected in the charge-balancing phase so as to avoid or minimize nerve recruitment during the charge-balancing phase. In active charge-balancing, the charge-balancing phase is not accomplished by the passive discharge of a capacitor, but by providing a second phase having an opposite polarity but the same charge magnitude (pulse width multiplied by current) as the first phase. As is usually the case with passive charge-balancing, active charge-balancing typically involves a much lower current that is applied over a longer time period than the stimulation phase, so as to avoid nerve recruitment. In some instances, however, the active charge-balancing phase may be used as a second stimulation phase by selecting a current magnitude of the cathode in the charge-balancing phase (typically a second electrode, which may be the anode of the initial stimulation phase) that is sufficient to generate action potentials in nerve fibers of the target tissue.

Embodiments of the present disclosure may be implemented using passive charge balancing or active charge-balancing, and the latter may be provided as a stimulation phase or a non-stimulation phase. Some embodiments may be implemented with non-charge-balanced pulses. Persons of skill in the art, having the benefit of the present disclosure, may select the type of charge balancing (if desired) based upon a number of factors including but not limited to whether or not the charge-balancing is intended to affect the cardiac cycle or not, whether afferent or efferent stimulation is desired, the number and location of available electrodes for applying the electrical signal, the fibers intended to be recruited during a particular phase and their physiological effects, among many other factors.

In the discussion of electrical signals in the present disclosure, unless otherwise stated, references to electrodes as cathodes or anodes refers to the polarities of the electrodes during a stimulation phase of a pulse, whether the pulse is a charge-balanced pulse or a non-charge-balanced pulse (e.g., monopolar/monophasic or DC). It will be appreciated that where charge-balanced pulses are employed, the polarities will be reversed during a charge-balancing phase. Where active charge-balancing is used, cardiac effects may be further amplified or ameliorated, depending upon the location of the electrodes being used.

Returning to FIG. 1A, in some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the can 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/$CO_2$ concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which in one embodiment does not include an electrode but in alternative embodiments may contain up to three electrodes that serve as cathode(s) and anode(s) in any possible combination. Lead assembly 122 may further be secured, while retaining the ability to flex, by a suture connection 130 to nearby tissue (FIG. 1C). In particular embodiments, any of first, second and third electrodes 125-1, 125-2, and 125-3 may be used as either a cathode or as an anode. In general, the foregoing electrodes may be used as a cathode when the particular electrode is the closest electrode (among a plurality of electrodes) to the target organ (e.g., heart, brain, stomach, liver, etc.) to be stimulated. While a single electrode (e.g., 125-1, 125-2, or 125-3) is illustrated in connection with upper main trunk 127-1, cardiac branch 127-2, and lower main trunk 127-3 in FIGS. 1A and 1C for simplicity, it will be appreciated that one or more additional electrodes can be provided on each of the foregoing neural structures to provide greater flexibility in stimulation.

In one embodiment, the open helical design of the electrodes 125-1, 125-2, 125-3, is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after surgical implantation. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the disclosure, a body data stream may be analyzed to determine whether or not a seizure has occurred. Many different body data streams and seizure detection indices have been proposed for detecting epileptic seizures. Additional details on method of detecting seizure from body data are provided in U.S. Pat. Nos. 8,337,404 and 8,382,667, both issued in the name of the present applicant and both entitled, "Detecting, Quantifying, and/or Classifying Seizures Using Multimodal Data," as well as in co-pending U.S. patent application Ser. No. 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing patents and co-pending applications.

In one embodiment, the present disclosure provides a method for treating a patient with epilepsy in which a body data stream is analyzed using a seizure detection algorithm to determine whether or not the patient has had an epileptic seizure. As used herein, the term "has had an epileptic seizure" includes instances in which a seizure onset has been detected, as well as instances in which the seizure onset has been detected and the seizure is still ongoing (i.e., the seizure has not ended). If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only if the analysis results in a determination that the patient is having and/or has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery of the first and second signals may be interspersed or interleaved.

The first electrode may be used as a cathode to provide an afferent first electrical signal to modulate the brain of the patient via main trunk electrode 125-1. Electrode 125-1 may generate both afferent and efferent action potentials in vagus nerve 127. One or more of electrodes 125-2 and 125-3 are used as anodes to complete the circuit. Where this is the case, some of the action potentials may be blocked at the anode(s), with the result that the first electrical signal may predominantly modulate the brain by afferent actions traveling toward the brain, but may also modulate one or more other organs by efferent action potentials traveling toward the heart and/or lower organs, to the extent that the efferent action potentials are not blocked by the anode(s).

The second electrode may be used as a cathode to provide an efferent second electrical signal to slow the heart rate of the patient via cardiac branch electrode 125-2. Either first electrode 125-1 or a third electrode 125-3 (or can 121) may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width.

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities or changes in EKG morphology or rhythm relative to an interictal morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, interpulse-interval, stimulation on-time, and stimulation off-time, among other parameters and degree, rate or type of charge balancing.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber is directional—that is, endogenous or natural action potentials can generally propagate action potentials in only one direction (e.g., afferently to the brain or efferently to the heart and/or viscera). That direction is referred to as the orthodromic direction. Exogenous stimulation (e.g., by electrical pulses) may induce action potentials in both the orthodromic direction as well as the antidromic direction. Depending upon the desired effects of stimulation (e.g., afferent modulation of the brain, efferent modulation of the heart, etc.) certain measures (e.g., cooling, pressure, etc.) may be taken to block propagation in either the efferent or the afferent direction. It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode. Action potentials generated at upper main trunk electrode 125-1 and traveling toward the heart on cardiac branch 127-2 may be blocked by cardiac branch anode 125-2. Action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Action potentials may be generated and allowed to travel to the heart by making the electrode 125-2 the cathode. If cardiac branch electrode 125-2 is used as a cathode, action potentials will reach the heart in large numbers, while action potentials traveling afferently toward the brain may be blocked in the upper trunk if upper electrode 125-1 is made the anode.

In a further embodiment of the disclosure, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Turning now to FIG. 2, a block diagram depiction of an implantable medical device, in accordance with one illustrative embodiment of the present disclosure is illustrated. The IMD 200 may be coupled to various electrodes 125 and/or 127 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, microprocessors, etc., that are capable of executing a variety of software components. The processor may receive, pre-condition and/or condition sensor signals, and may control operations of other components of the IMD 200, such as stimulation unit 220, seizure detection module 240, logic unit 250, communication unit, 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection module 240 to determine whether or not the patient is having and/or has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection module 240. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

Figure 1D:
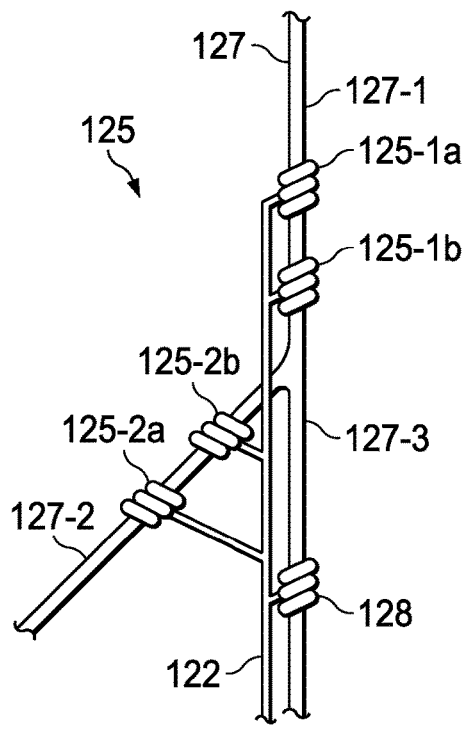
Figure 1E:
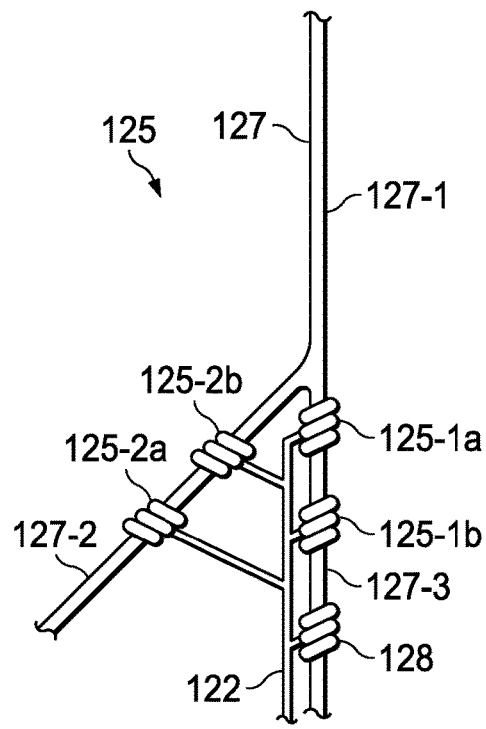

In one embodiment, a method of treating an epileptic seizure is provided that involves providing simultaneously both a first electrical signal to a main trunk of a vagus nerve and a second electrical signal to a cardiac branch of the vagus nerve. As used herein "simultaneously" refers to the on-time of the first and second signals, and does not require that individual pulses of the first signal and the second signal be simultaneously applied to target tissue. The timing of pulses for the first electrical signal and the second electrical signal may be determined by controller 210 in conjunction with stimulation unit 220. Where active charge-balancing is used, it may be possible to use the active charge-balancing phase of pulses of the first electrical signal as the stimulation phase of the second electrical signal by selecting a current magnitude of the cathode in the charge-balancing phase (typically a second electrode, which may be the anode of the initial stimulation phase) that is sufficient to generate action potentials in nerve fibers of the target tissue. Controller 210 may in some embodiments provide simultaneous delivery of first and second electrical signals by interleaving pulses for each of the first and second electrical signals based upon the programmed timing of pulses for each signal and the appropriate polarity of each of first and second electrodes 125-1 and 125-2. In some embodiments, additional electrodes may be used to minimize the induction of action potentials to the heart or the brain provided by the first electrical signal or the second electrical signal. This may be accomplished, in one embodiment, by using an anode located on either the upper main trunk or the cardiac branch to block impulse conduction to the heart or brain from the cathode, or by providing dedicated electrode pairs on both the main trunk and cardiac branches (FIGS. 1D, 1E). When beneficial, steps to avoid collisions of actions potentials travelling in opposite directions may be implemented, while steps to promote collisions may be taken when clinically indicated. In some embodiments, the method further includes sensing a cardiac signal and a kinetic signal of the patient, and detecting a seizure event with a seizure detection algorithm.

In one embodiment, a first electrical signal is applied to a main trunk of a vagus nerve and a second electrical signal is simultaneously applied to a cardiac branch of a vagus nerve. A pulse of the first electrical signal is generated with the electrical signal generator 110 and applied to the main trunk of the vagus nerve using a first electrode (e.g., 125-1, 125-1*a*) as a cathode and a second electrode (e.g., 125-1*b*, 125-3, or 125-2) as an anode. The method includes sensing a cardiac signal and a kinetic signal of the patient, and detecting a seizure event with a seizure detection algorithm. A pulse of the second electrical signal (having the appropriate pulse width and current) is generated and applied (under appropriate timing control by controller 110 and stimulation unit 220) to the cardiac branch of the vagus nerve using a second electrode (e.g., 125-2. 125-2*a*) as a cathode and another electrode (e.g., 125-3, 125-1, 125-2*b*) as an anode. Another pulse of the first electrical signal may thereafter be generated and applied to the main trunk under timing and parameter control of controller 210 and stimulation unit 220. By appropriate selection of cathodes and anodes, the first and second electrical signals may be interleaved and provided simultaneously to the main trunk and cardiac branches of the vagus nerve. In some embodiments, the number of electrodes may be minimized by provided a polarity reversal unit that may rapidly change the polarity of particular electrodes to allow their use in delivering both the first and second signals.

The IMD 200 is capable of delivering stimulation that can be contingent, periodic, random, coded, and/or patterned. The stimulation signals may comprise an electrical stimulation frequency of approximately 0.1 to 10,000 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
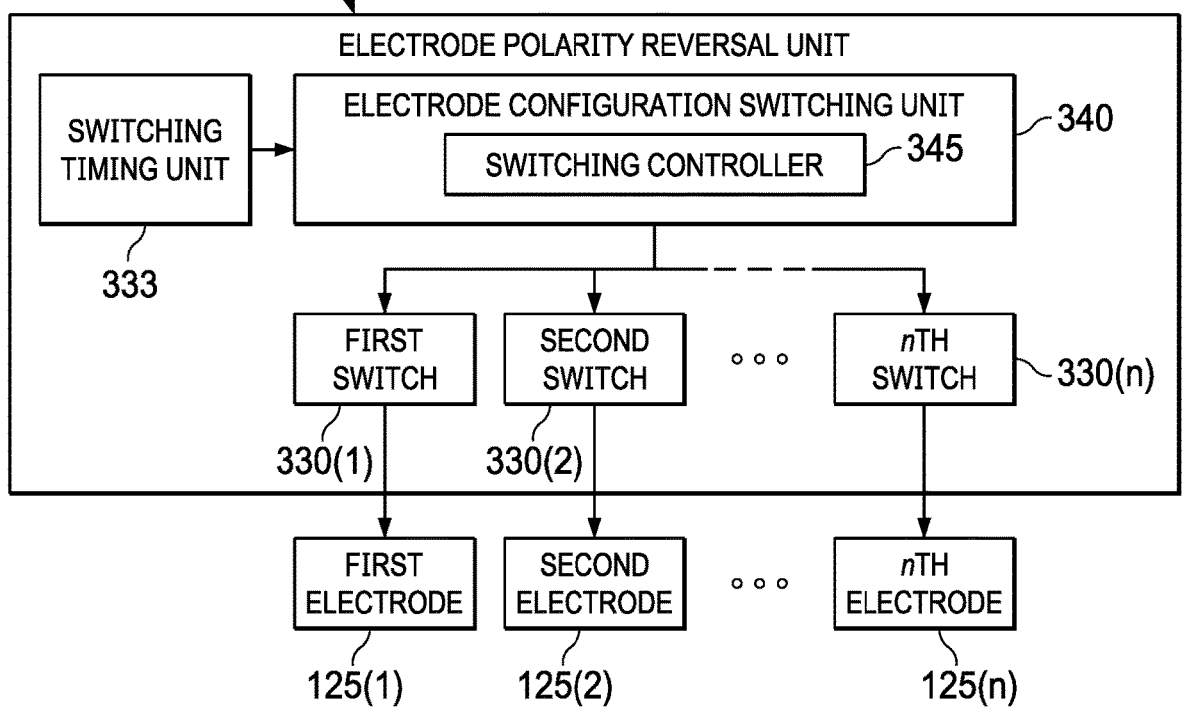
FIG. 3 illustrates a block diagram depiction of an electrode polarity reversal unit shown in FIG. 2, in accordance with one illustrative embodiment of the present disclosure.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present disclosure greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-n) may be electrical devices, electro-mechanical devices, and/or solid state devices (e.g., transistors).

Figure 4:
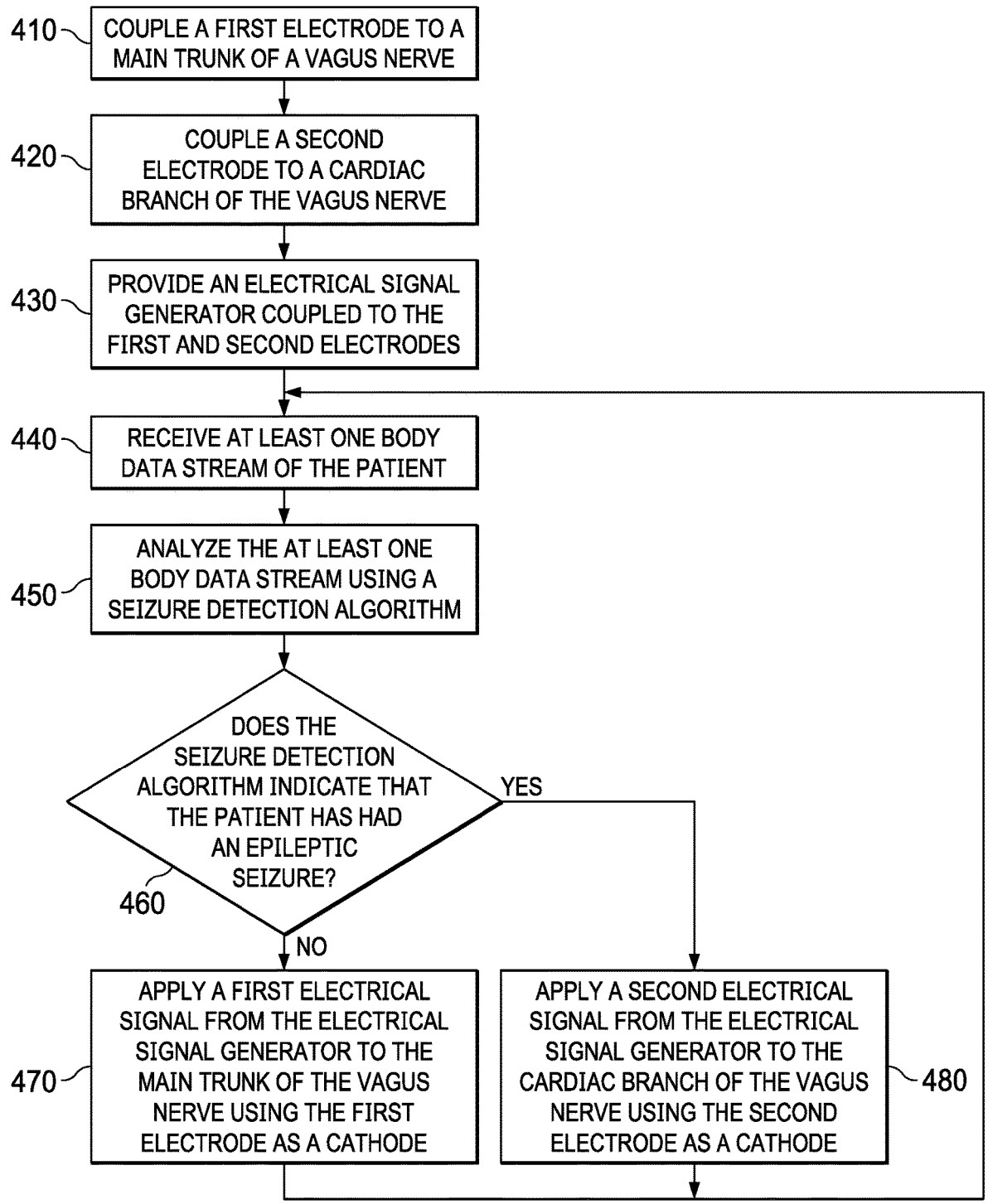
FIG. 4 illustrates a flowchart depiction of a method for providing first and second electrical signals to a main trunk and a cardiac branch of a vagus nerve, respectively, based upon whether or not the patient is having and/or has had an epileptic seizure, in accordance with an illustrative embodiment of the present disclosure.

FIG. 4 shows one embodiment of a method of treating a patient having epilepsy according to the present disclosure. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient is having and/or has had an epileptic seizure (460).

If the algorithm indicates that the patient is not having and/or has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient is having and/or has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient is having and/or has had an epileptic seizure.

In an alternative embodiment, if the seizure detection algorithm indicates that the patient is having and/or has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body. In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

In alternative embodiments, both the first electrode and the second electrode may be coupled to a cardiac branch of a vagus nerve, with the first electrode (e.g., anode) being proximal to the brain relative to the second electrode, and the second electrode (e.g., cathode) being proximal to the heart relative to the first electrode.

Figure 5:
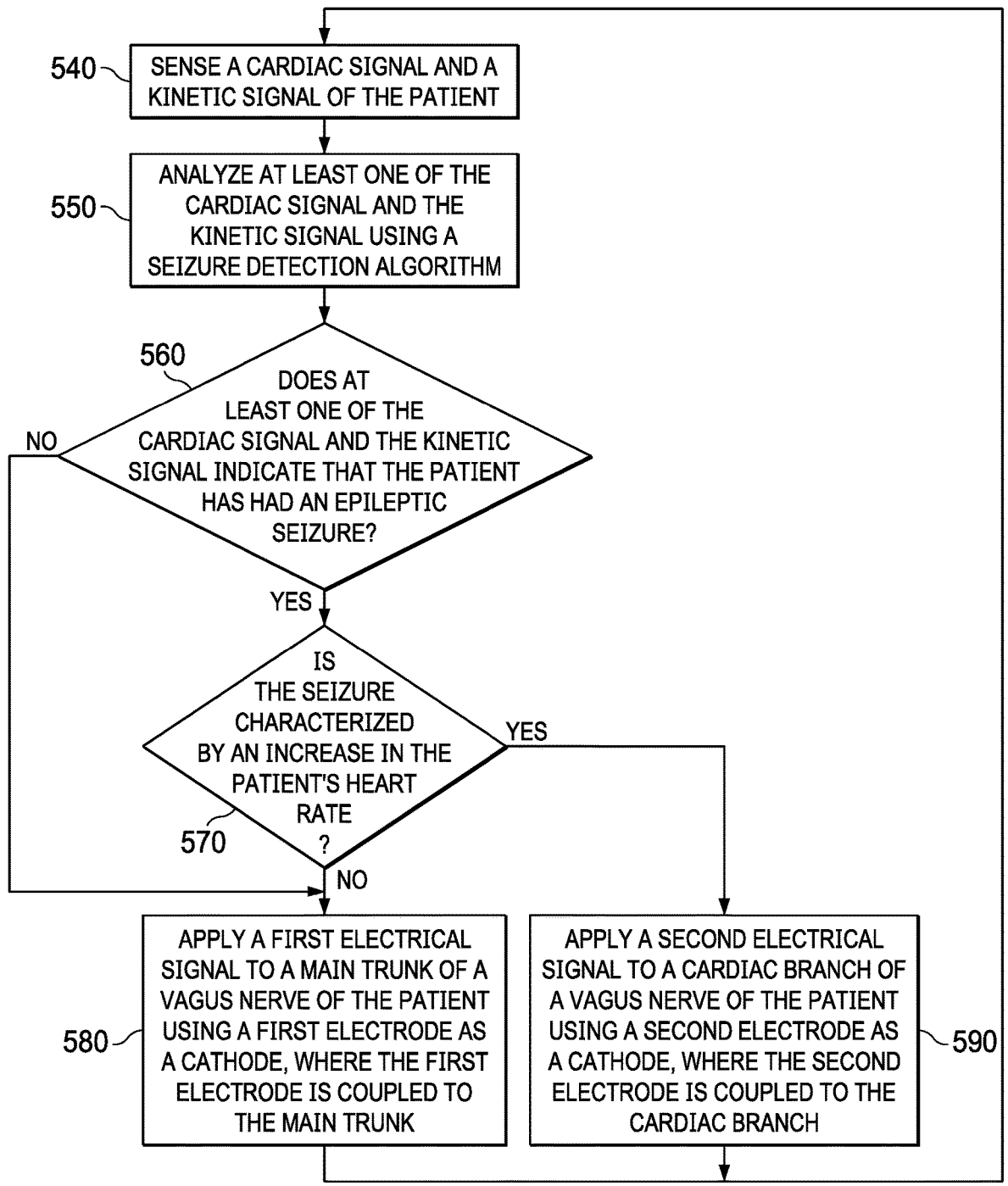
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient is having and/or has had an epileptic seizure, and whether the seizure is characterized by an increase in heart rate, in accordance with an illustrative embodiment of the present disclosure.

FIG. 5 is a flow diagram of another method of treating a patient having epilepsy according to the present disclosure. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient is having and/or has had an epileptic seizure (560).

If the patient is not having and/or has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient is having and/or has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
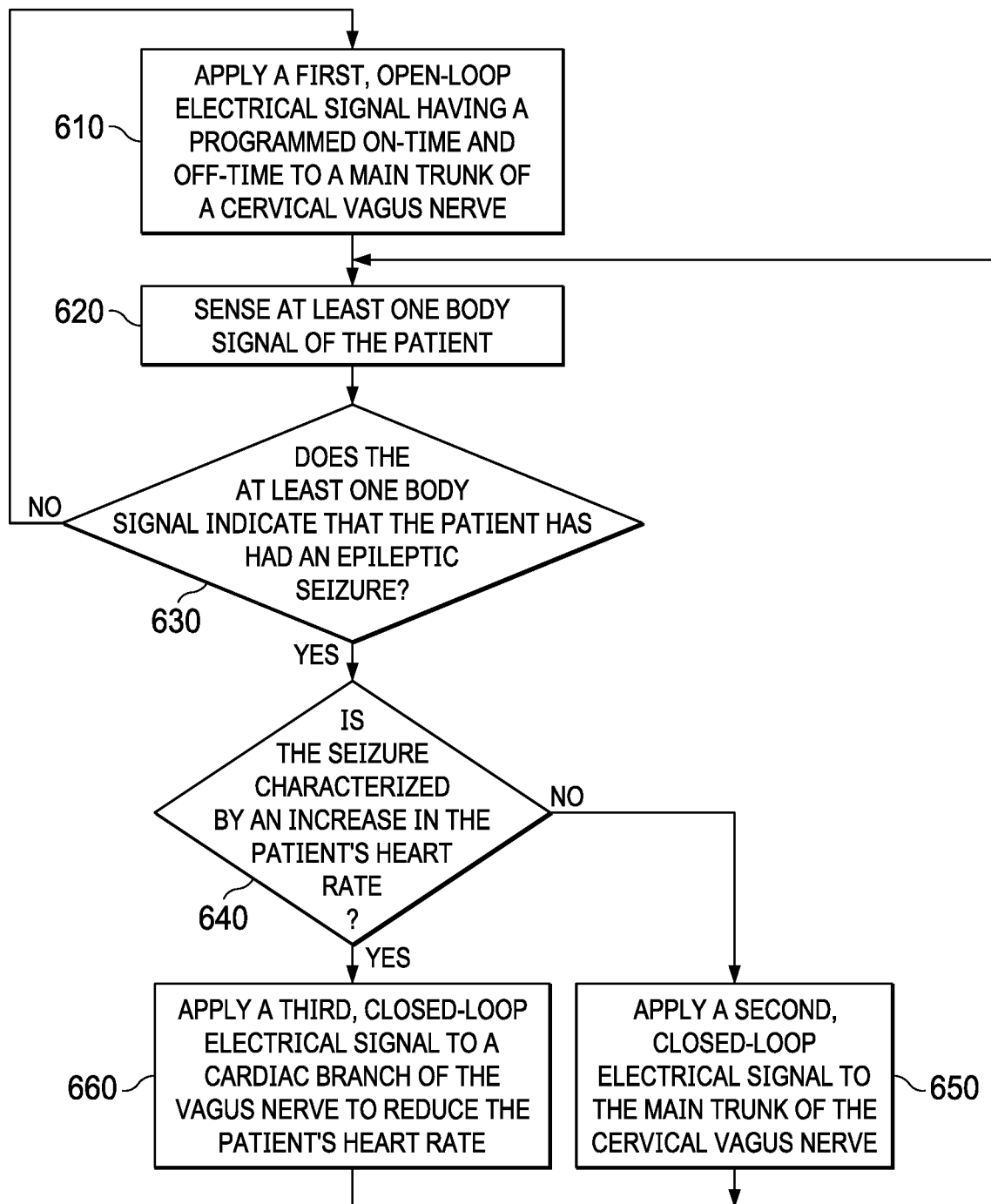
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present disclosure.

FIG. 6 is a flow diagram of a further method of treating a patient having epilepsy according to the present disclosure. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient is having and/or has had an epileptic seizure (630). If the patient is not having and/or has not had a seizure, the method continues applying the first, open-loop electrical signal to a main trunk of a vagus nerve (610). If the patient is having and/or has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the disclosure, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
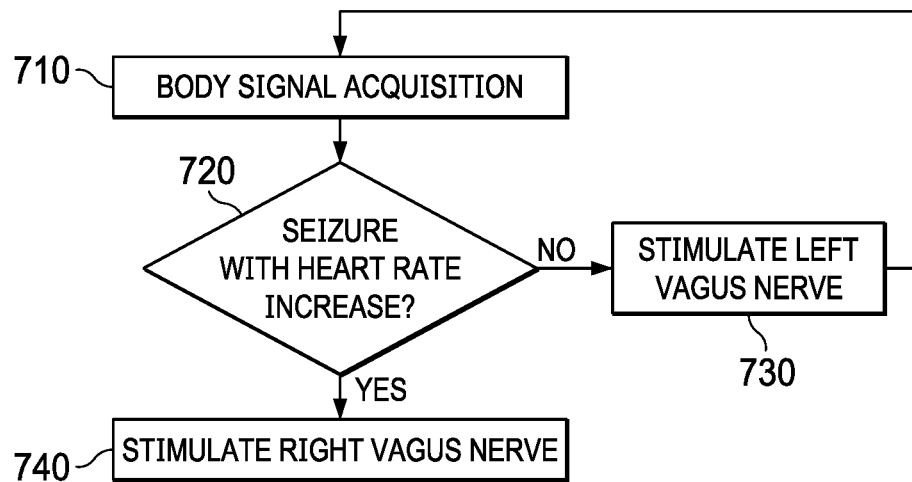
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection. For example if a recumbent person's heart rate is 55 bpm and it increases to 85 during a seizure, this is not clinical/pathological tachycardia, but may be considered tachycardia within the meaning of some embodiments of the present disclosure.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient is having and/or has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient is having and/or has had a seizure.

The method also comprises determining (720) whether or not the seizure is accompanied by an increase in heart rate. In one embodiment, the body data signal comprises a heart beat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961,618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient is having and/or has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present disclosure takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the disclosure, electrode pairs may be applied to each of the left and right vagus nerves of the patient, and used depending upon whether or not seizures accompanied by cardiac changes such as tachycardia are detected.

Figure 8:
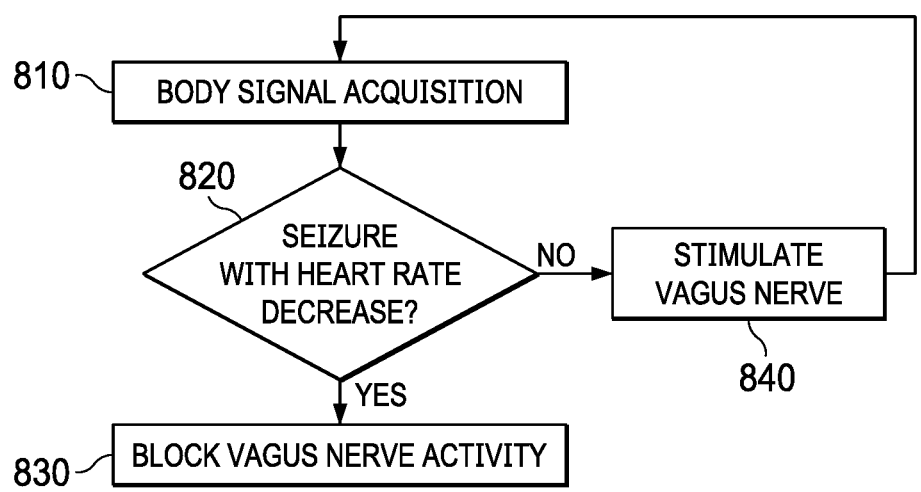
FIG. 8 is a flowchart depiction of a method for providing a closed-loop therapy to a vagus nerve of a patient with epilepsy in response to detecting a seizure associated with a heart rate decrease, wherein said therapy blocks impulse conduction along at least one vagus nerve.

FIG. 8 is a flowchart depiction of a method of treating patients having seizures accompanied by a relative or absolute decrease in heart rate (i.e., a bradycardia episode). Epileptic seizures originating from certain brain regions may trigger decreases in heart rate of a magnitude sufficient to cause loss of consciousness and of postural tone (i.e., syncope). In some subjects the cerebral ischemia associated with the bradycardia may in turn lead to convulsions (i.e., convulsive syncope). If bradycardia-inducing seizures are not controllable by medications, the current treatment is implantation of a demand cardiac pacemaker. In one embodiment of the present disclosure, ictal bradycardia may be treated by preventing vagal nerve impulses from reaching the heart, either by preventing impulses traveling through all fiber types contained in the trunk of the nerve or in one of its branches, or by only blocking impulses within a certain fiber type. In another embodiment, the degree of the nerve impulse blocking within a vagus nerve may be determined based upon the magnitude of bradycardia (e.g., the larger the bradycardia change from the pre-existing baseline heart rate, the larger the magnitude of the block) so as to prevent tachycardia from occurring.

In one embodiment, a body signal is acquired (810). The body signal may comprise one or more body signals that may be altered, changed or influenced by an epileptic seizure. Changes in the body signal may be used to detect the onset or impending onset of seizures. As noted with reference to FIG. 7, the body signal may comprise one or more measure derived from a cardiac signal (e.g., heart rate, heart rate variability, change in EKG morphology), a kinetic signal (e.g., an accelerometer, force of muscle contraction, posture or body position signal), blood pressure, blood oxygen concentration, skin resistivity/conductivity, pupil dilation, eye movement, or other body signals. The body signal may be a real-time signal, a near-real-time signal, or a non-real-time signal, although in preferred embodiments, the signal is a real-time signal or a near-real-time signal. The signal may be acquired from a sensor element (e.g., coupled to a processor) or from a storage device.

Referring again to FIG. 8, the method further comprises determining whether or not the patient is having and/or has had a seizure that is accompanied by a decrease in heart rate (820). In one embodiment, the method comprises using a seizure detection algorithm using one or more of a cardiac, kinetic, neurologic, endocrine, metabolic or tissue stress marker to detect seizures, and to determine if the seizure is associated with a decrease in heart rate. In a particular embodiment, an algorithm-which may comprise software and/or firmware running in a processor in a medical device-analyzes one or more of a cardiac signal, a kinetic signal, blood pressure, blood oxygen concentration, skin resistivity or conductivity, pupil dilation, and eye movement to identify changes in the one or more signals that indicate the occurrence of an epileptic seizure. Such changes may be identified by determining one or more indices from the foregoing signals, such as a cardiac index (e.g., a heart rate), a kinetic index (e.g., a kinetic level or motion type, a magnitude of an acceleration or force, or other indices that may be calculated from an accelerometer signal). The method may include providing an output signal or setting a data flag when the detection algorithm determines from the body signal(s) that the patient is having and/or has had a seizure. In a preferred embodiment, the seizure detection occurs in real time and the output signal or data flag is set immediately upon detection of the seizure.

Once it is determined that the patient is having and/or has had a seizure, the method also comprises determining if the seizure is accompanied by a decrease in heart rate. In one embodiment, the acquired body data signal (810) comprises a heart beat signal that may be analyzed to determine heart rate. In some embodiments, the acquired heart beat signal may be used by the seizure detection algorithm to determine whether a seizure has occurred, while in other embodiments seizures are determined without regard to the patient's heart rate. Regardless of how the seizure is determined, the method of FIG. 8 comprises determining whether a detected seizure event is accompanied by a decrease in heart rate (820). The decrease in heart rate may be determined in a variety of ways, such as by a decrease in an instantaneous heart rate below a reference heart rate value (which may be a predetermined interictal value such as 72 beats per minute (bpm), or a real-time measure of central tendency for a time window or number-of-beats window (e.g., a 5 minute median or moving average heart rate, or a media heart rate for a window selected from 3-300 beats such as a 5, 10, or 300 beat window)). Additional details about identifying decreases in heart rate in the context of epileptic seizures are provided in U.S. patent application Ser. Nos. 12/770,562, 12/771,727, 12/771,783, 12/884,051, 12/886,419, 13/091, 033, each of which is hereby incorporated by reference in its entirety herein.

In one embodiment, if the acquired body data signal does not indicate that the patient is having and/or has had a seizure accompanied by a HR decrease, the method comprises applying a first electrical signal to a vagus nerve (840), wherein the first electrical signal is sufficient to generate exogenous action potentials in fibers of the vagus nerve. The second electrical signal is a therapeutic electrical signal to treat the seizure. It may be applied to either the left or right vagus nerves, or both. The first electrical signal may be a signal defined by, among other parameters, an on-time during which electrical pulses are applied to the nerve, and an off-time during which no pulses are applied to the nerve. In some embodiments, the on-time may be determined by the duration and intensity of the change in heart rate, while in other embodiments it may be pre-programmed. Cathode(s) and anode(s) may be placed on the nerve trunks or branches to maximize flow of exogenously generated nerve impulses in a caudal direction (for control of heart rate changes) and a cephalic direction for seizure treatment.

If the body signal indicates that the patient is having and/or has had a seizure accompanied by a decrease in heart rate, the method comprises applying an action to decrease vagal/parasympathetic tone. In one embodiment, the method comprises blocking the passage of impulses through at least one of a vagus nerve trunk or branch. This may be accomplished by applying one or more of a second electrical signal (e.g., a high frequency electrical signal), a thermal signal (e.g., cooling), a chemical signal (e.g., applying a local anesthetic), and/or a mechanical signal (e.g., applying pressure or a vibration) to a vagus nerve of the patient (830). In another embodiment, the method comprises delivering at least one of an anti-cholinergic drug or a sympatho-mimetic drug.

As used herein, blocking vagus nerve activity means blocking intrinsic or native vagal activity (i.e., blocking action potentials not artificially or exogenously induced by an electrical signal generated by a device). The blocking signal may block the conduction of action potentials in all or at least some portion or fraction of the axons of a vagus nerve. In general, such blocking signals are incapable of inducing exogenous action potentials in the axons of the vagus nerve. In one embodiment, the blocking signal may comprise a high frequency, pulsed electrical signal, the pulse frequency being sufficient to inhibit propagation of at least some action potentials in vagus nerve fibers. The electrical signal may comprise a signal in excess of 300 Hz, or other frequency, so long as the frequency and other stimulation signal parameters (such as pulse width and pulse current or voltage) provide a signal capable of inhibiting some or all of the action potentials propagating along fibers of the vagus nerve. In alternative embodiments, the electrical signal may comprise generating unidirectional action potentials for collision blocking of endogenous action potentials.

High frequency vagus nerve stimulation (or other blocking signals such as collision blocking) may inhibit pathological vagus nerve activity associated with the seizure that may be acting to slow the patient's heart rate. By providing such stimulation only when the patient experiences a seizure accompanied by a reduced heart rate (e.g., bradycardia), a therapy may be provided that acts to maintain the patient's heart rate when the patient experiences a seizure involving excessive vagal activity—and consequent undesired slowing of—the heart. In one embodiment, the blocking electrical signal (830) is provided to a right vagus nerve. Without being bound by theory, because the right vagus nerve innervates the right sinoatrial node that functions as the heart's natural pacemaker, it is believed that right-side VNS will have a more significant effect upon the heart rate than stimulation of the left vagus nerve. In alternative embodiments, the blocking signal may be applied to the left vagus nerve, to both the right and left vagus nerves, or to one or both of the left and right cardiac branches of the vagus nerves.

In one embodiment, the method comprises applying a first electrical signal that may be a conventional vagus nerve stimulation signal defined by a plurality of parameters (e.g., a pulse width, a current magnitude, a pulse frequency, an on-time and an off-time). A seizure detection algorithm (e.g., using one or more of a cardiac, kinetic, metabolic, EEG, or other body signal) may be used to detect seizures, and the patient's heart rate may be determined proximate the seizure detection to determine if the seizure is accompanied by a decrease in the patient's heart rate. If the seizure is accompanied by a slowing of the patient's heart rate, the first electrical signal may be suspended, and a second electrical signal may be applied to slow the patient's heart rate. The method may further include sensing the patient's heart rate during or after application of the second electrical signal. In one embodiment, the second electrical signal may be modified (e.g., by changing current magnitude, pulse width, or pulse frequency), or suspended (and possibly resumed) to maintain the patient's heart rate between an upper heart rate threshold and a lower heart rate threshold. In some embodiments, the upper and lower heart rate thresholds may be dynamically set (e.g., as no more than 5 bpm above or below the baseline HR prior to the seizure detection).

Figure 9:
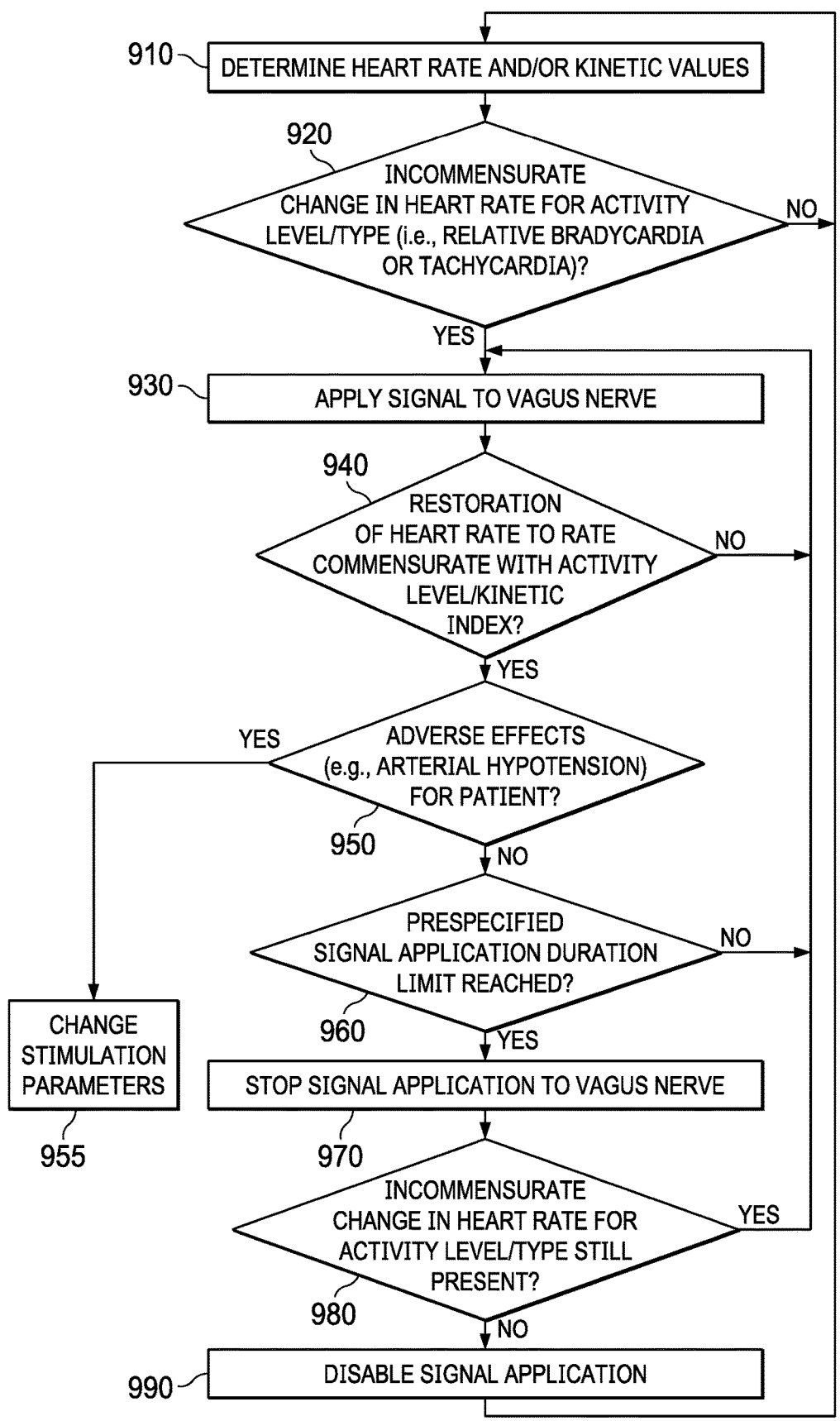
FIG. 9 is a flowchart depicting a method for providing closed-loop vagus nerve stimulation based on an assessment of whether the patient's heart rate is commensurate with the patient's activity level or activity type.

FIG. 9 is a flow diagram of a method of treating a patient with epilepsy by providing closed-loop vagus nerve intervention (e.g., stimulation or blockage of impulse conduction) to maintain the patient's heart rate within a range that is both safe and also commensurate with the activity type or level and state of the patient (e.g., as determined from a kinetic signal from a sensing element such as a triaxial accelerometer or by measuring oxygen consumption). In one embodiment, the method comprises providing vagus nerve stimulation in response to determining that a heart rate is incommensurate with the kinetic signal of the patient, to restore cardiac function to a rate that is commensurate with the patient's kinetic signal. In one embodiment, the stimulation may comprise stimulating a right vagus nerve to slow the patient's heart rate to a level that is safe and/or commensurate with activity level. In another embodiment, the stimulation may comprise providing a blocking signal to increase a slow heart rate to a rate that is safe and/or commensurate with the activity level. Pharmacologic compounds (e.g., drugs) with sympathetic or parasympathetic effects (e.g., enhancing or blocking sympathetic or parasympathetic activity) may be used to restore heart rate to a rate commensurate with kinetic activity of the patient in still other embodiments. In one embodiment, the method involves determining a heart rate and one or more kinetic or metabolic (e.g., oxygen consumption) indices for the patient (910). Heart rate may be determined from an acquired cardiac signal (e.g., from a sensor or stored data). Kinetic and/or metabolic indices may likewise be determined from a kinetic sensor (e.g., an accelerometer, a positional sensor, a GPS device coupled to a clock, or a postural sensor), a metabolic sensor, or from stored data. Sensor data may be subjected to one or more operations such as amplifying, filtering, A/D conversion, and/or other pre-processing and processing operations to enable determination of heart rate (and in some embodiments other cardiac indices such as heart rate variability) and kinetic indices.

The activity level of the patient may be determined from multiple kinetic indications such as an activity level, a type of activity, a posture, a body position, a trunk or limb acceleration or force, or a duration of one of the foregoing, and may be adapted or modified as a function of age, gender, body mass index, fitness level or time of day or other indices of the patient's condition or environment. For example, the kinetic signal may be processed to provide indices that indicate moderate ambulatory motion for an upright patient, vigorous physical exercise (in which the patient may be upright as in running or in a prone position as in some calisthenics exercises), a fall (e.g., associated with a seizure), reclining, resting or sleeping, among other activity levels and kinetic states.

The one or more kinetic indices may then be used to determine (e.g., by retrieving stored data from a lookup table or by calculation using an algorithm) one or more heart rate ranges or values that would be commensurate with the kinetic activity and/or kinetic state, duration, time of day, etc. associated with the indices. In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

Returning to FIG. 9, the determined heart rate may be compared to the range(s)/value(s) identified as commensurate with the kinetic indices (920) at a given time point. If the actual heart rate of the patient is within the expected/commensurate range or value associated with the kinetic or metabolic indices at the time point, or is within a specified proximity of a particular range or value, no action may be taken, and the method may involve continuing to analyze the patient's cardiac and kinetic signals or metabolic signals. On the other hand, if the heart rate is outside the expected value or range of values for the kinetic or metabolic indices for that time point, then the heart rate is not commensurate with the kinetic signal of the patient, and a therapy may be provided to the patient by applying one of an electrical, thermal, mechanical or chemical signal to a vagus nerve of the patient (930) or administering to the patient (e.g., intravenously, through mucosae) a drug with cholinergic or anti-cholinergic or adrenergic actions, depending on the case or situation. In one embodiment, the method may comprise applying the signal to a main trunk of a vagus nerve of the patient, and in another embodiment, the signal may be applied to a cardiac branch of a vagus nerve.

In one embodiment, the heart rate of the patient may be higher than a value commensurate with the activity level or kinetic indices of the patient. In this case, the patient is having relative tachycardia. Where this is the case, as previously noted, vagus nerve stimulation may be applied to one or more of a right cardiac branch, left cardiac branch, or right main trunk of the patient's vagus nerve to reduce the patient's heart rate to a rate that is commensurate with the activity level. Embodiments of the disclosure may be used to treat epileptic seizures associated with tachycardia, and other medical conditions associated with tachycardia given the patient's activity level. Therapies (e.g., electrical, chemical, mechanical, thermal) delivered to a patient via the vagus nerves may be employed for tachyarrythmias, angina pectoris or pain in regions innervated by a vagus nerve.

In another embodiment, the patient's heart rate may be lower than a value commensurate with the patient's activity level or kinetic indices, that is, the patient is having relative or absolute bradycardia. High frequency (>>300 Hz) electrical pulses may be applied to the left or right vagus nerves (e.g., a main trunk of the right and/or left vagus nerves or to their cardiac branches) to block propagation of transmission of nerve impulses through their fibers. High-frequency VNS may be applied to block impulses traveling to the heart to abate neurogenic, cardiogenic or iatrogenic bradycardia, or to minimize the cumulative effects on the heart's conduction system and myocardium of epileptic seizures, especially in status epilepticus. Selective blockage of impulses traveling through a vagus nerve to the heart may be accomplished with electrical stimulation to treat adverse cardiac effects associated with disorders such as epilepsy, depression, diabetes or obesity. By blocking vagus nerve conduction to the heart, when the patient's heart rate is incommensurate with the activity level or kinetic indices, a therapy may be provided to revert the change in heart rate (whether the change involves bradycardia or tachycardia). In one embodiment, an electrical signal generator may be used to apply a first therapy signal to a vagus nerve of the patient, and an electrical signal generator (which may be the same or a different electrical signal generator) may apply a vagus nerve conduction blocking electrical signal to a vagus nerve (e.g., a cardiac branch of the vagus nerve) to block cardiac effects that would result from the first electrical signal, absent the vagus nerve conduction blocking electrical signal.

Referring again to FIG. 9, the method may comprise determining the patient's heart rate in response the therapy to determine whether the heart rate has been restored to a rate that is with commensurate with the patient's activity level/kinetic index (940). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (950). Adverse events may include, without limitation, side effects such as voice alteration, pain, difficulty breathing or other respiratory effects, adverse cardiac effects such as bradycardia (following a determination of relative tachycardia in step 920), tachycardia (following a determination of bradycardia in step 920), and alteration in blood pressure or gastro-intestinal activity.

If an adverse event has occurred, the method may involve changing one or more stimulation parameters to eliminate, reduce or ameliorate the adverse event (955). If no adverse event has occurred, the method may comprise continuing to apply a signal the vagus nerve until a predetermined signal application duration has been reached (960), at which time the signal application may be stopped (970). The method may further comprise determining, after the therapy has been stopped, if the patient's heart rate remains incommensurate with the patient's activity level or type (980), in which case the signal application may be resumed or other appropriate action may be taken (e.g., local or remote alarms or alerts, notification of caregivers/healthcare providers, etc.). If the heart rate has returned to a value that is commensurate or appropriate for the patient's activity level, the signal application may be discontinued (990).

Figure 10:
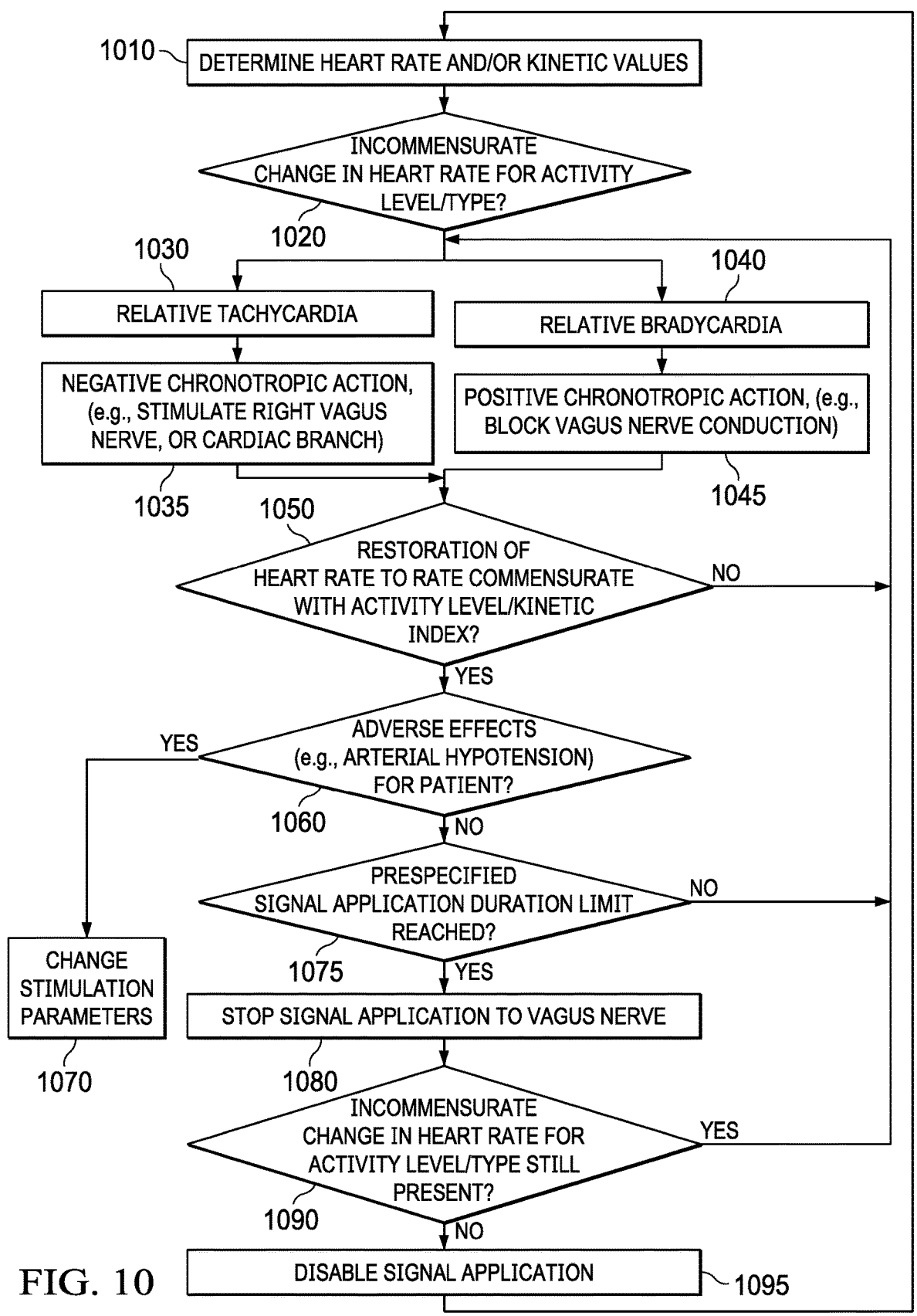
FIG. 10 is a flowchart depicting a method for providing closed-loop vagus nerve stimulation based on a determination that the patient's heart rate is incommensurate with the patient's activity level or activity type, and further in view of whether the incommensurate changes involves relative tachycardia or relative bradycardia.

FIG. 10 is a flow diagram of a method of treating a patient to with epilepsy by providing closed-loop vagus nerve stimulation to treat relative tachycardia or relative bradycardia by restoring the patient's heart rate to a rate that is commensurate with the activity type or level of the patient (e.g., as determined from a kinetic signal from a sensing element such as a triaxial accelerometer or by measuring oxygen consumption). In one embodiment, the method comprises identifying instances of relative tachycardia or relative bradycardia and responding with negative or positive chronotropic actions to restore the heart rate to a level commensurate with the patient's activity type or level.

In one embodiment, the method involves determining a heart rate and an activity type or level for the patient (1010). The patient's heart rate may be determined from an acquired cardiac signal or from stored data. The activity level or type of the patient may be determined from one or more sensor or from stored data. Sensors may include, for example, accelerometers, positional sensors, GPS devices coupled to a clock, postural sensors, and metabolic sensors. Sensor data may be subject to conventional signal processing, and may in addition be adapted or modified as a function of age, gender, body mass index, fitness level or time of day or other indices of the patient's condition or environment.

The patient's activity type or level may then be used to determine one or more heart rate ranges or values that are commensurate with the activity type or level (1020). In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

If the heart rate is commensurate with the activity level, in one embodiment no action may be taken, and the method may involve continuing to analyze the patient's cardiac and activity. On the other hand, if the heart rate is outside the identified value or range of values appropriate for the patient's activity type or level then the heart rate is not commensurate with the kinetic signal of the patient. Where this is the case, the method may further comprise determining whether the patient is experiencing relative tachycardia or is experiencing relative bradycardia (1030, 1040).

Where the heart rate of the patient is higher than a value commensurate with the activity level or type, the patient is experiencing relative tachycardia (1030), and the method may comprise initiating a negative chronotropic action (1035) to slow the heart rate to a rate that is commensurate with the activity level or type. In one embodiment, this may involve applying stimulation to one or more of a left or right main vagal trunk or cardiac branch of the patient. In other embodiments, the method may comprise providing a drug to enhance the parasympathetic tone of the patient. In still other embodiments, the method may comprise reducing the patient's sympathetic tone, such as by applying high-frequency stimulation to a sympathetic nerve trunk or ganglion or administering an anti-cholinergic drug. Negative chronotropic actions may be used to treat epileptic seizures associated with tachycardia, and other medical conditions associated with relative tachycardia given the patient's activity level.

Where the heart rate of the patient is lower than a value commensurate with the activity level or type, the patient is experiencing relative bradycardia (1040), and the method may comprise initiating a positive chronotropic action (1045) to increase the heart rate to a rate that is commensurate with the activity level or type. In one embodiment, this may involve applying high-frequency (>>300 Hz) electrical stimulation to one or more of a left or right main vagal trunk or cardiac branch of the patient to reduce the transmission of intrinsic vagus nerve action potentials in at least some vagal fibers. In other embodiments, the method may comprise providing a drug to reduce the parasympathetic tone of the patient. In still other embodiments, the method may comprise increasing the patient's sympathetic tone, such as by applying electrical signals to a sympathetic nerve trunk or ganglion or by administering a sympatho-mimetic drug. Positive chronotropic actions may be used to treat epileptic seizures associated with bradycardia, and other medical conditions associated with relative bradycardia given the patient's activity level.

The method may further comprise, after initiating the negative or positive chronotropic action, determining whether the patient's heart rate has been restored to a rate that is with commensurate with the patient's activity level/kinetic index (1050). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (1060). Adverse events may include, without limitation, side effects such as voice alteration, pain, difficulty breathing or other respiratory effects, adverse cardiac effects such as bradycardia (following a determination of relative tachycardia in step 1030), or tachycardia (following a determination of bradycardia in step 1040), and alteration in blood pressure or gastric activity.

If an adverse event has occurred, the method may involve changing one or more stimulation parameters to eliminate, reduce or ameliorate the adverse event (1070). If no adverse event has occurred, the method may comprise continuing to stimulate the vagus nerve (or a chemical, thermal or mechanical therapy) until a predetermined stimulation duration has been reached (1075), at which time the stimulation may be stopped (1080). The method may further comprise determining, after the therapy has been stopped, if the patient's heart rate remains incommensurate with the patient's activity level or type (1090), in which case the stimulation may be resumed or other appropriate action may be taken (e.g., local or remote alarms or alerts, notification of caregivers/healthcare providers, use of other forms of therapy, etc.). If the heart rate has returned to a value that is commensurate or appropriate for the patient's activity level, the stimulation may be discontinued (1095).

Additional embodiments consistent with the foregoing description and figures may be made. Non-limiting examples of some such embodiments are provided in the numbered paragraphs below.

100. A method of controlling a heart rate of an epilepsy patient comprising:
 sensing at least one of a kinetic signal and a metabolic signal of the patient;
 analyzing the at least one of a kinetic and a metabolic signal to determine at least one of a kinetic index and a metabolic index;
 receiving a cardiac signal of the patient;
 analyzing the cardiac signal to determine the patient's heart rate;
 determining if the patient's heart rate is commensurate with the at least one of a kinetic index and a metabolic index; and
 applying an electrical signal to a vagus nerve of the patient based on a determination that the patient's heart rate is not commensurate with the at least one of a kinetic signal and a metabolic signal of the patient.

101. The method of numbered paragraph 100, wherein determining at least one of a kinetic index and a metabolic index comprises determining at least one of an activity level or an activity type of the patient based on the at least one of a kinetic index and a metabolic index, and wherein determining if the patient's heart rate is commensurate with the at least one of a kinetic index and a metabolic index of the patient comprises determining if the heart rate is commensurate with the at least one of an activity level or an activity type.

102. The method of numbered paragraph 101, wherein determining if the patient's heart rate is commensurate with the at least one of a kinetic index and a metabolic index comprises determining if the patient's heart rate is above or below a rate that is commensurate with the one or more of a kinetic index and a metabolic index.

103. A method of treating a patient having epilepsy comprising
 sensing at least one body signal of the patient;
 determining whether or not the patient is having or has had an epileptic seizure based on the at least one body signal;
 sensing a cardiac signal of the patient;
 determining whether or not the seizure is associated with a change in the patient's cardiac signal;
 applying a first therapy to a vagus nerve of the patient based on a determination that the patient is having or has had an epileptic seizure that is not associated with a change in the patient's cardiac signal, wherein the first therapy is selected from an electrical, chemical, mechanical, or thermal signal; and
 applying a second therapy to a vagus nerve of the patient based on a determination that the patient is having or has had an epileptic seizure associated with a change in the patient's cardiac signal, wherein the second therapy is selected from an electrical, chemical, mechanical (e.g., pressure) or thermal signal.

104. The method of numbered paragraph 103, further comprising
 applying a third therapy to a vagus nerve of the patient based a determination that the patient is not having or has not had an epileptic seizure, wherein the third therapy is selected from an electrical, chemical, mechanical or thermal signal.

105. A method of treating a patient having epilepsy comprising:
 coupling a first set of electrodes to a main trunk of the left vagus nerve of the patient;
 coupling a second set of electrodes to a main trunk of the right vagus nerve of the patient;
 providing an electrical signal generator coupled to the first electrode set and the second electrode set;
 receiving at least one body data stream;
 analyzing the at least one body data stream using a seizure detection algorithm to determine whether or not the patient is having and/or has had an epileptic seizure;
 applying a first electrical signal from the electrical signal generator to the main trunk of the left vagus nerve, based on a determination that the patient is having and/or has had an epileptic seizure without a heart rate change; and applying a second electrical signal from the electrical signal generator to the main trunk of the right vagus nerve, based on a determination that the patient is having or has had an epileptic seizure with a heart rate change.

106. A method of treating a patient having epilepsy comprising:

receiving at least one body data stream;

analyzing the at least one body data stream using a seizure detection algorithm to detect whether or not the patient has had an epileptic seizure;

receiving a cardiac signal of the patient;

analyzing the cardiac signal to determine a first cardiac feature;

applying a first electrical signal to a vagus nerve of the patient, based on a determination that the patient has not had an epileptic seizure characterized by a change in the first cardiac feature, wherein the first electrical signal is not a vagus nerve conduction blocking electrical signal; and applying a second electrical signal to a vagus nerve of the patient, based on a determination that the patient has had an epileptic seizure characterized by a change in the cardiac feature, wherein the second electrical signal is a pulsed electrical signal that blocks action potential conduction in the vagus nerve.

107. A method of treating a patient having epilepsy comprising:

receiving at least one body data stream;

analyzing the at least one body data stream using a seizure detection algorithm to detect whether or not the patient has had an epileptic seizure;

receiving a cardiac signal of the patient;

analyzing the cardiac signal to determine a first cardiac feature;

applying a first electrical signal to a vagus nerve of the patient, based on a determination that the patient has not had an epileptic seizure characterized by a change in the first cardiac feature, wherein the first electrical signal is a pulsed electrical signal that blocks action potential conduction in the vagus nerve; and applying a second electrical signal to a vagus nerve of the patient, based on a determination that the patient has had an epileptic seizure characterized by a change in the cardiac feature, wherein the second electrical signal is not a vagus nerve conduction blocking electrical signal.

Figure 11:
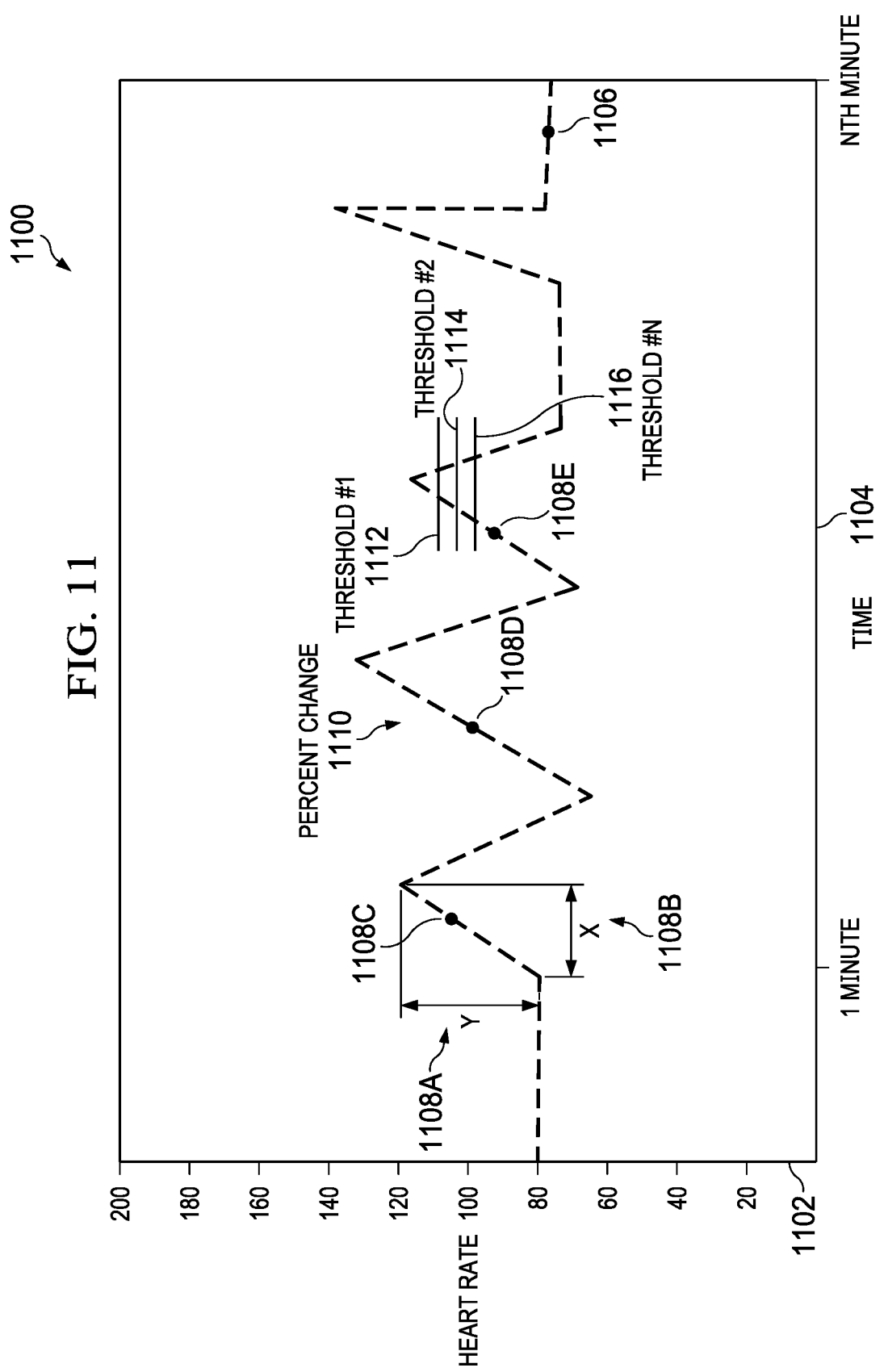
FIG. 11 is a graph of heart rate versus time, according to one embodiment.

In FIG. 11, a graph of heart rate versus time is shown, according to one embodiment. A first graph 1100 includes a y-axis 1102 which represents heart rate where the heart rate goes from a zero value to an Nth value (e.g., 200 heart beats, etc.). Further, the first graph 1100 includes an x-axis 1104 which represents time from 1 minute to Nth minutes (and/or 0.001 seconds to Nth seconds). In this example, a first heart rate versus time line 1106 for the patient is shown. In this example, the patient's heart rate goes from 80 heart beats per minute to 118 heart beats per minute with a first rise 1108A and a first run 1108B during a first event 1108C. In addition, the patient's heart rate goes from 70 heart beats per minute to 122 heart beats per minute during a second event 1108D which has a first percentage change 1110 associated with the second event 1108D. Further, the patient's heart rate goes from 70 beats per minute to 113 beats per minute during an nth event 1108E which surpasses a first threshold amount 1112, and/or a second threshold amount 1114, and/or an Nth threshold amount 1116. In one example, only the Nth threshold amount 1116 needs to be reached to trigger a therapy and/or an alert. In another example, only the second threshold amount 1114 needs to be reached to trigger a therapy and/or an alert. In another example, only the first threshold 1112 needs to be reached to trigger a therapy and/or an alert. In another example, both the Nth threshold 1116 and the second threshold 1114 need to reached to trigger a therapy and/or an alert. In another example, all of the Nth threshold 1116, the second threshold 1114 and the first threshold 1112 need to reached to trigger a therapy and/or an alert. In one example, only the Nth threshold amount 1116 needs to be reached during a specific time period to trigger a therapy and/or an alert. In another example, only the second threshold amount 1114 needs to be reached during a specific time period to trigger a therapy and/or an alert. In another example, only the first threshold 1112 needs to be reached during a specific time period to trigger a therapy and/or an alert. In another example, both the Nth threshold 1116 and the second threshold 1114 need to reached during a specific time period to trigger a therapy and/or an alert. In another example, all of the Nth threshold 1116, the second threshold 1114 and the first threshold 1112 need to reached during a specific time period to trigger a therapy and/or an alert. In these examples, one or more triggering events may occur based on a determination of the rise and run of a change in heart rate, a percentage change in heart rate, a threshold amount being reached or exceeded (or within any percentage of the threshold), and/or any combination thereof. A triggering event may initiate one or more actions to increase and/or decrease the patient's heart rate. For example, if the patient's heart rate is increasing which determines the triggering event, then the system, device, and/or method may initiate one or more actions to decrease the heart rate of the patient to help reduce, dampen, eliminate, and/or buffer the increase in the patient's heart rate. Further, the system, device, and/or method may oscillate between decreasing the patient's heart rate and increasing the patient's heart rate depending on any changes to the patient's heart rate. For example, the system, device, and/or method may initiate one or more actions to decrease a patient's heart rate based on the patient's heart rate going from 80 heart beats per minute to 130 heart beats per minute which results in the patient's heart rate falling from 130 heart beats per minute to 65 heart beats per minute in a first time period. Based on the change in the heart rate from 130 heart beats per minute to 65 heart beats per minute in the first time period, the system, device, and/or method may initiate one or more actions to increase the patient's heart rate and/or stabilize the patient's heart rate. In another example, the system, method, and/or device may stop and/or modify any initiated action based on one or more feedback signals. In addition, one or more warnings may be transmitted to the patient, a caregiver, a doctor, a medical professional, and/or logged.

Figure 12:
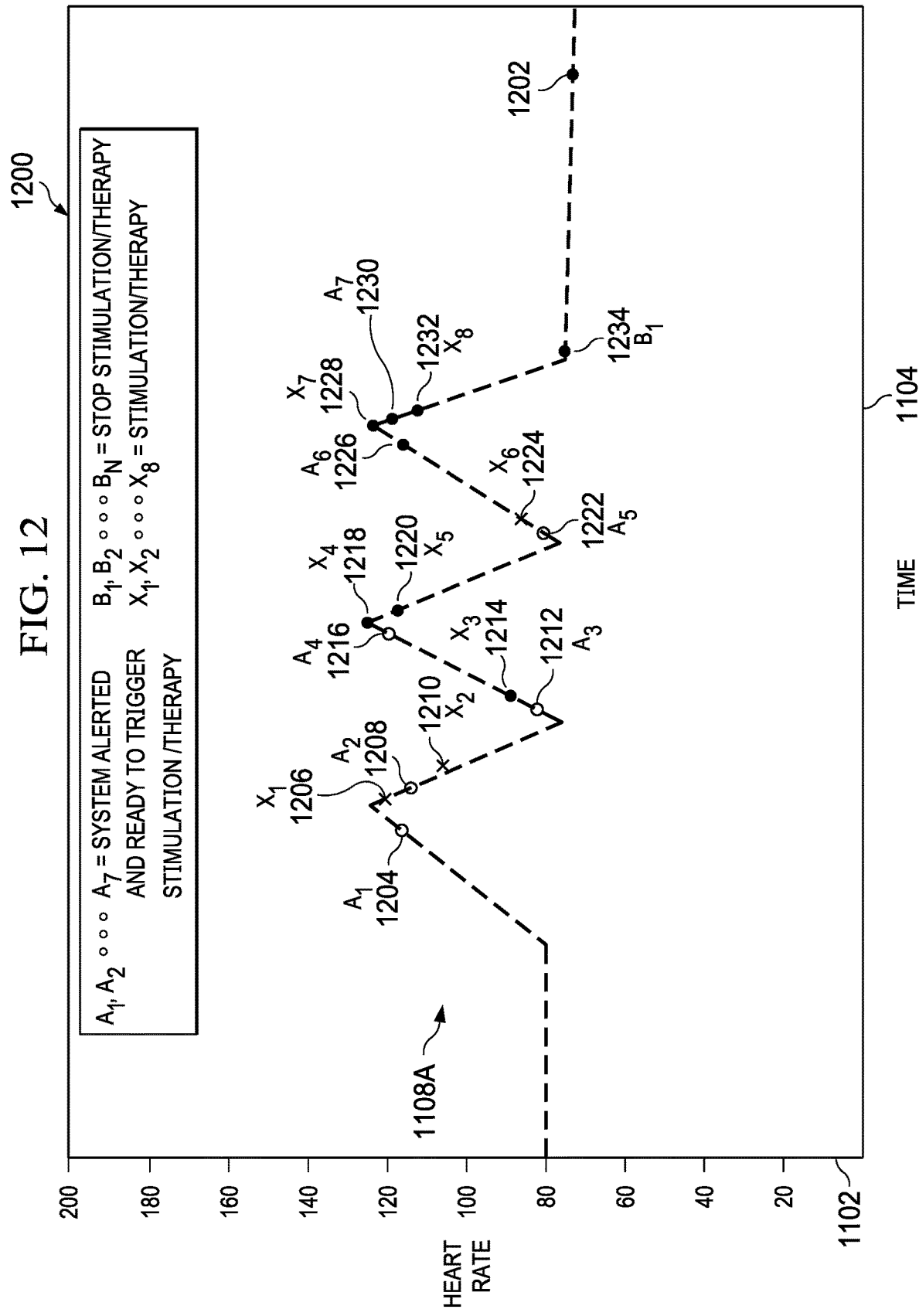
FIG. 12 is another graph of heart rate versus time, according to one embodiment.

In FIG. 12, another graph of heart rate versus time is shown, according to one embodiment. A second graph 1200 illustrating a second heart rate versus time line 1202 for the patient is shown. In this example, the patient's heart rate goes from 80 heart beats per minute to 120 heart beats per minute which creates a first system alert event 1204 (e.g., A1). Further, the system, device, and/or method initiates a first therapy 1206 (e.g., X1) based on the first system alert event 1204. In addition, a second system alert event 1208 (e.g., A2) occurs and a second therapy 1210 (e.g., X2) is initiated based on the second system alert event 1208. In addition, a third system alert event 1212 (e.g., A3) occurs and a third therapy (e.g., X3) 1214 is initiated based on the third system alert event 1212 (e.g., A3). In addition, a fourth system alert event 1216 (e.g., A4) occurs and a fourth therapy 1218 (e.g., X4) is initiated based on the fourth system alert event 1216 (e.g., A3). Further, a fifth therapy 1220 (e.g., X5) is initiated based on the effects of the fourth therapy 1218 (e.g., X4). In addition, a fifth system alert event 1222 (e.g., A5) occurs and a sixth therapy (e.g., X6) 1224 is initiated based on the fifth system alert event 1222 (e.g., A5). In addition, a sixth system alert event 1226 (e.g., A6) occurs and a seventh therapy (e.g., X7) 1228 is initiated based on the sixth system alert event 1226 (e.g., A6). In addition, a seventh system alert event 1230 (e.g., A7) occurs and an eighth therapy (e.g., X8) 1232 is initiated based on the seventh system alert event 1230 (e.g., A7). In addition, a first stop stimulation event 1234 (e.g., B1) occurs which turns off all therapies and/or system alerts may occur when the heart rate returns to the approximate starting heart rate and/or a target value. In these examples shown with FIG. 12, a rise over run heart rate calculation was completed to determine the one or more system alerts. However, it should be noted that any calculation (e.g., % increase, % decrease, etc. can be utilized). Further, all systems alerts and/or therapies may occur as independent events and/or examples. For example, the seventh system alert may be the first system alert in a specific example. In other words, no other events and/or therapies occurred before the seventh system alert. Therefore, the seventh system alert becomes the first system alert. In addition, one or more warnings may be transmitted to the patient, a caregiver, a doctor, a medical professional, and/or logged. In addition, there may be up to an Nth alerts, an Nth stop stimulation (and/or therapy) event, and an Nth therapy in any of the examples disclosed in this document.

Figure 13:
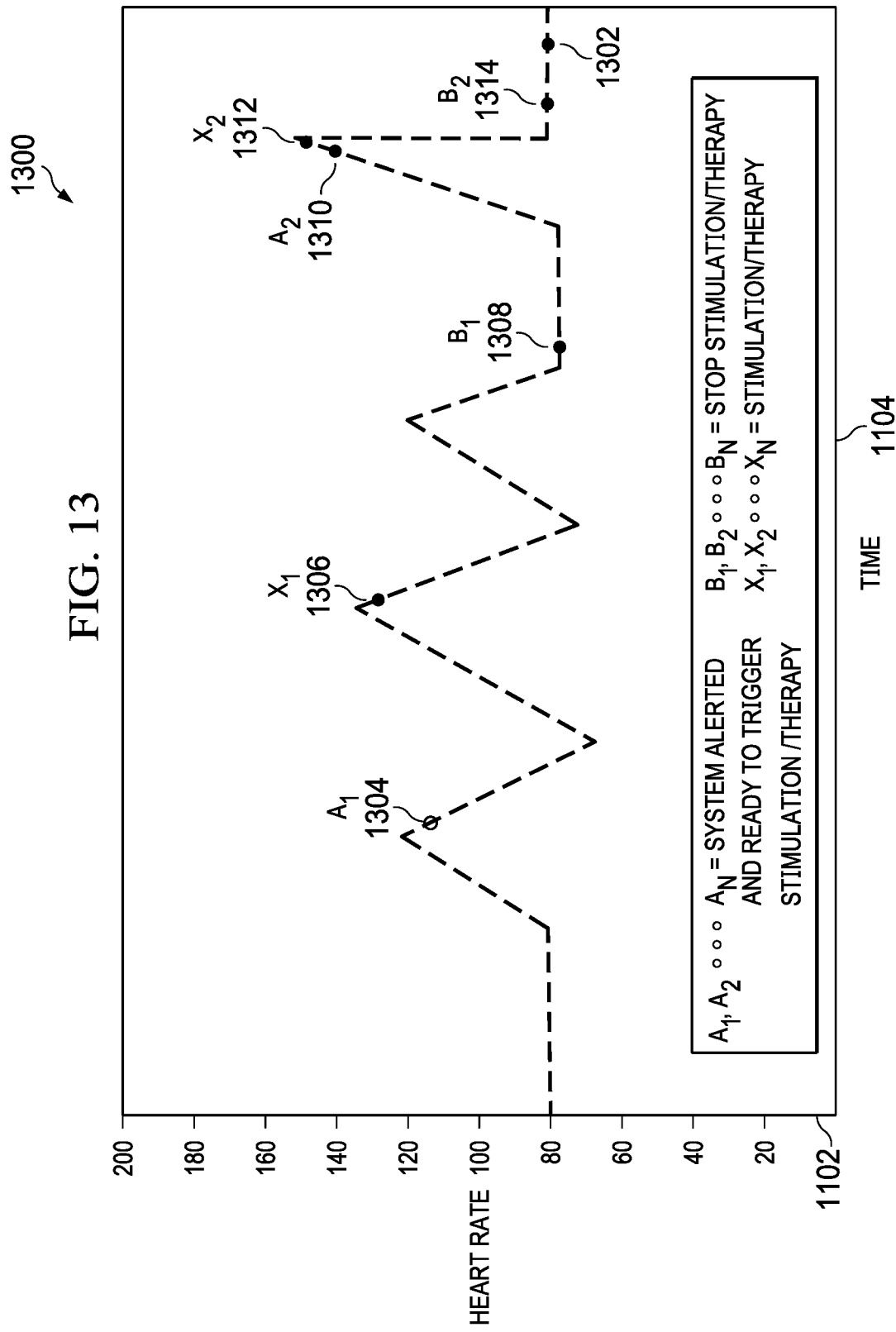
FIG. 13 is another graph of heart rate versus time, according to one embodiment.

In FIG. 13, another graph of heart rate versus time is shown, according to one embodiment. A third graph 1300 illustrating a third heart rate versus time line 1302 for the patient is shown. In this example, the patient's heart rate goes from 80 heart beats per minute to 116 heart beats per minute which creates a first system alert event 1304 (e.g., A1). Further, the system, device, and/or method initiates a first therapy 1306 (e.g., X1) based on the first system alert event 1304. In addition, a first stop stimulation event 1308 (e.g., B1) occurs which turns off all therapies and/or system alerts occurs when the heart rate returns to the approximate starting heart rate and/or a target value. Further, the patient's heart rate goes from 80 heart beats per minute to 123 heart beats per minute which creates a second system alert event 1310 (e.g., A2). Further, the system, device, and/or method initiates a second therapy 1312 (e.g., X2) based on the second system alert event 1310. In addition, a second stop stimulation event 1314 (e.g., B2) occurs which turns off all therapies and/or system alerts occurs when the heart rate returns to the approximate starting heart rate and/or a target value. In these examples shown with FIG. 13, a percentage change in heart rate calculation was completed to determine the one or more system alerts. However, it should be noted that any calculation (e.g., rise over run, etc. can be utilized). Further, all systems alerts and/or therapies may occur as independent events and/or examples. For example, the second system alert may be the first system alert in a specific example. In other words, no other events and/or therapies occurred before the second system alert. Therefore, the second system alert becomes the first system alert. In addition, one or more warnings may be transmitted to the patient, a caregiver, a doctor, a medical professional, and/or logged.

Figure 14:
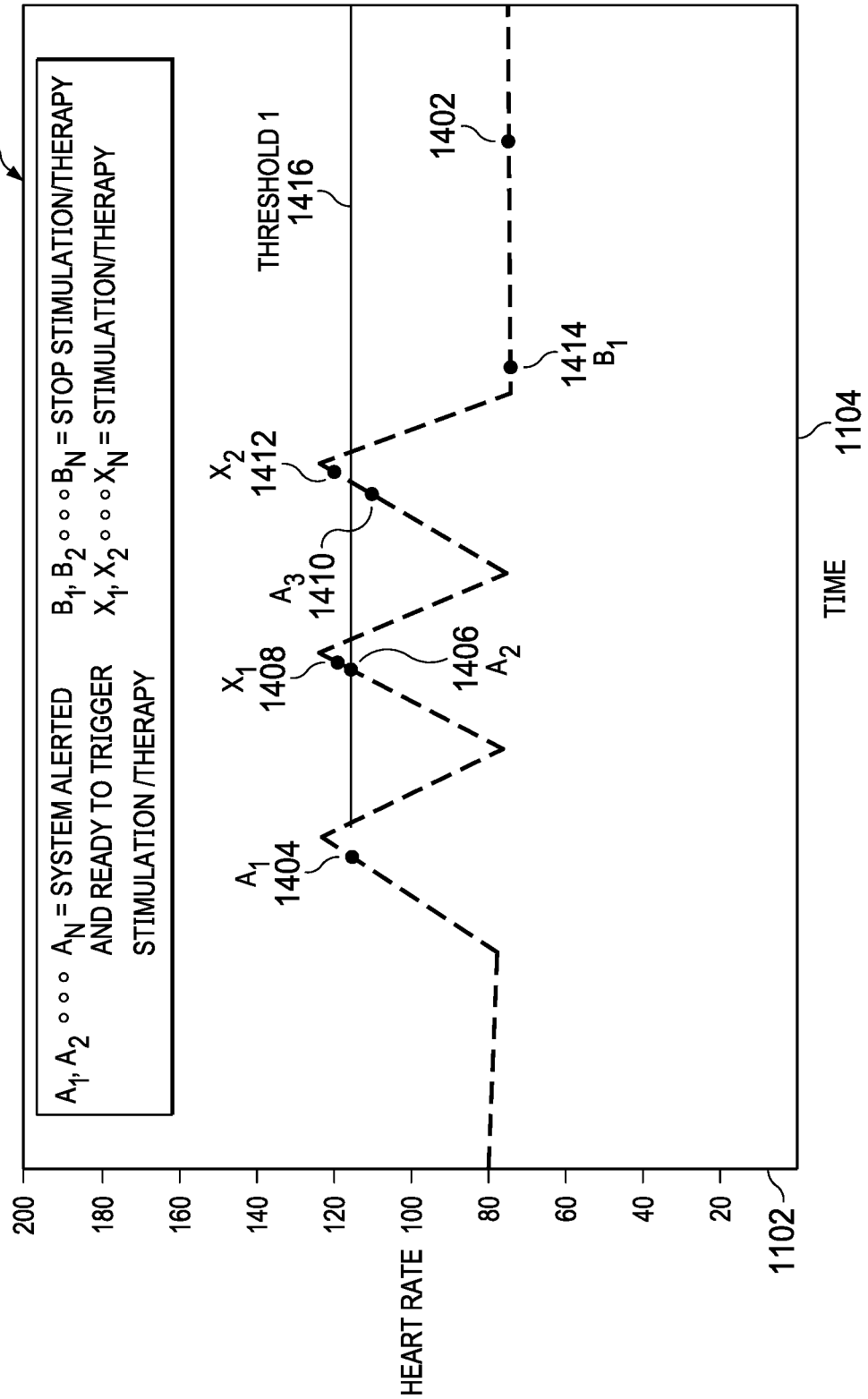
FIG. 14 is another graph of heart rate versus time, according to one embodiment.

In FIG. 14, another graph of heart rate versus time is shown, according to one embodiment. A fourth graph 1400 illustrating a fourth heart rate versus time line 1402 for the patient is shown. In this example, the patient's heart rate goes from 80 heart beats per minute to 120 heart beats per minute which creates a first system alert event 1404 (e.g., A1) because the 120 heart beats per minutes meets or exceeds a first threshold value 1416 (e.g., 115 heart beats per minute). In this example, a second system alert event 1406 (e.g., A2) is created because the heart beats of the patient meets or exceeds the first threshold value 1416 (e.g., 115 heart beats per minute). Further, the system, device, and/or method initiates a first therapy 1408 (e.g., X1) based on the first system alert event 1404 and the second system alert event 1406 occurring. The first system alert event 1404 and the second system alert event 1406 may be time dependent. For example, the first system alert event 1404 and the second system alert event 1406 may have to occur within a first time period for the initiation of the first therapy 1408. In another example, the first system alert event 1404 and the second system alert event 1406 may not be time dependent. Further, a third system alert event 1410 (e.g., A3) is created because the heart beats of the patient meets or exceeds (and/or within a specific rate of the threshold—in this example within 5 percent—heart rate is 110) the first threshold value 1416 (e.g., 115 heart beats per minute). Further, the system, device, and/or method initiates a second therapy 1412 (e.g., X2) based on the first system alert event 1404, the second system alert event 1406, and/or the third system event occurring. It should be noted that the second therapy 1412 has a time delay factor utilized with the second therapy 1412. In another example, no time delay is utilized. In addition, one or more time delays can be used with any therapy, any warning, and/or any alert in this document. The first system alert event 1404, the second system alert event 1406, and the third system alert event 1410 may be time dependent. For example, the first system alert event 1404, the second system alert event 1406, and the third system alert event 1410 may have to occur within a first time period for the initiation of the second therapy 1412. In another example, the first system alert event 1404, the second system alert event 1406, and the third system alert event 1410 may not be time dependent. Further, a first stop stimulation event 1414 (e.g., B1) occurs which turns off all therapies and/or system alerts occurs when the heart rate returns to the approximate starting heart rate and/or a target value. Further, all systems alerts and/or therapies may occur as independent events and/or examples. For example, the third system alert may be the first system alert in a specific example. In other words, no other events and/or therapies occurred before the third system alert. Therefore, the third system alert becomes the first system alert. In addition, one or more warnings may be transmitted to the patient, a caregiver, a doctor, a medical professional, and/or logged.

Figure 15:
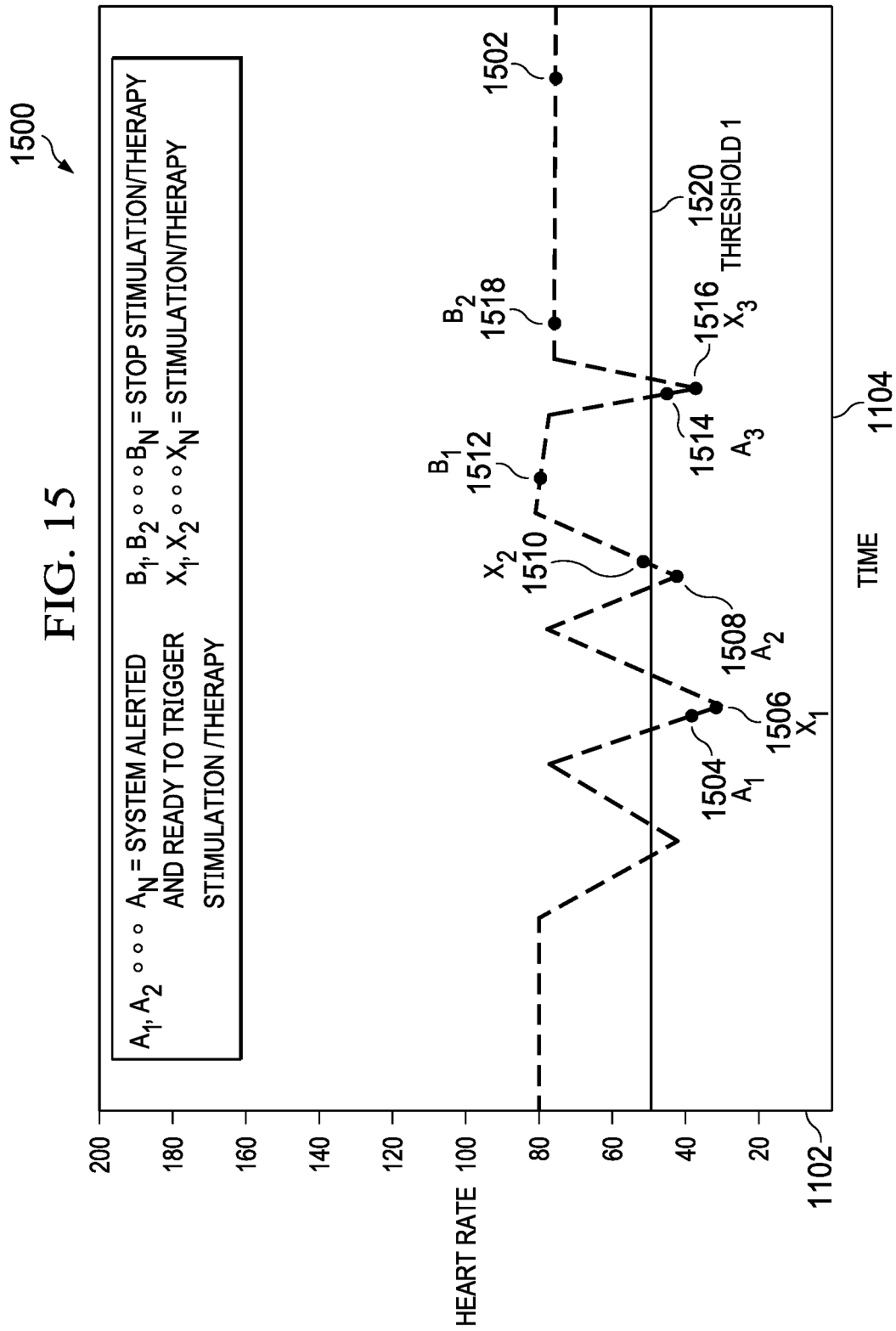
FIG. 15 is another graph of heart rate versus time, according to one embodiment.

In FIG. 15, another graph of heart rate versus time is shown, according to one embodiment. A fifth graph 1500 illustrating a fifth heart rate versus time line 1502 for the patient is shown. In this example, the patient's heart rate goes from 80 heart beats per minute to 40 heart beats per minute which creates a first system alert event 1504 (e.g., A1) because the 40 heart beats per minutes meets or exceeds a first threshold value 1520 (e.g., 50 heart beats per minute). It should be noted that no alert was generated when the heart rate fell to 52 heart beats per minute because 52 heart beats per minute is above the threshold value of 50 heart beats per minute. Further, the system, device, and/or method initiates a first therapy 1506 (e.g., X1) based on the first system alert event 1504 occurring. Further, the patient's heart rate goes from 80 heart beats per minute to 50 heart beats per minute which creates a second system alert event 1508 (e.g., A2) because the 50 heart beats per minutes meets or exceeds the first threshold value 1520 (e.g., 50 heart beats per minute). Further, the system, device, and/or method initiates a second therapy 1510 (e.g., X2) based on the second system alert event 1508 occurring. Further, a first stop stimulation event 1512 (e.g., B1) occurs which turns off all therapies and/or system alerts occurs when the heart rate returns to the approximate starting heart rate and/or a target value. In addition, the patient's heart rate goes from 80 heart beats per minute to 45 heart beats per minute which creates an nth system alert event 1514 (e.g., A3) because the 45 heart beats per minutes meets or exceeds the first threshold value 1520 (e.g., 50 heart beats per minute). Further, the system, device, and/or method initiates an Nth therapy 1516 (e.g., X3) based on the nth system alert event 1514 occurring. Further, an nth stop stimulation event 1518 (e.g., B2) occurs which turns off all therapies and/or system alerts occurs when the heart rate returns to the approximate starting heart rate and/or a target value. Further, all systems alerts and/or therapies may occur as independent events and/or examples. For example, nth system alert event 1514 alert may be the first system alert in a specific example. In other words, no other events and/or therapies occurred before nth system alert event 1514. Therefore, nth system alert event 1514 becomes the first system alert. In addition, one or more warnings may be transmitted to the patient, a caregiver, a doctor, a medical professional, and/or logged.

In regards to FIGS. 11-15 as related to this disclosure, the systems, devices, and/or methods may use a base line heart rate for the patient (e.g., a specific patient Bob, a general patient John Doe with a first health condition, a first age, etc.) over a first time period (e.g. one week, one month, one year, etc.), 50 percentile of all measured heart rates, an average of all heart rates, and/or any other method of determine a baseline heart rate. Further, the threshold level may be determined based on being the 40 percentile of the baseline, 39 percentile of the baseline, 38 percentile of the baseline, . . . , 10 percentile of the baseline, . . . , etc. In addition, the threshold level may be determined based on being the 75 percentile of the baseline, 76 percentile of the baseline, 77 percentile of the baseline, . . . , 90 percentile of the baseline, . . . , 99 percentile of the baseline, . . . , etc. In one example, the threshold value may be the 75 percentile of every recorded heart rate data. In another example, the oscillation does not matter whether the heart rate change is in an increasing direction or a decreasing direction. In various examples, the systems, devices, and/or method may reduce an amplitude of change (e.g., damping the change in heart rate) to enhance system performance and/or to reduce side effects. In addition, the determination of one or more side effects may initiate a reduction in therapy, a stoppage of therapy, a modification of therapy (e.g., changing a therapy that reduces heart rate to another therapy that increases heart rate), one or more warnings, and/or one or more logging of data.

Figure 16:
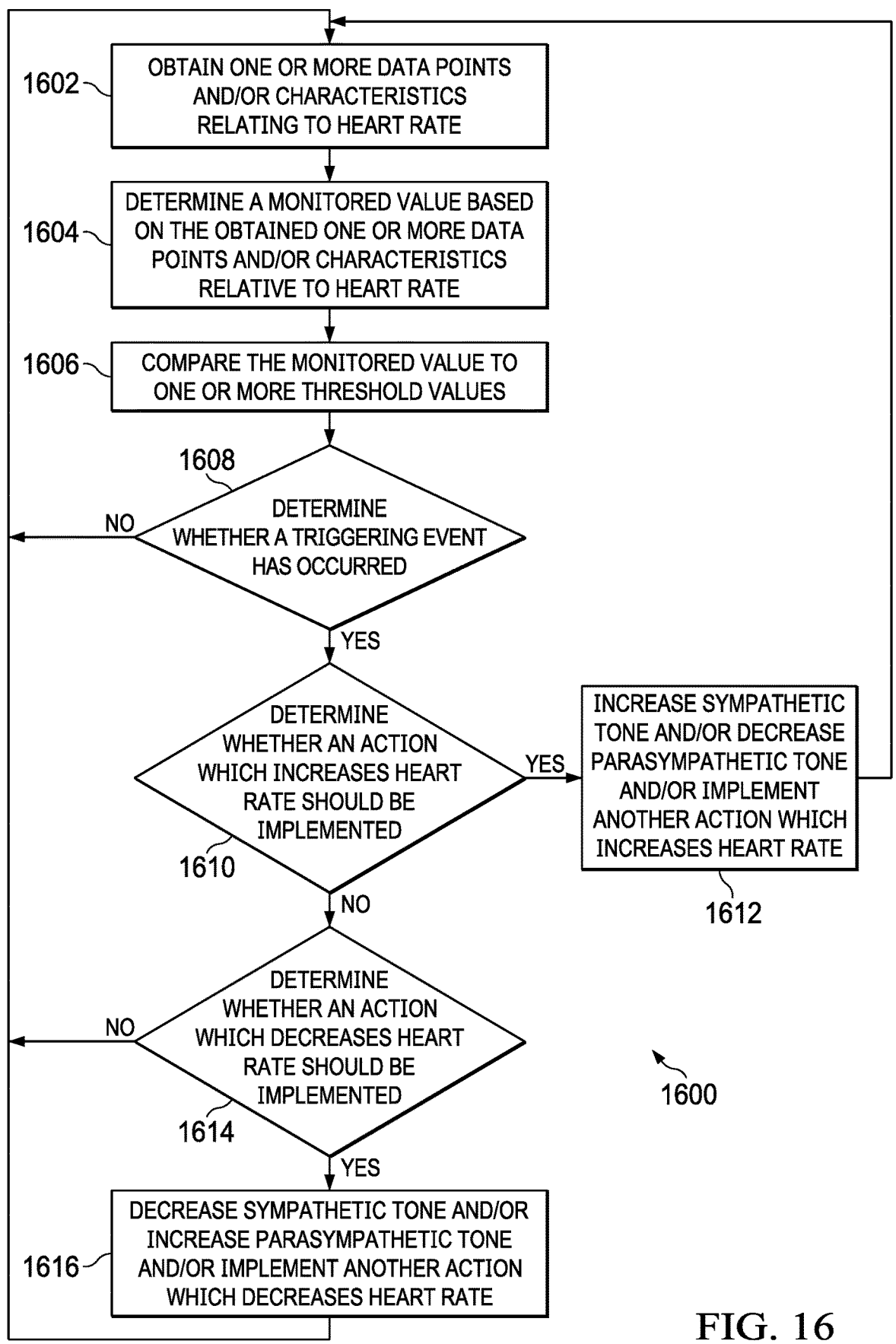
FIG. 16 is a flowchart of a therapy procedure, according to one embodiment.

In FIG. 16, a flowchart of a therapy procedure is shown, according to one embodiment. A method 1600 includes obtaining one or more data points and/or characteristics relating to heart rate of a patient (step 1602). The method 1600 may also include determining a monitored value based one the obtained one or more data points and/or characteristics relating to the heart rate (step 1604). The method 1600 may further compare the monitored value to one or more threshold values (step 1606). The method 1600 may via one or more processors (of a medical device(s) and/or medical device system) determine whether a triggering event has occurred (step 1608). If no triggering event has occurred, then the method 1600 moves back to step 1602. If a triggering event has occurred, then the method 1600 may determine via one or more processors (of a medical device(s) and/or medical device system) whether an action which increases heart rate should be implemented (step 1610). If an action which increases heart rate should be implemented, then the method 1600 may increase a sympathetic tone via one or more actions and/or decrease a parasympathetic tone via one or more actions and/or implement another action which increases heart rate (step 1612). After the implements of one or more actions, the method 1600 returns to step 1602. If an action which increases heart rate should not be implemented, then the method 1600 may determine via one or more processors (of a medical device(s) and/or medical device system) whether an action which decreases heart rate should be implemented (step 1614). If an action which decreases heart rate should be implemented, then the method 1600 may decrease a sympathetic tone via one or more actions and/or increase a parasympathetic tone via one or more actions and/or implement another action which decreases heart rate (step 1616). After the implements of one or more actions, the method 1600 returns to step 1602.

In one embodiment, a system for treating a medical condition in a patient includes: a sensor for sensing at least one body data stream; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the system includes at least one electrode coupled to a vagus nerve of the patient and a programmable electrical signal generator. In another example, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. In another example, the one or more processors may increase a parasympathetic tone to decrease the heart rate of the patient. In another example, the system includes a seizure detection unit which analyzes the at least one body data stream to determine an epileptic seizure status. In another example, the system includes at least one electrode coupled to a vagus nerve of the patient and a programmable electrical signal generator. Further, the one or more processors may apply an electrical signal to the vagus nerve of the patient based on a determination that a seizure is characterized by a decrease in the heart rate of the patient where the electrical signal is applied to block action potential conduction on the vagus nerve.

In another embodiment, a system for treating a medical condition in a patient, includes: a sensor for sensing at least one body data stream; at least one electrode coupled to a vagus nerve of the patient; a programmable electrical signal generator; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the one or more processors may increase a sympathetic tone to increase the heart rate of the patient based on a first triggering event. Further, the one or more processors may decrease a sympathetic tone to decrease the heart rate of the patient based on a second triggering event. Further, the one or more processors may decrease a parasympathetic tone to increase the heart rate of the patient based on a third triggering event. Further, the one or more processors may increase a parasympathetic tone to decrease the heart rate of the patient based on a fourth triggering event.

In another example, the one or more processors may increase the sympathetic tone to increase the heart rate of the patient based on a second triggering event. Further, the one or more processors may increase the sympathetic tone to increase the heart rate of the patient based on a third triggering event. Further, the one or more processors increase the sympathetic tone to increase the heart rate of the patient based on an nth triggering event.

In another example, the one or more processors decrease a sympathetic tone to decrease the heart rate of the patient based on a first triggering event. Further, the one or more processors decrease the sympathetic tone to decrease the heart rate of the patient based on a second triggering event. Further, the one or more processors may decrease the sympathetic tone to decrease the heart rate of the patient based on a third triggering event. In addition, the one or more processors decrease the sympathetic tone to decrease the heart rate of the patient based on an nth triggering event.

Cardio-protection in epilepsy is a rapidly growing field of vital importance. In this disclosure, systems, devices, and/or method of protecting the heart from standstill or fatal arhythmias are disclosed. Further in this disclosure, systems, devices, and/or methods of automated detections, warnings, reportings, treatments, controls and/or any combination thereof of ictal and peri-ictal chronotropic instability are shown.

Figure 17:
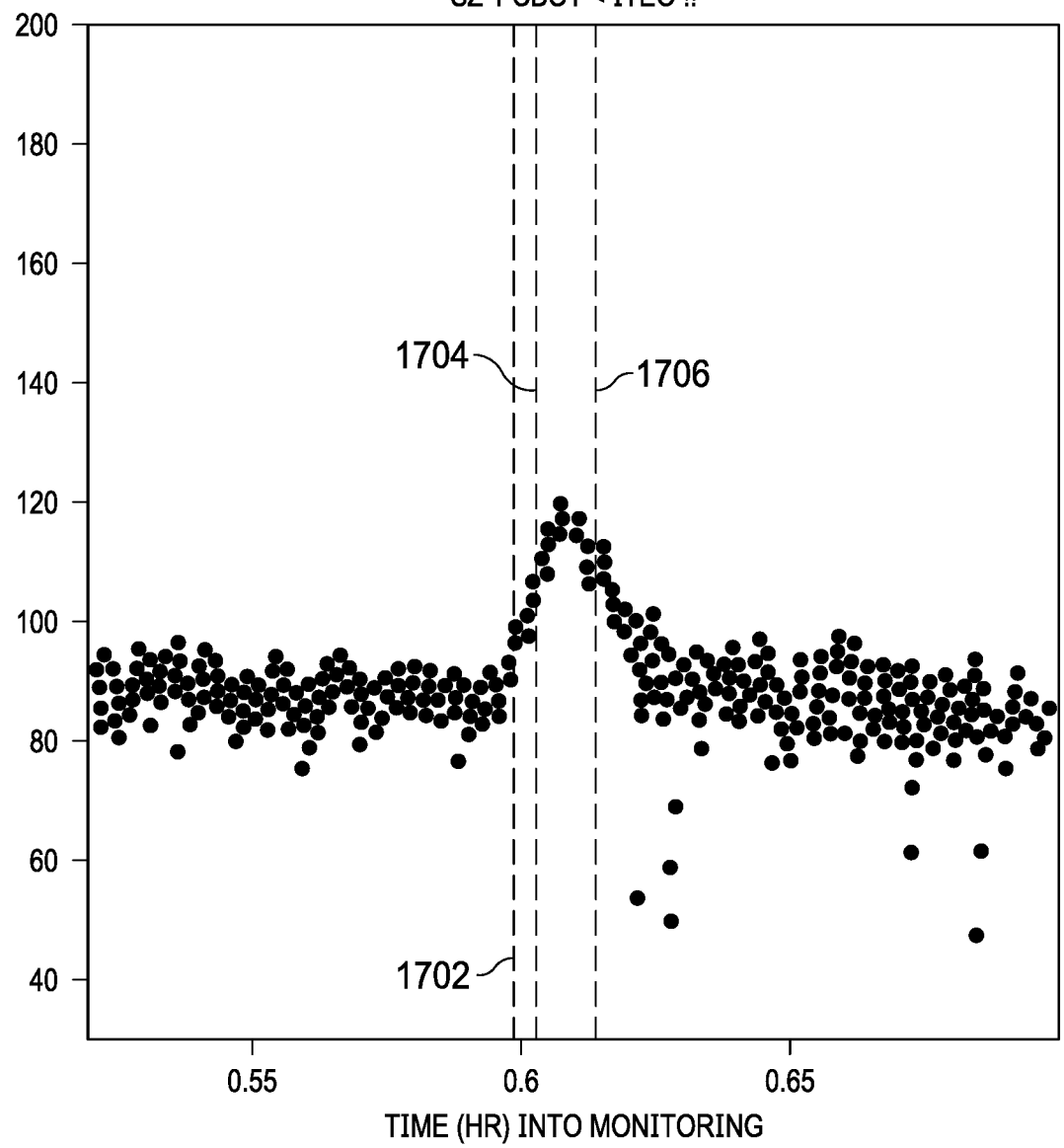
FIG. 17 is a graph relating to the automated detection and control of ictal and peri-ictal chronotropic instability, according to one embodiment.
Figure 18:
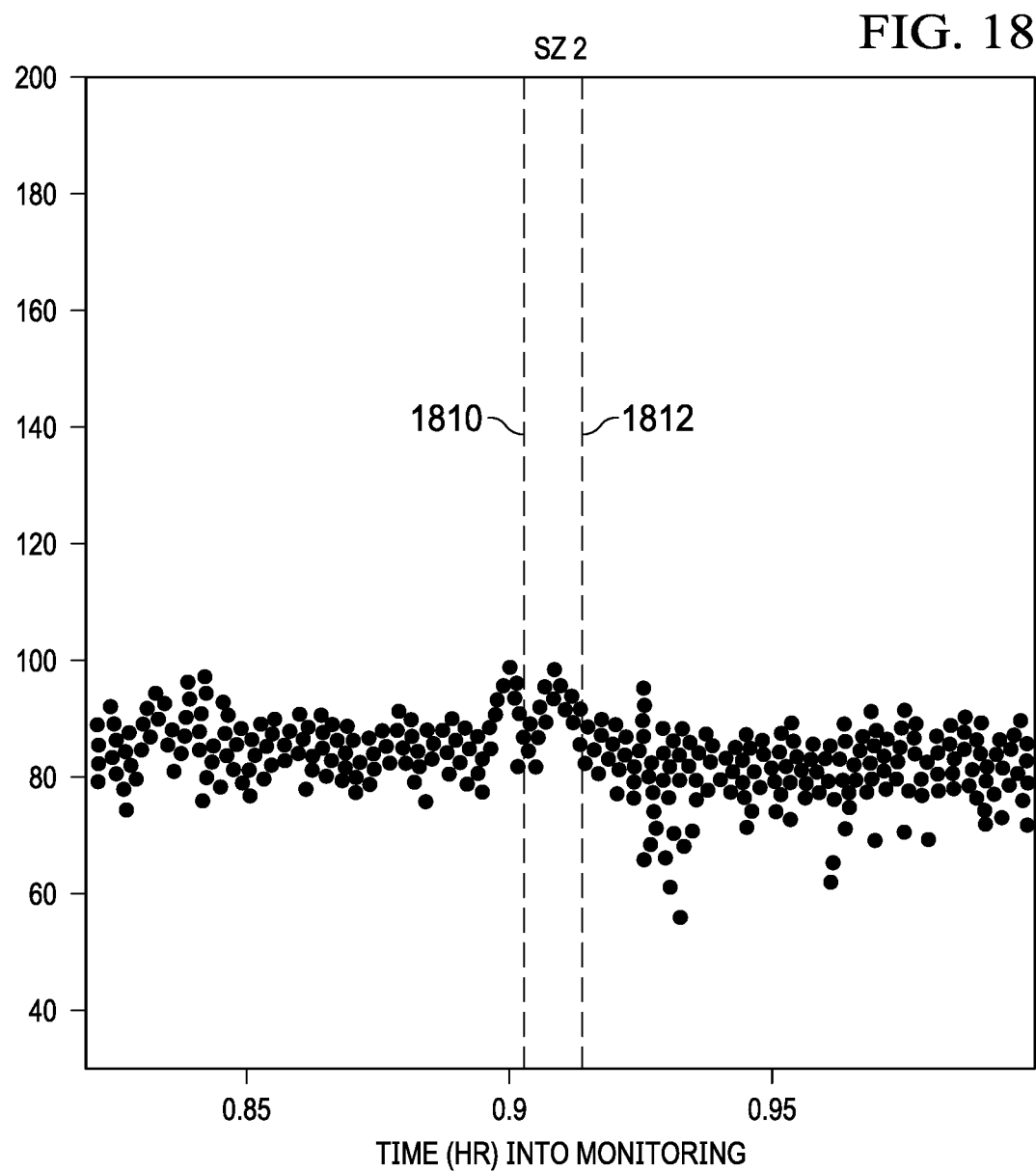
FIG. 18 is a graph relating to the automated detection and control of ictal and peri-ictal chronotropic instability, according to one embodiment.

In FIG. 17, a graph shows monotonic increase and decrease in heart rate. In FIG. 17, a first triggering event, a first warning event, and/or a first therapy event 1702 are shown. Further, a second triggering event 1704, a second warning event, and/or a second therapy event 1704 are shown. In addition, an Nth triggering event, an Nth warning event, and/or an Nth therapy event 1706 are shown. In FIG. 18, the heart rate of the patient increases which is followed by a decrease in heart rate, then an increase heart rate and a final decrease in heart rate. In this example, the first drop in heart rate crossed downwardly the detection threshold which would have temporarily disabled the warning system and the delivery of the therapy. While the first peak was not temporally correlated with paroxysmal activity on any of the intra-cranial electrodes used in this patient, it is likely that the first increase in heart rate was caused by epileptic discharges from a brain site that was not being investigated. In this example, the x-axis is time in hours and the y-axis is heart beats per minute. In this example, an electrographic onset in the brain 1810 is shown and an electrographic termination in the brain 1812 is shown.

Figure 19:
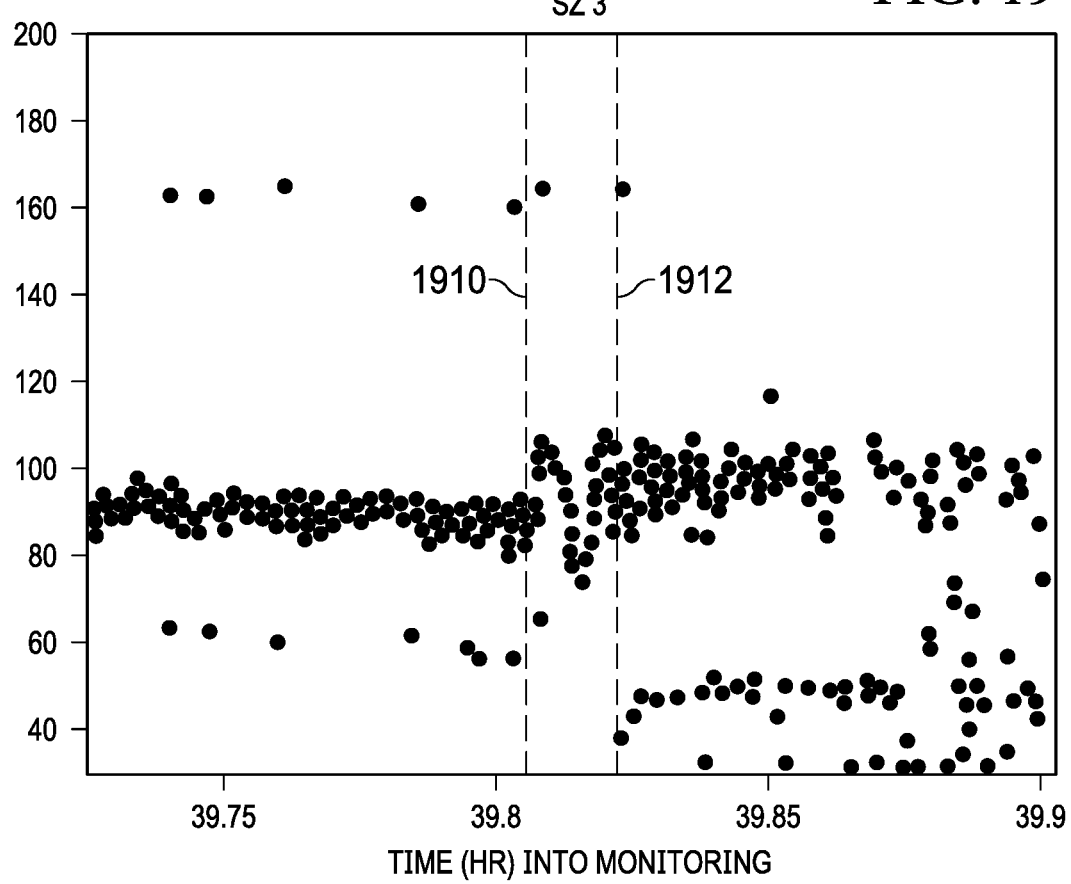
FIG. 19 is a graph relating to the automated detection and control of ictal and peri-ictal chronotropic instability, according to one embodiment.

In FIG. 19, a change in ictal heart rate is shown. In this example, the drop in heart rate during the seizure, is even more prominent that the one depicted in FIGS. 17-18, as it is below the inter-ictal baseline. It should be noted that the oscillations in heart rate during the post-ictal period are indicative of cardiac instability. In this example, a seizure onset point 1910 and a seizure termination point 1912 are shown.

Figure 20:
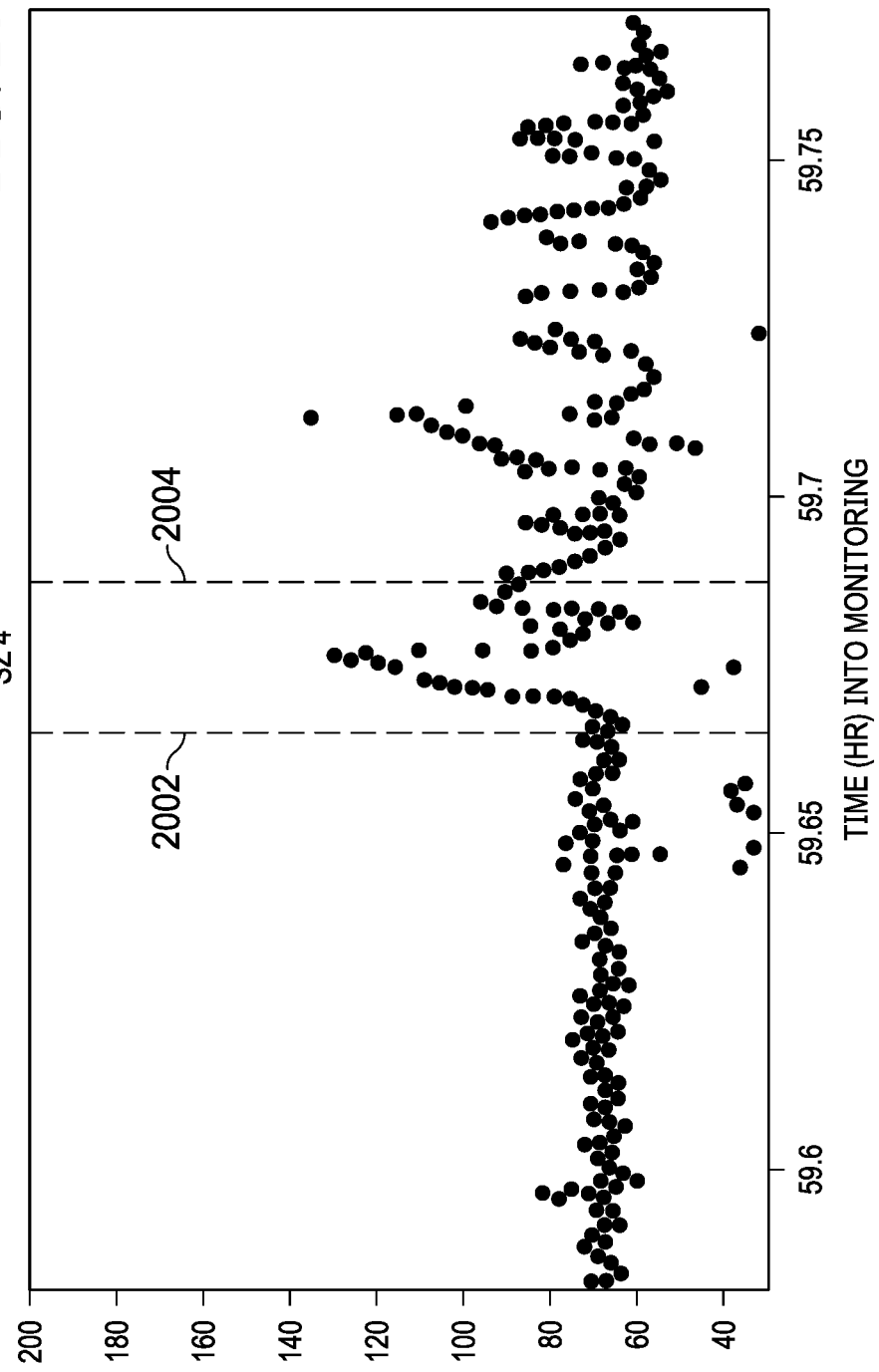
FIG. 20 is a graph relating to the automated detection and control of ictal and peri-ictal chronotropic instability, according to one embodiment.

In FIG. 20, large amplitude tachycardia cycles occurring quasi-periodically after termination of paroxysmal activity recorded with intra-cranial electrodes. While the mechanisms responsible for these oscillations are unknown, the probability that they are epileptic in nature cannot be excluded, since electrographic and imaging data used to guide intra-cranial electrode placement pointed to the existence of only one epileptogenic site.

Figure 21:
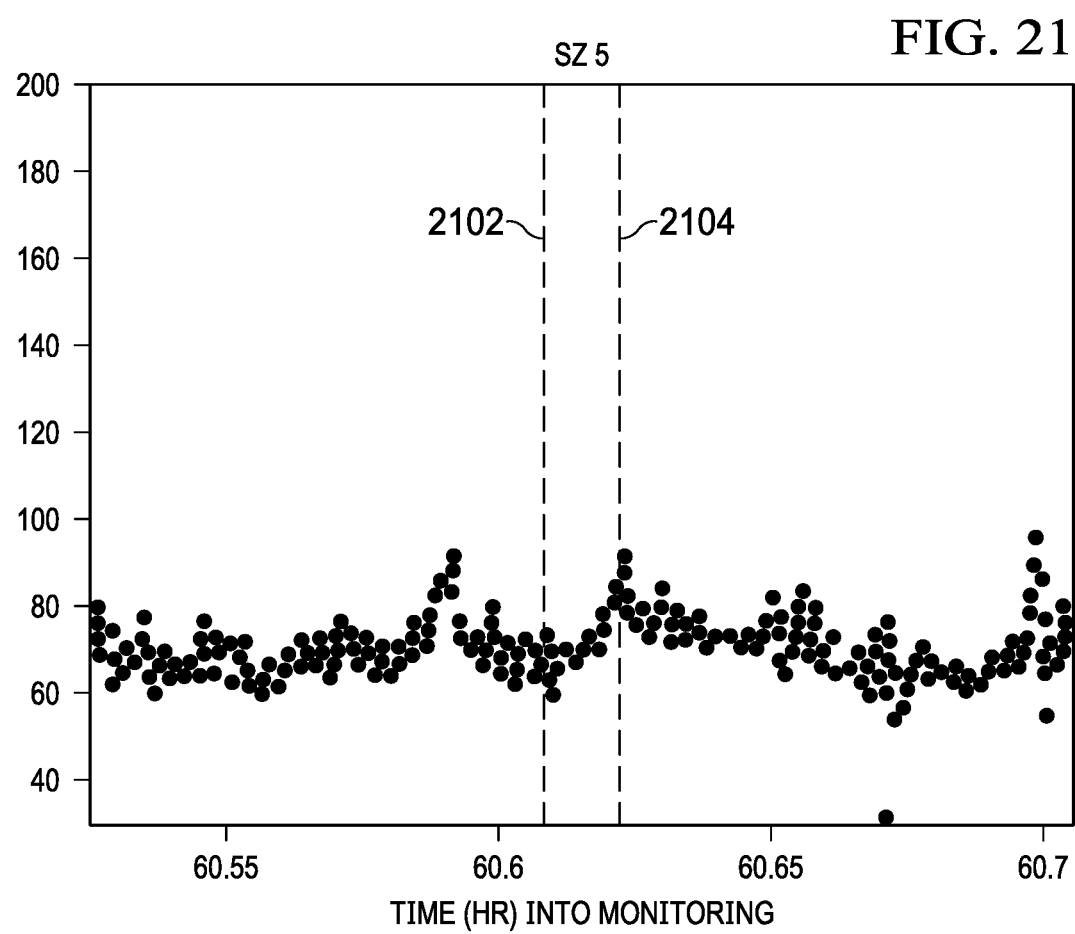
FIG. 21 is a graph relating to the automated detection and control of ictal and peri-ictal chronotropic instability, according to one embodiment.

In FIG. 21, small amplitude continuous quasi-periodic oscillations preceding and following a seizure recorded with intra-cranial electrodes (same patient as FIG. 20). In various embodiments, ictal and peri-ictal cardiac instability are shown. The mechanisms leading to SUDEP have not been elucidated, in part due to the inability to record data during the critical events that culminate in cardiac fibrillation or in standstill (or in respiratory arrest). In this example, a first triggering event, a first warning event, and/or a first therapy event 2102 are shown. Further, an Nth triggering event, an Nth warning event, and/or an Nth therapy event 2104 are shown.

The data obtained in intractable epileptics undergoing epilepsy surgery evaluation not only supports a cardiac mechanism (of course, not at the exclusion of catastrophic respiratory failure) but more specifically points to chronotropic instability as backdrop against which, lethal arrhythmias or cardiac standstill may ensue. Moreover, the instability is not restricted to the ictal period but, in certain cases, precedes and/or follows it for several minutes. FIGS. 17-21 illustrate the spectrum of instability in intractable epileptics. This phenomenon is referred herein to as Ictal and Pre-Ictal Chronotropic Instability.

The challenges that for accurate quantification and delivery of efficacious therapies, ictal chronotropic instability poses, were addressed and strategies to manage them are outlined. Here, the attention is focused on Ictal and Pre-Ictal Chronotropic Instability, a more prolonged and serious pathological phenomenon in intractable epileptics and on the vital issues of cardio-protection.

The aim of this disclosure is to contingently and adaptively dampen based on the slope, amplitude, duration and "direction" (positive or negative chronotropic and its magnitude relative to an adaptive baseline/reference heart rate) the heart oscillations present before, during or after epileptic seizures.

While several embodiments may be envisioned, on embodiment (for efficacy, practicality and cost-effectiveness) is to electrically stimulate/activate the trunk or a branch of the right vagus nerve in the case of elevations in heart (to reduce the heart rate, when there are more than 2 consecutive oscillations/cycles or 1 that is large and prolonged. The intensity and duration of stimulation as well as other parameters are determined by the slope, amplitude and duration of the oscillations, while ensuring adequate blood perfusion to all organs. In the case of negative chronotropic effects (decreases in heart rate) the trunk or a branch of the right vagus nerve may be "blocked" using certain electrical stimulation techniques or through cooling; the effect of this intervention is to increase heart rate.

In one embodiment, the "height" of the oscillation is the only feature considered. While obviously important, this embodiment does not take into consideration a possibly more important feature: the rate at which the oscillation occurs: the consequences of waiting to intervene until an oscillation reaches a certain height (e.g., 120 bpm) are different if it takes, 30 seconds for the heart rate to reach the value than if it takes 2 seconds to reach the value. Estimating the rate of change of the heart rate, provides life-saving information. Another aspect is the inter-maxima or inter-minima interval between oscillations. Having heart rate oscillation occur every 2-3 seconds is much more serious than every 1-2 hours. In one example, one benefit may be that the window to act is lengthen which can save lives. In one embodiment, a system for treating a medical condition in a patient includes: a sensor for sensing at least one body data stream; a heart rate unit which determines a heart rate and a heart rate oscillation of the patient based on the at least one body data stream; and a logic unit which compares via one or more processors a monitored value which is determined based on one or more data points relating to the heart rate and to the heart rate oscillation to a threshold value, the logic unit determines a triggering event based on the comparison where the one or more processors initiate one or more actions to change the heart rate of the patient based on the determination of the triggering event.

In another example, the system includes at least one electrode coupled to a vagus nerve of the patient and a programmable electrical signal generator. Further, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. Further, the one or more processors may increase a parasympathetic tone to decrease the heart rate of the patient. In addition, the system may include a seizure detection unit which analyzes the at least one body data stream to determine an epileptic seizure status. The system may include at least one electrode coupled to a vagus nerve of the patient and a programmable electrical signal generator where the one or more processors apply an electrical signal to the vagus nerve of the patient based on a determination that a seizure is characterized by a decrease in the heart rate of the patient and where the electrical signal is applied to block action potential conduction on the vagus nerve. In addition, the heart unit may determine an inter-maxima interval and an inter-minima interval between a first oscillation and a second oscillation. Further, the logic unit may compare the inter-maxima interval and the inter-minima interval to an interval threshold. In addition, the one or more processors may initiate one or more actions based on the interval threshold being reached.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below. In addition, all examples, embodiments, and/or elements may be combined in any manner that are disclosed in this document. In other words, an element from a first example can be combined with any other element, such as, a second element from an Nth example. For brevity, all these examples are not written out but are part of this document.

Illustrative embodiments of the disclosure are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

In one embodiment, the present disclosure provides a method of detecting a state change based upon data derivable from cardiac signals. The state change can be, for example, at least one of an unstable brain state, a brain state indicative of an elevated probability of a state change, a brain state indicative of an impending state change, or a state change, among others.

In one embodiment, the present disclosure provides a method for indicating an occurrence of a state change. In one embodiment, the method comprises obtaining a time series of cardiac data from a patient; determining a reference heart rate parameter from said cardiac data; determining a heart rate derivative shape from said time series of cardiac data, wherein said heart rate derivative shape comprises at least one characteristic selected from a number of phases relative to said reference heart rate parameter, a number of extrema of said heart rate derivative, a number of directions of change of said heart rate derivative, a number of positive phases, or a number of negative phases; and indicating an occurrence of a state change based upon a determination that said heart rate derivative shape matches a state change template in said at least one characteristic.

The cardiac data can be gathered by any of a number of techniques. For example, the cardiac data may be gathered by an electrocardiogram (EKG) device. For another example, the cardiac data may be gathered by a cranial nerve stimulator device. In one embodiment, the cardiac data may be related to the R-waves of the beat sequence, such as a time series of R-waves or a series of R-R intervals. Those skilled in the art having benefit of the present disclosure would appreciate that other time series of cardiac waves and/or their fiducial points (e.g., P waves, T waves, etc.) may be used and still remain within the spirit and scope of the present disclosure.

Data relating to R-waves may be gathered by an EKG device or, in one embodiment, by a vagus nerve stimulator, such as described in U.S. Pat. No. 5,928,272, which is hereby incorporated by reference herein.

Obtaining the cardiac data may comprise sensing a time of beat sequence of a patient's heart and generating a time series data stream from the time of the beat sequence. In a further embodiment, receiving the cardiac data of the patient's heart may comprise sensing and time-stamping a plurality of R waves, and generating the time series data stream may comprise determining a series of R-R intervals from the time stamps of the sensed R waves.

In one embodiment, the fiducial time marker is an R wave peak or threshold crossing. The amplitude or height of one or more representative R waves may be used to set a threshold that, when reached or crossed, is registered as a fiducial time marker of a heart beat.

In one embodiment, a heart rate derivative is determined from the time series of cardiac data. As defined herein, a "heart rate derivative" is a value derivable, directly or indirectly, from the time series of cardiac data, wherein the value relates to a feature, property or relationship between two or more heart beats. Although a first or higher-order derivative, as understood from calculus, is a "heart rate derivative" under the above definition, a heart rate derivative is not necessarily a first or higher-order calculus derivative. Exemplary heart rate derivatives include, but are not limited to, heart rate and heart rate variability (HRV). A "shape" is used herein to refer to a feature apparent to the person of ordinary skill in the art upon viewing a graph of the heart rate or of one of its derivative over a period of time. In one embodiment, a heart rate derivative shape comprises at least one characteristic selected from a number of phases relative to a reference heart rate parameter, a number of extrema of the heart rate derivative, a number of directions of change of the heart rate derivative, a number of positive phases, or a number of negative phases.

By "heart rate shape" is meant one or more characteristics or features of a time series of cardiac data that are reflective of the appearance of that time series if plotted on a graph (on the y-axis and time on the x-axis). For example, one characteristic of heart rate shape is a number of phases relative to the reference heart rate parameter. A "phase" is a period between two consecutive deviations from, crossings of, or returns to the reference heart rate parameter. A phase may be positive (having a value greater than the reference heart rate parameter) or negative (having a value less than the reference heart rate parameter). Yet another exemplary characteristic of heart rate shape is a number of extrema of heart rate. An "extremum" (plural, "extrema") is a point where the slope of heart rate changes sign, or phrased alternatively, a point that is a highest high or lowest low of heart rate for some length of time or number of beats before and after. Still another exemplary characteristic of heart rate shape is a number of directions of heart rate change, which can be defined as the number of changes of the sign of the slope of heart rate, plus one. Yet another exemplary characteristic of heart rate shape is the steepness of one or more ascending or descending slopes.

Though not to be bound by theory, we have found that heart activity during normal states (exercise, anger, etc.) and abnormal states (e.g., epileptic seizures) as displayed or graphed over various time scales take on distinctive shapes which may be used to identify the various states as well as changes from one state to another, such as from non-seizure to seizure. Said shapes are considered and treated herein as templates, given their stereotypical nature, and are used in several ways (to be described below) to detect states, state changes, state and/or state change onsets, and/or other features, such as duration, intensity or magnitude, and/or other relevant characteristics, such as type of state or state change.

Another heart rate derivative that may be considered is a heart rate volatility (non-stationarity) parameter, a measure of dispersion which may be defined as a change in the standard deviation or variance of heart rate over a moving window. Commonly, the higher the volatility, the higher appears to be the probability of state changes. Volatility, a metric often found in financial contexts, is used here to obtain certain information about the state of a system regardless of the similarities or dissimilarities between financial and biological time series and consideration for the underlying systems' dynamics.

For example, let . . . $^{t-2}Q$, $^{t-1}Q$, $^{t}Q$, $^{t+1}Q$, . . . be a stochastic process. Its terms $^{t}Q$ represent heart rates as components of a vector or a matrix. The volatility of the process at time $t^{-1}$ is defined as the standard deviation of the time t return. Typically, log returns are used, so the definition becomes $$\text{volatility} = std\left(\log\left(\frac{^{t}Q}{^{t-1}Q}\right)\right) \qquad [1]$$

wherein log denotes a natural logarithm.

If heart rate time series are conditionally homoskedastic, definition [1] is precise. However, if they are conditionally heteroskedastic, measure [1] requires modification. Volatility at time $t^{-1}$ represents in this case, the standard deviation of the time t log return conditional on information available at time $t^{-1}$ as defined below $$\text{volatility} = {}^{t-1}std\left(\log\left(\frac{^{t}Q}{^{t-1}Q}\right)\right)$$

wherein the preceding superscript $t^{-1}$ indicates that the standard deviation is conditional on information available at time $t^{-1}$.

Transitions from homoskedasticity (defined herein as approximately constant standard deviations over a certain time window) to heteroskedasticity (inconstant standard deviation) also provide information about the probability of being in or near a state change of interest and may be used for automated detection, warning, delivery of therapy and logging (of events, warnings and therapy) purposes.

Volatility will be measured using time scales (seconds to days) based on temporal (e.g., duration) and other properties of the state change on interest and of the reference state.

The method also comprises indicating an occurrence of a state change based upon a determination that said heart rate derivative shape matches a state change template in said at least one characteristic.

A "state change template" is a template known or discovered by the practitioner to be associated with the state change, wherein the template can be used in the analysis of the heart rate derivative shape.

Plots of instantaneous heart rate (y-axis) as a function of time (x-axis) in subjects with epilepsy reveal consistent changes before, during and after seizures, referred herein to as circum-ictal changes. ("Circum-ictal" or "circumictal," as used herein, encompasses pre-ictal, ictal, and post-ictal subperiods. The circumictal period can be considered the time window (e.g., in min) preceding and following a seizure during which cardiac activity differs from that observed during interictal conditions, normal physical activity (including exercise), intense emotions (fear, anger, etc.), and physiological functions such as defecation, urination or coitus). The curves described by these circum-ictal changes in heart rate, approximate triangles or parabolae, and may have indentations of varying sizes. See the discussion of FIGS. 26-38B below for more information. Visual review of a large human database of instantaneous heart rate plots reveal that over a certain window length (referred herein as the mesoscopic scale) their circum-ictal shapes are limited to the triangles and parabolae and to "deformations" of these two shapes (see FIG. 26). These "deformations" appear to have temporal and magnitude dependencies, in that the longer the duration of the change in heart rate and the larger its magnitude, the more likely they are to occur. The behavior of these shapes likely reflect fluctuations in the strength of sympathetic and parasympathetic inputs to the heart. For example, transient, rapid drops in heart rate may be caused by either a withdrawal in sympathetic tone or by an increase in parasympathetic tone resulting from differential activation or inhibition by epileptiform activity of brain regions involved in autonomic control.

The shape (i.e., all the geometrical information that is invariant to position (including rotation) and scale) of these curves may be used for detection of changes in brain state such as epileptic seizures and their properties may be characterized through use of statistical shape analysis (e.g., Procrustes analysis), of the different embodiments of "matched filtering" or of other geometrical (Euclidian and non-Euclidian) methods. Other approaches such as computing the area of the triangles and parabolae and comparing the results to a reference value outside the circum-ictal state[ ] may be used. In the case of triangles, there area may be calculated using for example Heron's formula:

$$\text{Area} = \sqrt{S(S-a)(S-b)(S-c)}, \text{ where}$$

$S = \frac{1}{2}(a+b+c)$ and a, b, and c are the sides of the triangle.

Similarly the area of parabolae (Area=$\frac{2}{3}$ b×h, where b is the base and the height, may be computed and used to detect seizures.

Other attributes not captured by the concept of shape may be applied as need to the signal for detecting state changes such as epileptic seizures.

In one embodiment, the at least one characteristic of the state change template comprises two or more phases relative to the reference heart rate parameter, two or more extrema of the heart rate derivative, three or more directions of change of the heart rate derivative or its slope, a number of positive phases, or a number of negative phases, provided the total number of positive phases and negative phases is two or more.

In another embodiment, the at least one characteristic of the state change template comprises at least one phase relative to the reference heart rate parameter, at least one extremum of the heart rate derivative or its slope, two or more directions of change of the heart rate derivative, a number of positive phases, or a number of negative phases, provided the total number of positive phases and negative phases is at least one.

In another embodiment, the at least one characteristic of the state change template comprises at least one of the amplitude of at least one phase, the duration of at least one phase, the valence (positive or negative) of at least one phase, at least one slope of at least one phase, the arc length (which is used interchangeably with line length) of at least one phase, the number of extrema in at least one phase, and the sharpness of the extrema of at least one phase.

A reference heart rate parameter, as used herein, is a reference value obtained during a state that is deemed of no or little interest for automated detection, warning, treatment or logging purposes. The reference heart rate parameter may be a single value, a series of values, a statistical is selected from the group consisting of a shape, a vector, a vector space, a matrix and two or more thereof.

For example, heart activity during a non-seizure state is considered as a reference state. The reference heart rate parameter may be calculated from a time series of value over any particular window, such as a window having a length from 30 seconds to 24 hours, although longer or shorter windows may be used. The window may be a simple window or an exponentially-forgetting window, as discussed in U.S. patent application Ser. No. 12/770,562, filed Apr. 29, 2010; Ser. No. 12/771,727, filed Apr. 30, 2010; and Ser. No. 12/771,783, filed Apr. 30, 2010; the disclosures of each hereby incorporated herein by reference. The reference heart rate parameter may be calculated as any measure of any tendency of the time series, such as the central tendency of the time series. For example, the reference heart rate parameter may be calculated as a mean, median, nth percentile (where n can be from 30 to 70), or exponential moving average of the time series, among other measures of central tendency. Other mathematical or statistical measures, including, but not limited to, correlation dimension, entropy, Lyapunov exponents, and fractal or multifractal dimensions, may be also applied to any of the parameters or their templates.

The reference heart rate parameter may be determined from previously recorded data, or from "normative" values obtained from normal or abnormal cohorts of subjects or populations or it may be determined from the time series of cardiac data referred to above.

Figure 29A:
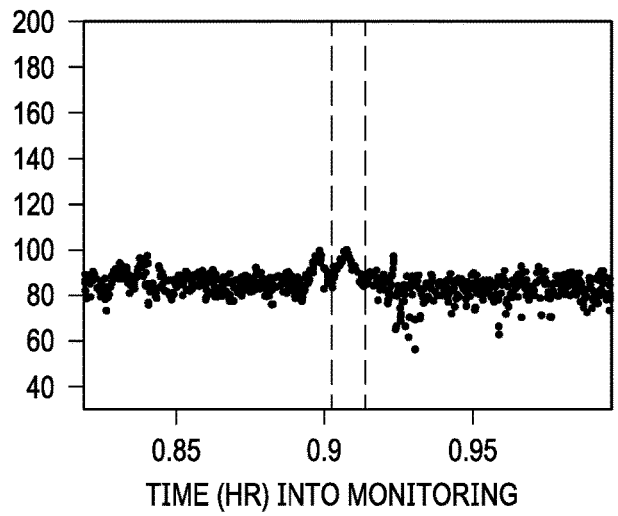
FIG. 29A shows a graph of heart rate vs. time, with epileptic events identified by ECoG indicated by vertical lines, from which an "M" pattern is discernible, in accordance with an illustrative embodiment of the present disclosure.
Figure 29B:
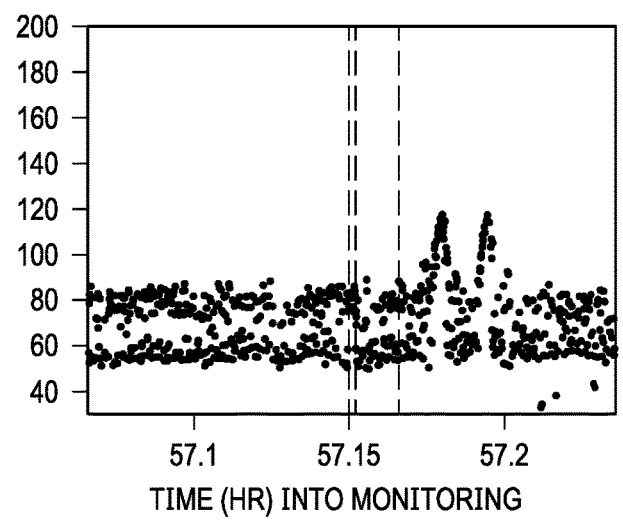
FIG. 29B shows a graph of heart rate vs. time, with epileptic events identified by ECoG indicated by vertical lines, from which an "M" pattern is discernible, in accordance with an illustrative embodiment of the present disclosure.

An exemplary state change template can be derived from the pattern shown in FIGS. 29A-29B, wherein the changes in heart rate during a seizure form a readily discernible "M" between 0.88 hours and 0.92 hours, having one positive phase relative to a reference heart rate parameter (calculated as the median value from about 0.85 hours to 0.89 hours and from about 0.93 hours to about 1.00 hour), three extrema (two maxima and one minimum, each being an extremum relative to about 20 seconds before and 20 seconds after), and four directions of heart rate change.

The state change template may be the "raw" pattern (analog or digitized) or it can be derived by smoothing, averaging, or otherwise mathematically processing subseries of cardiac data obtained during state changes. A "matched filter" is a type of filter matched to the known or assumed characteristics of a target signal, to optimize the detection of that signal in the presence of noise. A matched filter is the filter with impulse response equal to the time reversed, complex conjugate impulse response of the input.

One skilled in the art will appreciate that when applying matched filter techniques to attempt to detect a pattern in a signal, the raw signal may first be transformed so that it has zero mean on a timescale of interest when the pattern is absent. Such transformation may include, but not be limited to, detrending or subtracting a background reference value (or time-varying reference signal) from the raw signal and is used to remove bias in the matched filter output and improve its signal-to-noise ratio.

Seizure detection may be performed over multiple time scales or window lengths listed in no particular order:
  a) "Mesoscopic" corresponding to a scale of observation of several seconds to tens of seconds (e.g., 10-300 s) to capture at least in part, a change in the shape of heart rate plot representative of a state change.
  b) "Microscopic" corresponding to the scale of observation of at least part of a heart beat such as that represented by an EKG's P-QRS-T complex.
  c) "Macroscopic" corresponding to a scale of observation longer than 300 s to encompass more than the information contained in the mesoscopic scale or window as defined in a).

Seizure detection at a macroscopic scale provides information not obtainable with the two other scales (micro- and mesoscopic) allowing for the identification of certain patterns (defined herein as the occurrence of more than one triangle or parabola or combinations thereof within a macroscopic window).

A shape deformation (e.g., a deformed "M") may show local and global extrema that may be used for detection and validation purposes.

In one embodiment, the method comprises matched filtering. Matched filtering is a theoretical framework and not the name of a specific filter. A matched filter is a type of filter matched to the known or assumed characteristics of a target signal and is designed to optimize the detection of that signal in the presence of noise as it maximizes S/N. A matched filter's impulse response is equal to the time reversed, complex conjugate impulse response of the input.

The output response of a "matched" filter derived from meso-, micro- or macroscopic patterns, as it is passed through any of these patterns is characteristic (it forms a spatio-temporal pattern) and in turn may be used not only to validate detections but to allow detections before the convolution is completed ('early' detection).

A second filter matched to the first matched filter's output response may be run simultaneously with the first matched filter and its output response may be used for early detection and second level validation of the detection.

The pattern formed by any of the cardiac activity parameters may be used as a matched filter. Other realizations such as the orthogonal and projected orthogonal matched filter detection (Eldar Y C. Oppenheim A, Egnor D. Signal Processing 2004; 84: 677-693), adaptive matched filter and parametric adaptive matched filter (Dong Y. Parametric adaptive filter and its modified version DSTO-RR-0313 My 2006 Australian Government, Dept. of Defence); the nearest matched filter for classification of spatio-temporal patterns (Hecht-Nielsen R. Applied Optics 1987; 26:1892-98), an outlier resistant matched filter (Gerlach K. IEEE Trans Aerospace Electronic Syst 2002; 38:885-901), a phase-only matched filter (Horner J L, Gianino P D. Applied Optics 1984; 23:812-16) may be also used for detection and validation of state changes such epileptic seizure.

The detection and validation of states based on the morphology or shape of signals may be performed at various time scales (micro-, meso-, or macroscopic) through estimation of the autocorrelation function of said shapes or patterns. Furthermore, estimation of the autocorrelation function of a reference state may also be used for detection and validation of state changes alone or in combination with the autocorrelation estimates of the state change shapes or patterns. Autocorrelation may be considered as an equivalent method to matched filtering.

Other methods, such as non-linear detectors (Theiler J, Foy B R, Fraser A M. Beyond the adaptive matched filter: Non-linear detectors for weak signals in high dimensional clutter. Proc SPIE 6565 (2007) 6565-02: 1-12) and maximum likelihood estimation (Forney G D, Maximum-likelihood estimation of digital sequences in the presence of intersymbol interference. IEEE Trans Information Theory 1972; 18:363-76), may be also applied in this disclosure.

Matching a heart rate shape to a state change template can be performed by any appropriate mathematical technique. For example, pattern matching by use of a matched filter is generally known to one skilled in the art. In one embodiment, the state change template comprises at least one matched filter. In one embodiment, a "match" refers to a match score found by a matched filter analysis of greater than about 0.75, such as greater than about 0.80, greater than about 0.85, greater than about 0.90, greater than about 0.95, greater than about 0.98, or greater than about 0.99. A "failure to match" refers to a match score found by a matched filter analysis of less than about 0.75, such as less than about 0.80, less than about 0.85, less than about 0.90, less than about 0.95, less than about 0.98, or less than about 0.99. However, these values may be changed as needed.

In one embodiment, the state change template comprises at least a state change matched filter and a reference parameter matched filter. A "match" can be defined as a match to the state change matched filter not accompanied by a match to the reference parameter filter.

Regardless of the type of filter, in one embodiment, the heart rate derivative shape has a matched filter score to said state change template greater than a value threshold for at least a duration threshold. For example, any of the values set forth above may be used as the value threshold and the duration threshold may be selected as any appropriate number of seconds or heart beats, such as 1 to 10 seconds, or 1 to 10 beats, such as 3 beats.

In one embodiment, the state change template exists in a first timescale and said heart rate derivative shape is present in said first timescale. For example, the heart rate derivative shape is present over a first timescale not typically found in a reference heart rate derivative shape observed during rising from lying to sitting, rising from sitting to standing, minor physical exertion, exercise, or emotionally-intense experiences. This allows distinction between heart rate derivative shapes associated with a state change of interest, e.g., an epileptic seizure, and heart rate derivative shapes associated with normal daily activities.

In one embodiment, the state change template comprises at least one positive phase and at least one negative phase. In a further embodiment, the at least one positive phase is a period of elevated heart rate. In an even further embodiment, the period of elevated heart rate is a period of tachycardia. In people fifteen years of age and older, tachycardia is defined as a heart rate greater than 100 bpm. In another further embodiment, the at least one negative phase is a period of decreased heart rate. In an even further embodiment, the period of decreased heart rate is a period of bradycardia. Bradycardia is defined in adults as a heart rate less than 60 bpm.

In one embodiment, the state change template comprises at least two extrema of heart rate. In a further embodiment, the state change template can also comprise at least two phases.

The state change template may comprise one or more shapes readily discernible to the human eye. For example, the state change template may comprise a triangle, such as that shown in FIG. 27. Although in many cases, state change templates that appear more complex than a triangle may be useful, they can generally be understood as involving one or more triangles or parabolas and/or deformations thereof.

Figure 26:
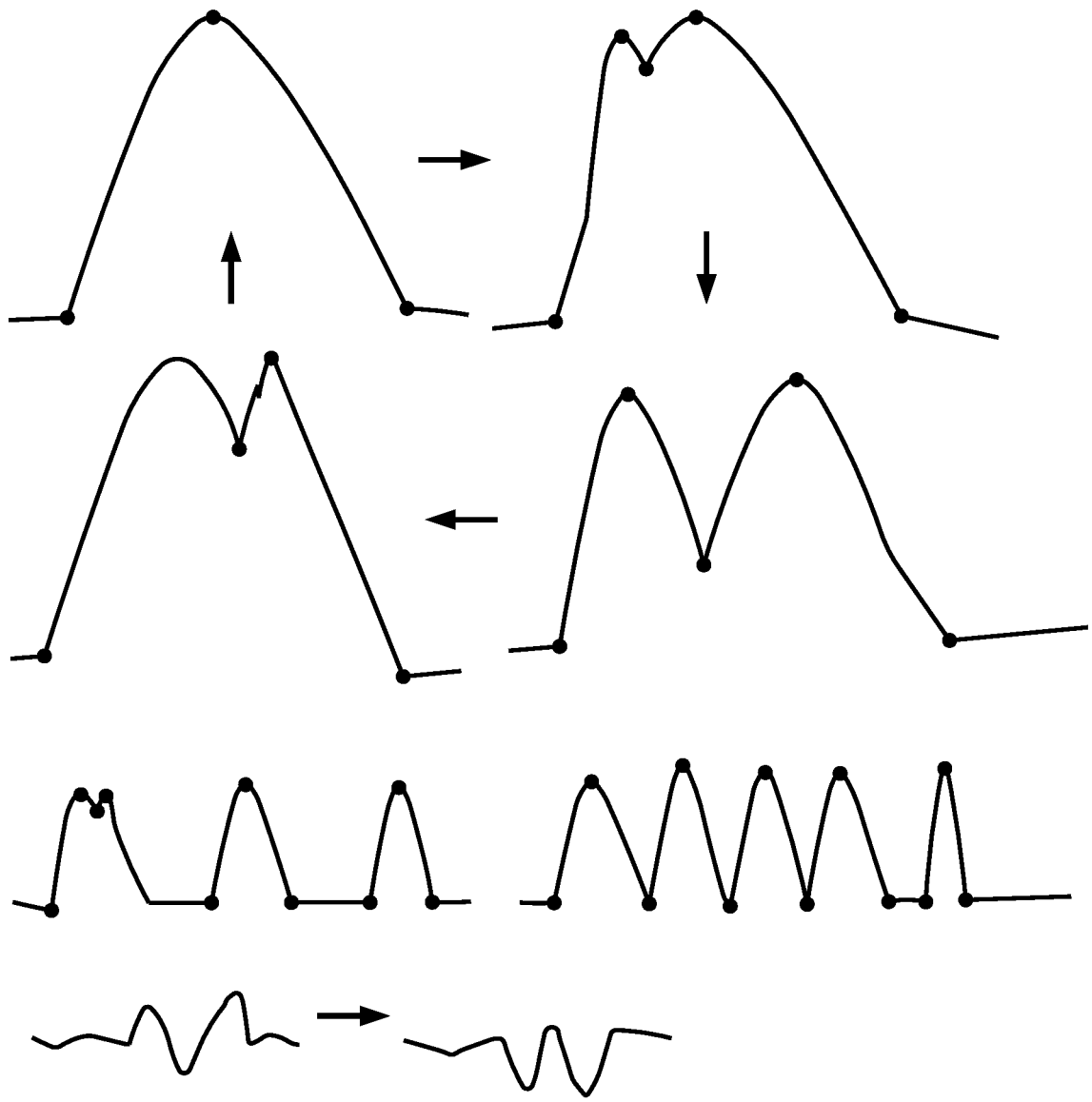
FIG. 26 shows basic shapes of a heart rate plot, from which more complex shapes can be produced by deformation in accordance with an illustrative embodiment of the present disclosure.

FIG. 26 illustrates the metamorphosis or transformation of circumictal heart rate shapes or patterns at a mesoscopic scale. The simplest shape is that of a parabola (left upper panel). In certain seizures a short-lived withdrawal or reduction of sympathetic influences or an increase in parasympathetic ones early in the course of a seizure causes a notch or indentation in the parabola (right upper panel). In other seizures (in the same subject or in a different subject), a later, more pronounced and prolonged withdrawal or reduction of sympathetic influences or an increase in parasympathetic ones (compared to that seen in the right upper panel) leads to a prominent indentation or notch (right lower panel), resembling the letter "M". A later, briefer, and less pronounced withdrawal or reduction of sympathetic influences or an increase in parasympathetic ones (compared to that seen in the right lower panel) causes an indentation in the parabola.

The relative balance of sympathetic and parasympathetic influences can be assayed at multiple timescales. As can be seen with reference to at least some of the figures discussed below, the relative balance of sympathetic and parasympathetic influences can oscillate on multiple timescales.

While a parabola is shown in FIG. 26 as an example, this may be replaced by a triangle or by any other topologically equivalent shape.

We have discovered a number of specific patterns or shapes occurring in at least some circumictal periods of at least some patients, which patterns or shapes may be used as the basis for a state change template as discussed herein.

Figure 27:
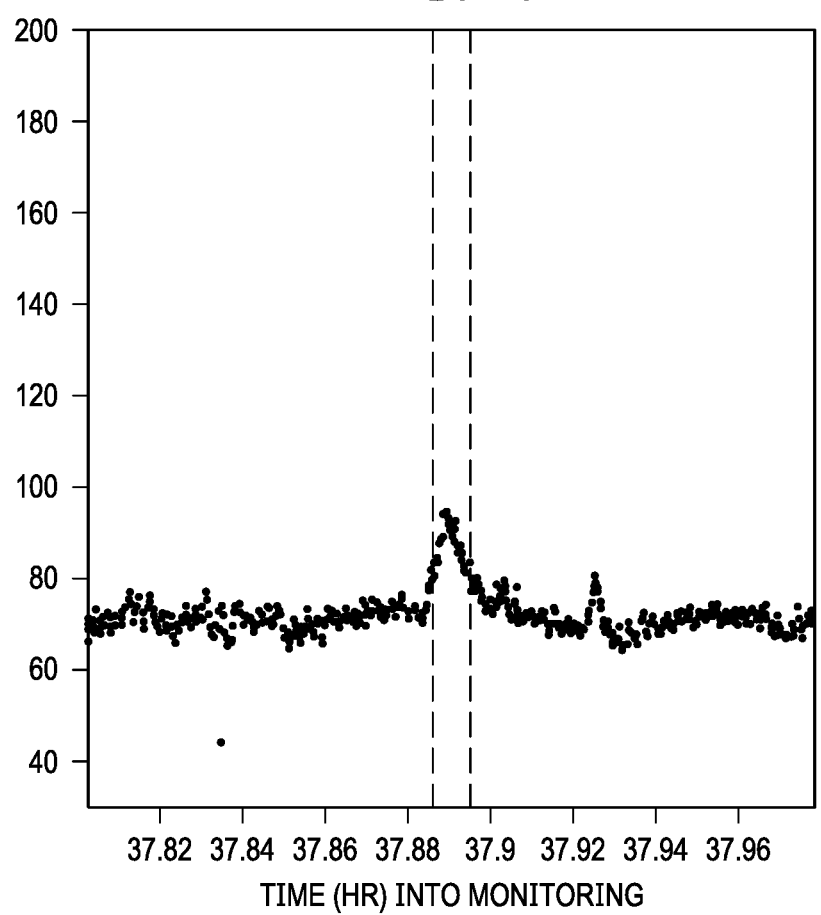
FIG. 27 shows a graph of heart rate (BPM) vs. time (hr), with an epileptic event identified by electrocorticography (ECOG) indicated by vertical lines, from which a triangle pattern is discernible, in accordance with an illustrative embodiment of the present disclosure.
Figure 28A:
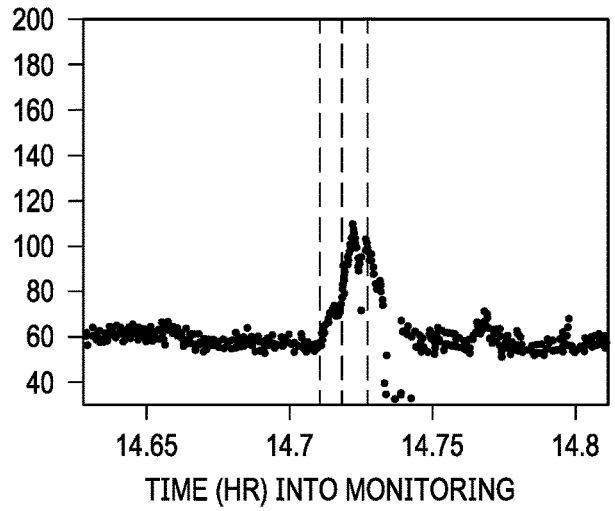
FIG. 28A shows a graph of heart rate vs. time, with epileptic events identified by ECoG indicated by vertical lines, from each of which a notched triangle pattern is discernible, in accordance with an illustrative embodiment of the present disclosure.
Figure 28B:
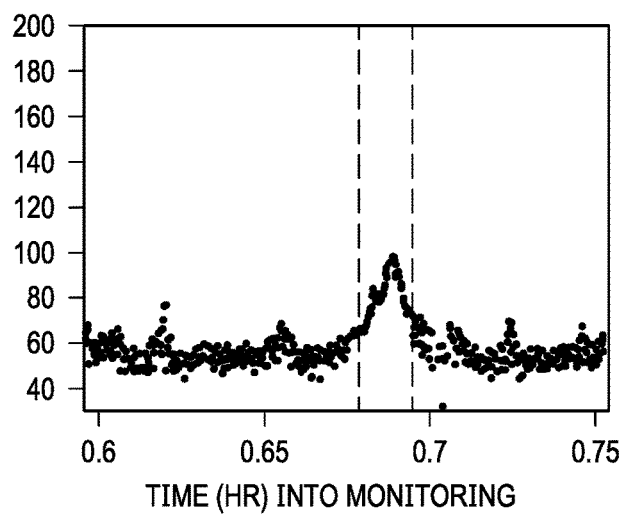
FIG. 28B shows a graph of heart rate vs. time, with epileptic events identified by ECoG indicated by vertical lines, from each of which a notched triangle pattern is discernible, in accordance with an illustrative embodiment of the present disclosure.
Figure 28C:
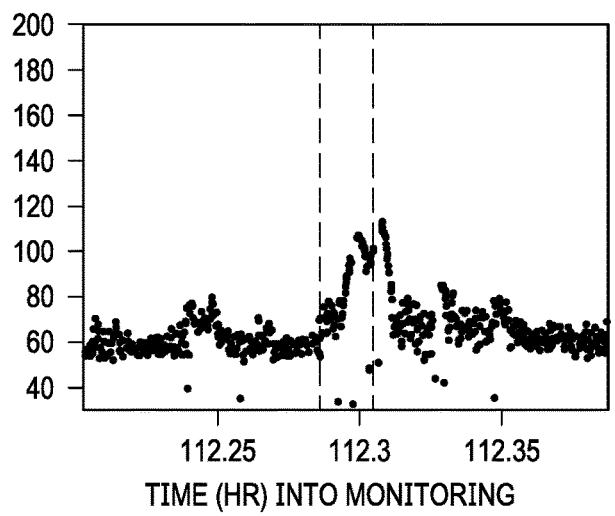
FIG. 28C shows a graph of heart rate vs. time, with epileptic events identified by ECoG indicated by vertical lines, from each of which a notched triangle pattern is discernible, in accordance with an illustrative embodiment of the present disclosure.
Figure 29C:
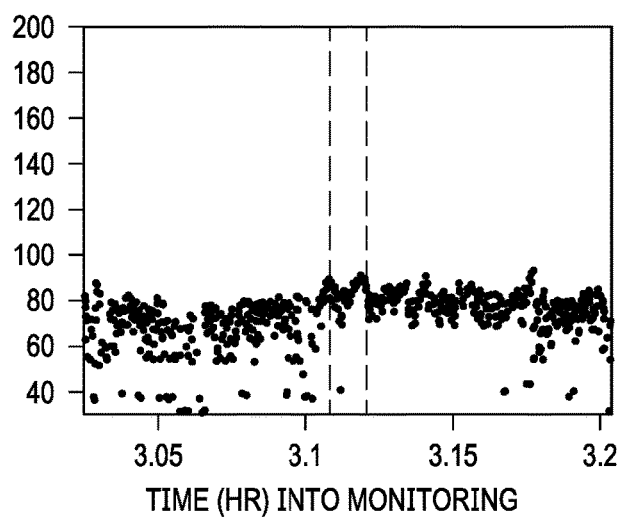
FIG. 29C shows a graph of heart rate vs. time, with epileptic events identified by ECoG indicated by vertical lines, from which an "M" pattern is discernible, in accordance with an illustrative embodiment of the present disclosure.
Figure 30:
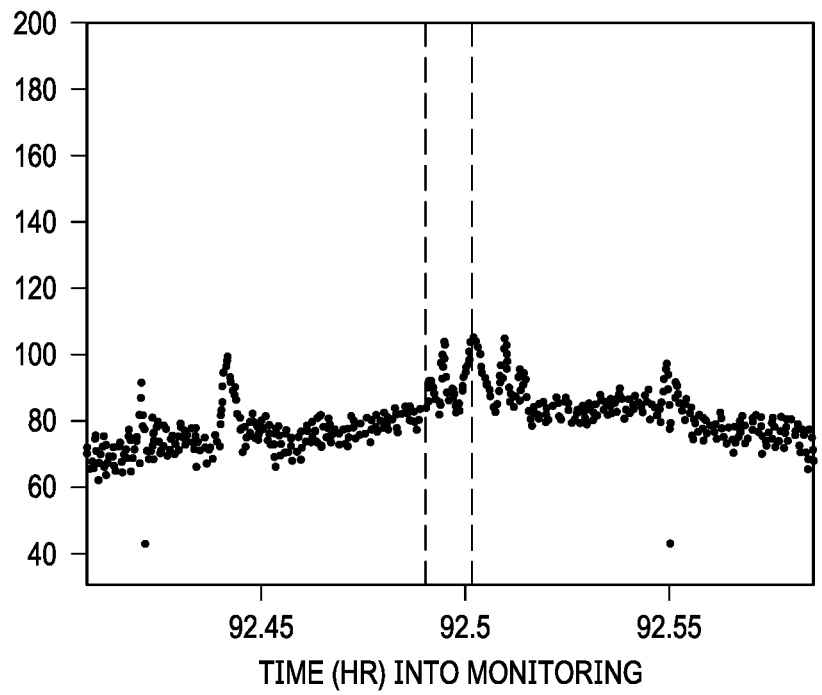
FIG. 30 shows a graph of heart rate vs. time, with an epileptic event identified by ECOG indicated by vertical lines, from which a "W" pattern is discernible, in accordance with an illustrative embodiment of the present disclosure.

Generally, the specific patterns or shapes can be considered as belonging to one of three categories:

Simple patterns, including the parabola shown in FIG. 26 or the triangle shown in FIG. 27, among others;

Complex patterns, including the notched triangle pattern of FIGS. 28A-28C, the "M" pattern of FIGS. 29A-29C, and the "W" pattern of FIG. 30, among others;

Polymorphic patterns, containing two or more simple and/or complex patterns, including fused simple and/or complex patterns, periodic or quasiperiodic oscillations, periodic or quasiperiodic oscillations overlaid on a longer term simple and/or complex patterns, and multiple simple and/or complex patterns, such as those shown in FIGS. 31-38B, among others.

Exemplary patterns or shapes are shown in FIGS. 27-38B. In each of these figures, a relevant portion of a graph of a patient's heart rate in beats per minute (BPM) vs. time in hours from the onset of ECOG monitoring of his or her seizure activity is shown. Vertical lines mark the electrographic onset and electrographic termination of a seizure.

The reader will have noticed that some patterns notable in FIGS. 27-38B as being closely correlated in time with a seizure also occur at times when no seizure was detected by ECoG. It should be pointed out that since monitoring of brain activity with intracranial electrodes is limited to certain regions, seizures may occur and go undetected if they originate in regions not monitored by the available electrodes. This may explain the presence of multiple heart rate patterns in the circumictal period when only one seizure was recorded. In other words, the cardiac data may indicate the occurrence of seizures that intracranial electrodes failed to detect. The use of cardiac information, such as the uses described and claimed herein, may supplement the inherent limitations of brain-based seizure detection.

FIG. 27 shows what may be termed a simple pattern, viz., a triangle, in accordance with an illustrative embodiment of the present disclosure. Herein, when discussing shapes, the words "triangle" and "parabola" can be used interchangeably. Generally, "triangle" will be used for convenience only.

FIG. 28A-C shows three graphs of what may be termed a notched triangle.

In various examples, the state change template may comprise one or more shapes that can be considered as comprising a plurality of triangles. For example, the state change template may comprise one or more shapes resembling letters of the Latin alphabet.

FIGS. 29A-C shows three graphs of what may be termed an "M" pattern, formed by two contiguous triangles or parabolae. The "M" pattern may be monophasic (the heart rate does not drop below the reference value or baseline) or multiphasic (after raising above the reference value, the heart rate drops below it). An "M" can be considered as distinct from a "notched triangle" in that the indentation of the M generally returns substantially to a baseline value and generally divides the M into substantially symmetrical halves.

The "M" patterns shown in FIGS. 29A-29C have total durations of about 60-90 seconds, beginning anywhere from about 15 seconds before electrographic onset to about 90 seconds after electrographic onset. However, other total durations and beginning times relative to electrographic onset may occur in other "M" patterns.

FIG. 30 shows a graph of what may be termed a "W" pattern, discernible from about 15 sec after electrographic onset to about 20 seconds after electrographic termination. Though not to be bound by theory, the "W" pattern may reflect differences (compared to the "M" pattern) in the timing of changes in autonomic influences during seizures.

The triangle, notched triangle, "M," and "W" patterns of FIGS. 27-30 can be considered to occur on a mesoscopic timescale. However, the same patterns may be discerned at shorter or longer timescales.

FIGS. 31-38B show patterns that can be considered to occur at long mesoscopic and/or macroscopic timescales. As can be seen and will be discussed below, the patterns of FIGS. 31-38B can generally be considered as polymorphic patterns comprising two or more of the basic shapes, simple patterns, or complex patterns discussed above.

Figure 31:
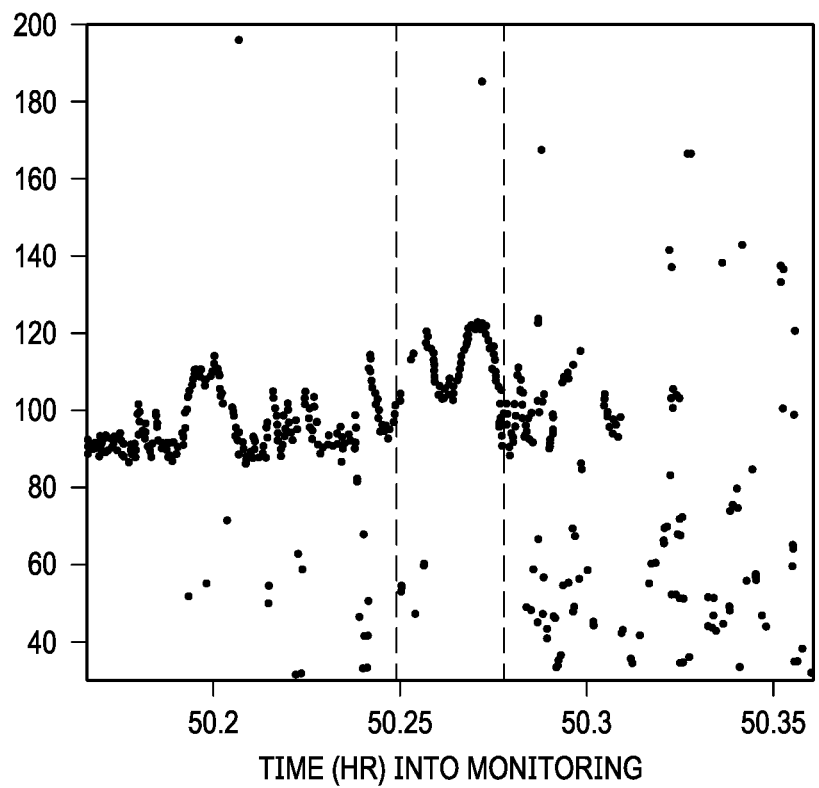
FIG. 31 shows a graph of heart rate vs. time, with an epileptic event identified by ECoG indicated by vertical lines, from which a fused "M" and "W" pattern is discernible, in accordance with an illustrative embodiment of the present disclosure.

FIG. 31 shows a fused "M" and "W" pattern. The "W" can be considered as starting at about 30 seconds before electrographic onset and ending at about 60-75 seconds after electrographic onset in the region of highest heart rate during the seizure event. The "M" can be considered as starting a few seconds before electrographic onset and ending about at electrographic termination. One may also discern a "W" occurring at a microscopic or short mesoscopic timescale at the notch of the "M."

Alternatively or in addition, a person of ordinary skill in the art, having the benefit of the present disclosure, may discern an "M" beginning at about 45-60 seconds before electrographic onset and ending at about the middle of the seizure, with a "W" beginning about 30 seconds after electrographic onset and ending about 15-30 seconds after electrographic termination.

Figure 32A:
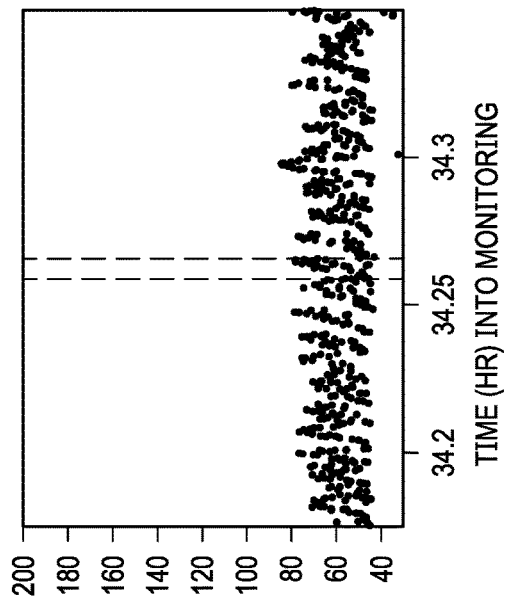
FIG. 32A shows a graph of heart rate vs. time, with epileptic events identified by ECoG indicated by vertical lines, from which a pattern of periodic oscillations is discernible, in accordance with an illustrative embodiment of the present disclosure.
Figure 32B:
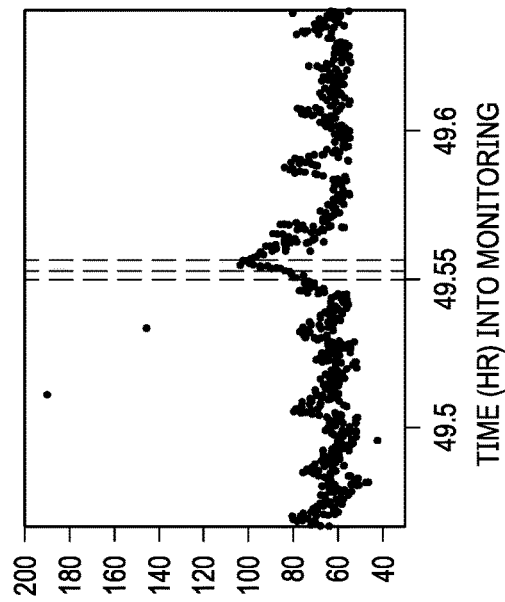
FIG. 32B shows a graph of heart rate vs. time, with epileptic events identified by ECoG indicated by vertical lines, from which a pattern of periodic oscillations is discernible, in accordance with an illustrative embodiment of the present disclosure.

FIGS. 32A-B shows two graphs of patterns of periodic or quasiperiodic oscillations. (For convenience, we will use the term "periodic," although it must be borne in mind that the frequency and the amplitude of the oscillations associated with a single seizure in one patient may vary over the course of about 10 minutes, as shown in FIGS. 32A-B. In other words, the term "periodic" is not limited herein to refer to series of oscillations with fixed frequency and amplitude).

The pattern of periodic oscillations may be deformed by a seizure event (e.g., FIG. 32B). In instances where this is not the case, a dysfunction of the patient's autonomic nervous system may be indicated. For example, FIG. 32A shows a rapid oscillation of the patient's heart rate by as much as 40 BPM in a short time.

Detecting a pattern in a preictal period in a time series of heart rate data may be considered, at least in some patients, as a "prediction" of a seizure and/or an indication of a period of greater risk of a seizure. Alternatively or in addition, it may be used to aid detection of seizures originating in brain regions not surveyed by intracranial electrodes.

Figure 33:
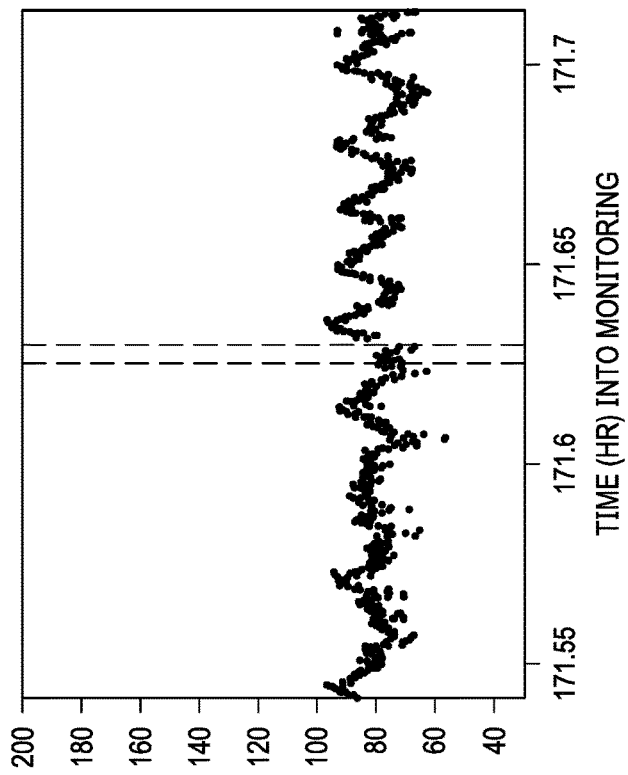
FIG. 33 shows a graph of heart rate vs. time, with an epileptic event identified by ECoG indicated by vertical lines, from which a pattern of periodic oscillations, specifically forming a sawtooth pattern, is discernible, in accordance with an illustrative embodiment of the present disclosure.

Multiple triangles with a certain degree of periodicity and either monophasic or biphasic nature can form what may be viewed as a "sawtooth" pattern in the circumictal period. FIG. 33 shows a graph of another pattern of periodic oscillations. The periodic oscillations from about 15-30 seconds after the seizure to about 3 minutes after the seizure can be considered a sawtooth pattern.

Figure 34B:
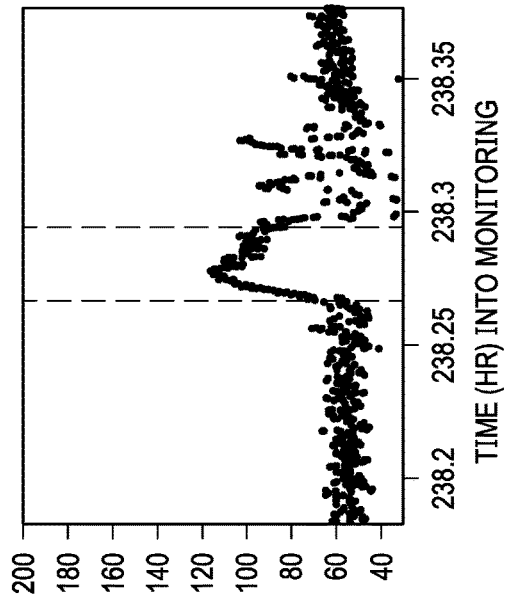
FIG. 34B shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present disclosure.
Figure 34D:
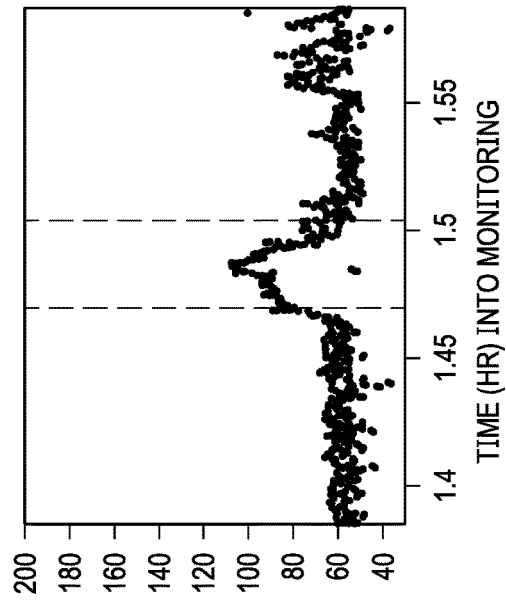
FIG. 34D shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present disclosure.
Figure 34A:
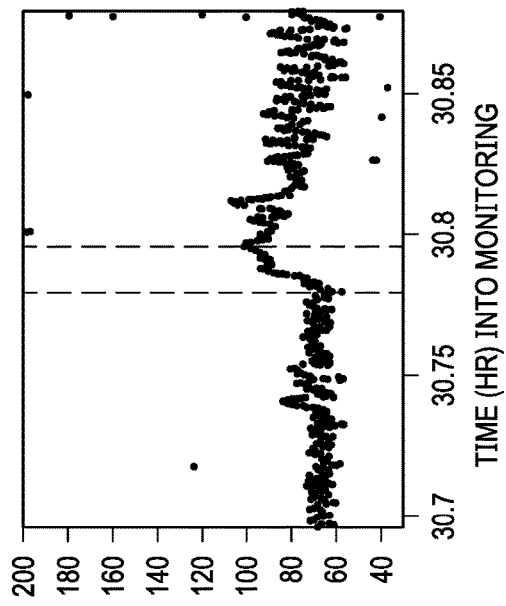
FIG. 34A shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present disclosure.
Figure 34C:
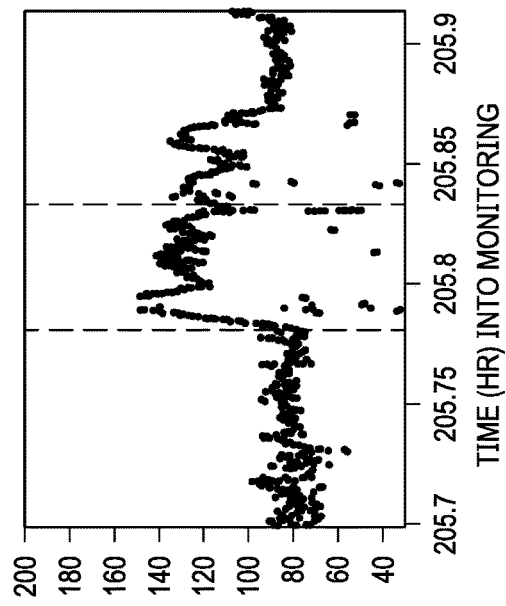
FIG. 34C shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present disclosure.

FIGS. 34A-D shows four graphs of patterns of periodic oscillations overlaid on a longer-timescale triangle pattern. For example, the pattern in FIG. 34A shows an asymmetric triangle with a trailing slope lasting about 5 minutes, on which is overlaid a pattern of periodic oscillations having an average wavelength of about 20 seconds is discernible from about 90 seconds after the seizure until the end of the window shown.

Figure 35:
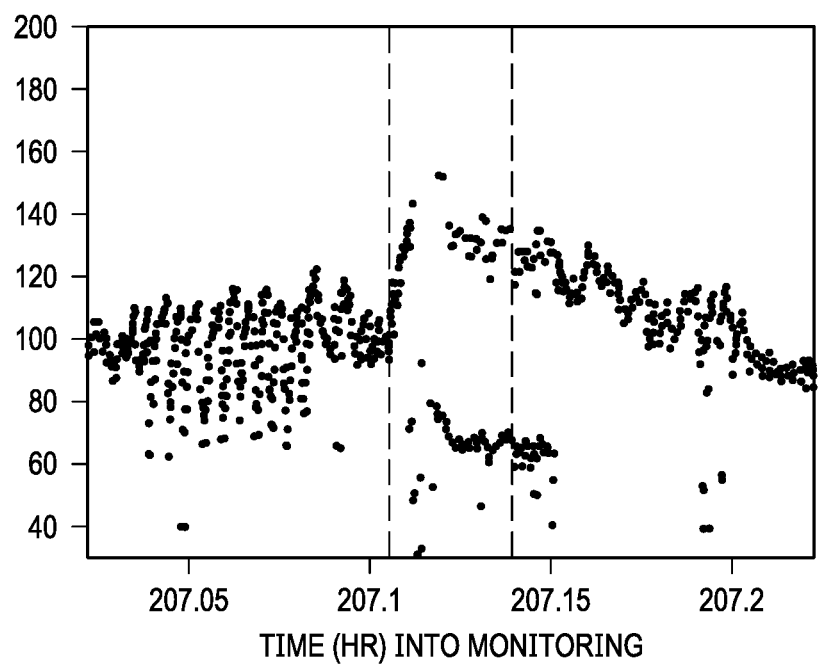
FIG. 35 shows a graph of heart rate vs. time, with an epileptic event identified by ECoG indicated by vertical lines, from which periodic oscillations forming a "comb" pattern are discernible, as well as a pattern of lower amplitude periodic oscillations overlaid on a longer-timescale triangle pattern is discernible, in accordance with an illustrative embodiment of the present disclosure.

FIG. 35 shows, in addition to a pattern of periodic oscillations overlaid in the post-ictal period on a longer-timescale triangle pattern, a comb pattern in the preictal period. For a duration of about 2.5 minutes starting about 3.5 minutes before electrographic onset, a pattern of periodic oscillations is shown with pronounced negative amplitudes (relative to the average heart rate over the first 30-45 seconds of the window) and an average wavelength of about 15 seconds. Again, detecting a pattern in a preictal period in a time series of heart rate data may be considered, at least in some patients, as a "prediction" of a seizure and/or an indication of a period of greater risk of a seizure. Alternatively or additionally, the presence of one pattern of long duration or more than one pattern of any duration in the circumictal period, are indicative of cardiac or autonomic instability. This information may be used to warn the patient or his caregiver(s) of an increased risk of a serious outcome and/or institute therapeutic measures.

Figure 36:
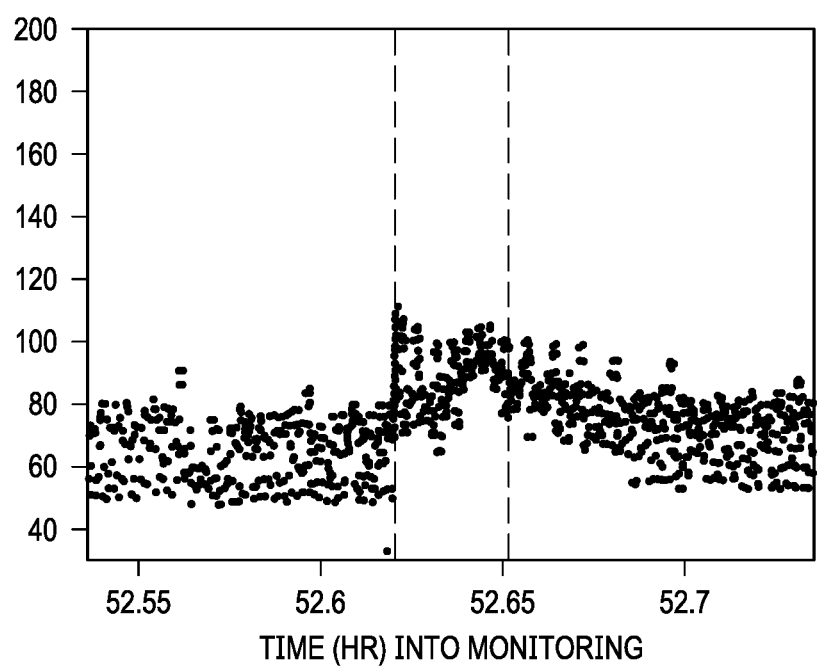
FIG. 36 shows a graph of heart rate vs. time, with an epileptic event identified by ECoG indicated by vertical lines, from which a pattern of periodic oscillations overlaid on a longer-timescale parabola pattern is discernible, in accordance with an illustrative embodiment of the present disclosure.

FIG. 36 shows another comb pattern, this one with pronounced positive amplitudes, overlaid on a longer-timescale parabola.

Figure 37:
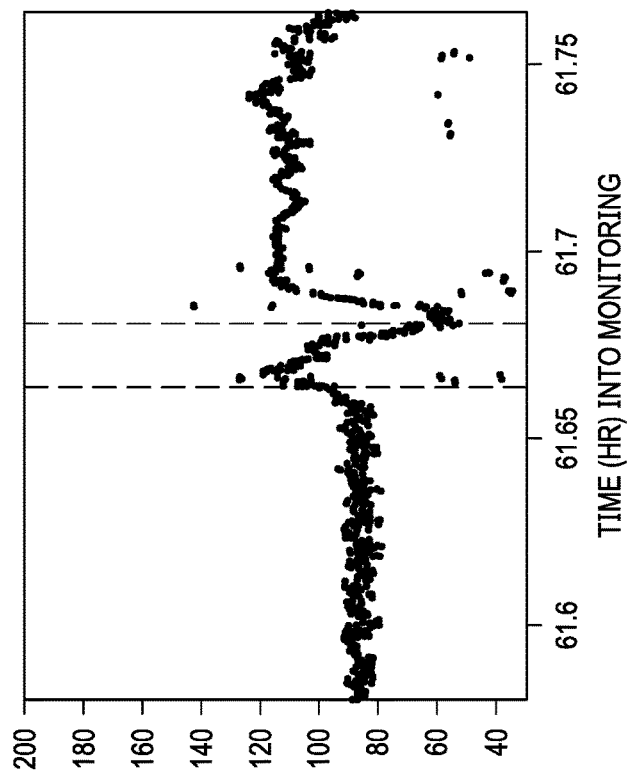
FIG. 37 shows a graph of heart rate vs. time, with an epileptic event identified by ECoG indicated by vertical lines, from which a triphasic pattern is discernible, in accordance with an illustrative embodiment of the present disclosure.

FIG. 37 shows a triphasic pattern relative to the preictal baseline, in which a first positive phase forms a notched triangle from just before electrographic onset until late in the seizure; a second, negative phase follows until about 30-45 seconds after the seizure; and a third, positive phase ensues with a duration of about 4 min until the end of the window.

Figure 38A:
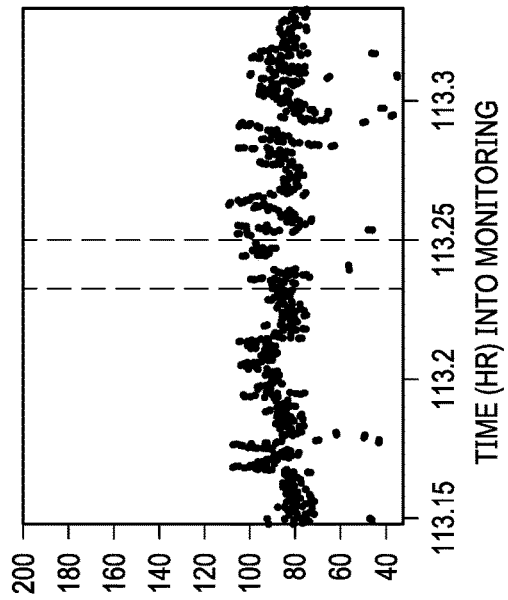
FIG. 38A shows a graph of heart rate vs. time, with epileptic events identified by ECOG indicated by vertical lines, from which multiple "M" and/or "W" patterns are discernible, in accordance with an illustrative embodiment of the present disclosure.
Figure 38B:
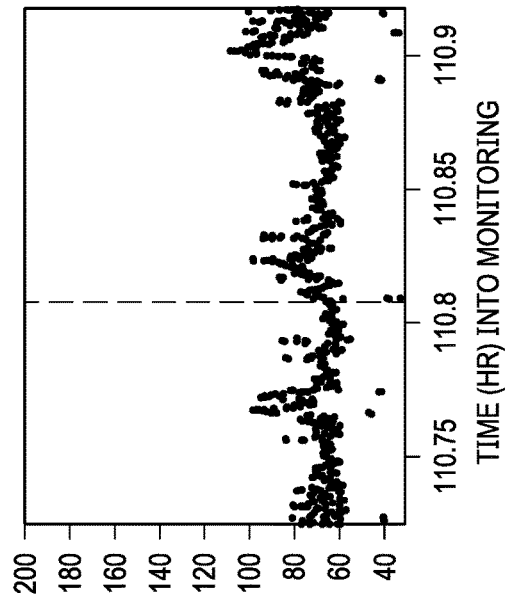
FIG. 38B shows a graph of heart rate vs. time, with epileptic events identified by ECoG indicated by vertical lines, from which multiple "M" and/or "W" patterns are discernible, in accordance with an illustrative embodiment of the present disclosure.

FIGS. 38A-B shows two graphs from which multiple "M" and/or "W" patterns are discernible in all three of the preictal, ictal, and postictal time periods. These multiple "M" and/or "W" patterns can be considered as part of a macroscopic pattern comprising a plurality of complex shapes.

In addition, very rapid oscillations in heart rate may also occur, and along with lower frequency oscillations, may provide useful insight into the behavior of heart rate variability circum-ictally and of its usefulness for seizure detection, given its differences from those observed outside the circum-ictal period. That is, oscillations at two frequencies (e.g., slow and fast) or more than two frequencies (e.g., very fast, slow, and very slow) may overlap to form a pattern that is commonly associated with a circumictal period.

Any one or more of the patterns shown in FIGS. 27-38B, among others, can be taken as the basis for a state change template. Also, HRV values can be derived from the time series of heart rates depicted in FIGS. 27-38B, and one or more distinctive patterns discernible from the HRV values can be used as the basis for a state change template. Such distinctive patterns would generally be expected to be distinct from HRV changes resulting from exercise or normal exertion.

Regardless of how HRV values are determined, in one embodiment, the pattern or shape of heart rate variability (as distinct from heart rate) measured at any or all of the timescales (micro-, meso-, or macroscopic) may be used as a template for detection and quantification of state changes using matched filtering or its autocorrelation function.

In a particular embodiment, the state change template comprises one phase relative to the reference heart rate parameter, three extrema, four directions of heart rate change, and two periods of increased heart rate relative to the reference heart rate parameter. This state change template may be considered to be the "M" pattern shown in FIGS. 29A-29C.

Multiple state change templates, including but not limited to multiple templates at different timescales, may be used for various purposes. For example, a first template found to have a particularly high sensitivity, specificity, or both can be used as a primary detection technique, with other templates used to validate detections made by the first template. For another example, a template found to have high sensitivity but low specificity (i.e., giving detections with a relatively high false positive rate) can be paired with another template found to have high specificity to be used in detections with higher sensitivity and specificity than either alone. For still another example, a first template can be used to identify a state change e.g., from a non-circumictal state to a preictal state, and this identification can be used to trigger use of a second template to identify a second state change, e.g., from a preictal state to an ictal state. For a particular example, a comb pattern can be used to identify a state change from a non-circumictal state to a preictal state, and an "M" pattern can be used to identify a state change from a preictal state to an ictal state.

In one embodiment, a plurality of matched filters (and/or the output of one or more of the matched filters as another matched filter or filters) can be used. For example, two or three matched filters, each on a separate one of the macroscopic, mesoscopic, and microscopic timescales can be run simultaneously on the time series of heart rate derivative data. After adequate analysis, comparisons of the results of matched filtering at the three times scales can be made to find the matched filter/timescale combination(s) giving highest sensitivity, highest specificity, fastest detection, or two or more thereof. Depending on the intended use, the most useful matched filter/timescale can then be used and run continuously and its output (detection) used to run the other matched filters/timescales for detection of changes (at longer or shorter time scales) and validation of detected changes.

Alternatively or in addition to the state change detections discussed herein, circumictal changes at various times scales may be used for assessment of disease state, both among circumictal changes monitored over long time periods (such as months or years) and between circumictal and non-circumictal states. In one embodiment, such disease state assessment may include assessment of the patient's risk of epilepsy-related sudden death (SUDEP).

Regardless of the desired use of circumictal data, circumictal changes may be quantified in one or more dimensions. In one embodiment, the output value of a detection, a disease state assessment, or the like can be monitored as a function of time (days, month years), both inter-circumictally and circumictally vs. non-circumictally, with the results analyzed for the presence of changes and trends. In another embodiment, circumictal changes can be classified as a function of pattern type (e.g., simple, complex, or polymorphic) and their temporal evolution tracked. In another embodiment, the temporal density of the circumictal period can be defined as percent time spent in a pattern(s).

Quantification of the match between the heart rate derivative shape and the state change template can also provide information about the duration of a seizure. In one embodiment, the method further comprises indicating the termination of the state change based upon a determination that the heart rate derivative shape fails to match the state change template, after an indication of an occurrence of a state change.

In one embodiment, the state change template further comprises at least one second characteristic selected from a magnitude of heart rate change relative to the reference heart rate parameter, a slope of heart rate change, a duration of one or more phases, a duration from a heart rate excursion from the reference heart rate parameter to a peak or a trough heart rate, a total duration of all the phases, or a duration of a constant slope of heart rate change; and indicating an occurrence of a state change is based upon a determination that the heart rate shape matches a state change template in both the at least one characteristic and in the at least one second characteristic.

The slope can be measured on any time scale, though for cardiac data, it may be smoother if taken over multiple beats, such as five or fifteen beats, or over a length of time, such as five to fifteen seconds. The term "constant slope" is used herein to refer to a fit, such as a least-squares fit or other fit, of the data series in question that has a sufficiently high fit to a straight line as to commend itself to the person of ordinary skill in the art as being a constant. For example, a region of a data series having a linear least-squares fit with an $R^2$ value of at least 0.9 can be considered to have a constant slope.

As stated above, a state change can be indicated by quantifying the match of the heart rate shape to the state change template. This state change indication can be considered as the sole indication of a state change, it can be validated by other techniques of state change identification, or it can be used to verify state changes indicated by other techniques. Such other techniques include those described elsewhere herein, as well as others known to the person of ordinary skill in the art or others the subject of one or more patent applications, such as U.S. patent application Ser. No. 12/770,562, filed Apr. 29, 2010; Ser. No. 12/771,727, filed Apr. 30, 2010; and Ser. No. 12/771,783, filed Apr. 30, 2010.

In one embodiment, the determination comprises using a first matched filter to yield a first output, building a second matched filter from the first output, and using the second matched filter to detect the state change. In other words, because the passage of a first matched filter over a data window will produce a stereotypical output when it begins passing over a shape which it matches, the stereotypical output itself can be used to detect a state change prior to, or as a validation of, a detection by the first matched filter.

Thus, in one embodiment, the method further comprises identifying an occurrence of a state change; and wherein said determining said heart rate derivative shape and said indicating are performed in response to said identifying, to validate said identifying.

In another embodiment, the method further comprises identifying an occurrence of a state change in response to said indicating, to validate said indicating. In a further embodiment, the method further comprises obtaining data relating to at least a portion of a heart beat complex from said patient; comparing said at least said portion of said heart beat complex with a corresponding portion of a reference heart beat complex template of said patient, wherein the reference heart beat complex template is not indicative of a state change; and validating said indicating an occurrence of a state change, wherein said validating is based upon a determination that said heart beat complex fails to match said reference heart beat complex template.

In one embodiment, the reference heart beat complex template is selected from a normal template (e.g., a reference heart beat complex template not indicative of a state change from a patient with healthy heart activity) or an abnormal template (e.g., a reference heart beat complex template not indicative of a state change from a patient with current or past unhealthy heart activity).

For example, a heart rate derivative shape present over a first timescale not typically found in a reference heart rate derivative shape observed during rising from lying to sitting, rising from sitting to standing, minor physical exertion, exercise, or emotionally-intense experiences can be used to indirectly validate an identification of a seizure made from a rise in heart rate, or vice versa.

Alternatively or in addition, in another embodiment, the method comprises determining a second reference heart rate parameter; determining a second heart rate derivative shape from said time series of cardiac data, wherein said second heart rate derivative shape comprises at least one second characteristic selected from a number of phases relative to said reference heart rate parameter, a number of positive phases relative to said reference heart rate parameter, a number of negative phases relative to said reference heart rate parameter, a number of extrema of said second heart rate derivative, or a number of directions of change of said second heart rate derivative; and validating said indicating an occurrence of a state change, wherein said validating is based upon a determination that said second heart rate derivative shape matches a second state change template in said at least one second characteristic.

The present disclosure also provides a method for indicating an occurrence of a state change, comprising obtaining data relating to at least a portion of a heart beat complex from a patient; comparing the at least the portion of the heart beat complex with a corresponding portion of a reference heart beat complex template of the patient; and indicating an occurrence of a state change based upon a determination that the heart beat complex fails to match the reference heart beat complex template.

Figure 39:
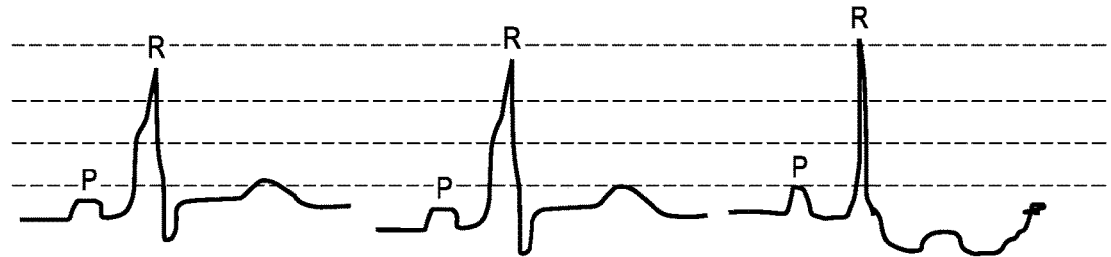
FIG. 39 shows exemplary heart beat complex changes detectable by use of the P wave and the R wave of a heart beat, in accordance with an illustrative embodiment of the present disclosure.

A heart beat complex is used herein to refer to a PQRST complex, as is known from the electrocardiogramart, from a single heart beat, including both the relative and absolute magnitudes of the P-, Q-, R-, S-, and T-waves, and all of the intervals P-Q, P-R, P-S, P-T, Q-R, Q-S, Q-T, R-S, R-T, and S-T. A portion of the heart beat complex is then any one or more of the relative and/or absolute magnitudes of the waves, their shapes, and/or one or more of the intervals between waves. A relative magnitude may be defined according to any one or more of the waves of the complex, e.g., an R-wave amplitude can be defined as r times the P-wave amplitude. FIG. 39 shows exemplary heart beat complexes with P- and R-waves identified by name. The horizontal lines are drawn for convenience, to point out plausible deviations between the various waves of different beat complex.

Although the term "a heart beat complex" is used above, a plurality, such as, but not necessarily, a sequential plurality, of heart beat complexes can be used, with the comparing being done for one or more of the plurality of heart beat complexes. The plurality may be a fixed set of beats or a moving window over a predetermined time or number of beats.

In one embodiment, the portion of the heart beat complex comprises at least one of an amplitude of a P wave, a polarity of a P wave, at least one of an amplitude of an R wave, a polarity of a Q wave, a polarity of an R wave, an amplitude of an S wave, a polarity of an S wave a polarity of an S wave, an amplitude of a T wave, a polarity of a T wave, an area under the curve of a P wave, an area under the curve of a Q wave, an area under the curve of an R wave, an area under the curve of an S wave, an area under the curve of a T wave, a width of a P wave, a with of a Q wave, a width of an n R wave, a width of an S wave, a width of a T wave, a morphology of a P wave, a morphology of a Q wave, a morphology of an R wave, a morphology of a T wave, a magnitude of a change in the distance from a P wave to a Q wave, a magnitude of a change in the distance from a P wave to an R wave, a magnitude of a change in the distance from a Q wave to an R wave, a magnitude of a change in the distance from an R wave to an S wave, a magnitude of a change in the distance from an R wave to a T wave, a magnitude of a change in the distance from an S wave to a T wave, a magnitude of an S-T segment elevation, a magnitude of an S-T segment depression, a magnitude of a Q-T segment elevation, a magnitude of a Q-T segment depression, a P-R interval, an R-S interval, an S-T interval, an R-T interval, and a Q-T interval.

The reference heart beat complex template can be derived from any non-state change heart beats. Such beats may be one, some, or all the same beats used to define the reference heart rate parameter and/or reference HRV described above, but need not be any of the same beats. In one embodiment, the reference heart beat complex template comprises at least one matched filter. In a further embodiment, the heart beat complex fails to match the reference heart beat complex template if a matched filter score for the heart beat complex to the at least one matched filter is less than a heart beat complex value threshold.

Although one reference heart beat complex template is referred to above, a plurality of reference heart beat complexes may be used. For example, a plurality of reference heart beat complexes can be used on the same heart beats, or one or more of the plurality can be used at different times of day, under different states of exertion or arousal, in view of changes in heart health histories or differences in heart health between patients, among other possibilities. In one embodiment, a second reference heart beat complex template comprises at least one of T wave depression, P-Q segment elongation, another abnormality, or two or more thereof, relative to the canonical "normal" heart beat complex.

Alternatively, one or more heart beat complex templates derived from heart beat complexes observed during one or more periods of state change may be used, with a state change declared if the heart beat complex(es) match(es) the state change heart beat complex template(s).

Figure 40A:
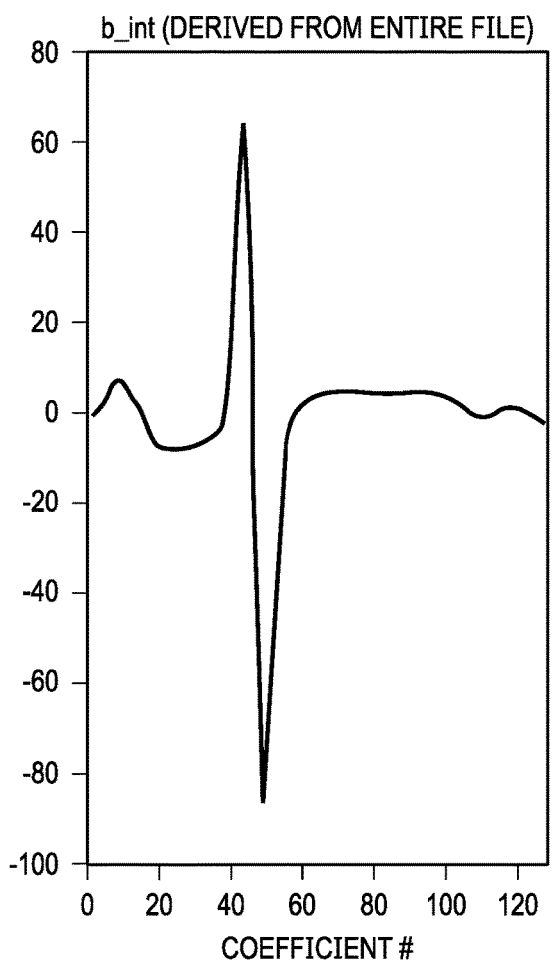
FIGS. 40A-B show a first heart beat complex derived from data collected over an entire period of EKG monitoring of a patient (A) and a second heart beat complex derived from EKG data collected from the same patient during circumictal periods only (B).
Figure 40B:
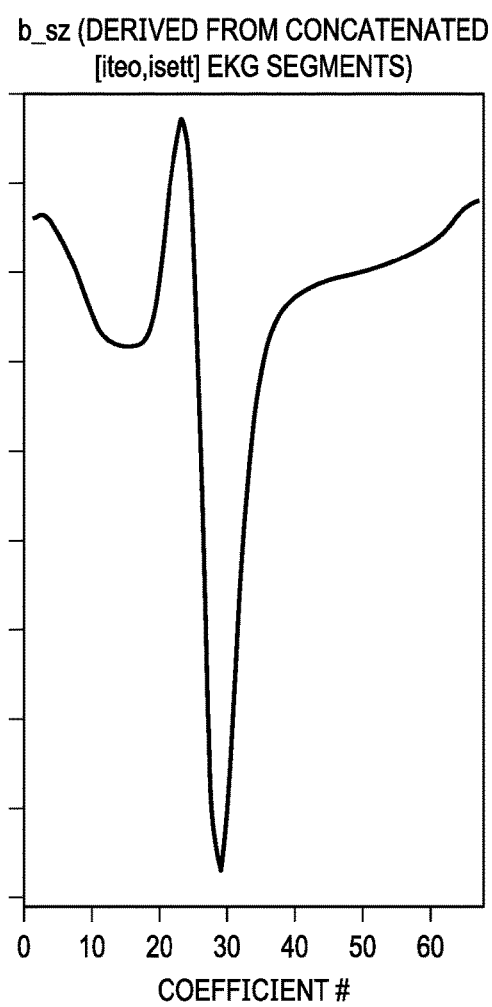

FIG. 40A shows an exemplary heart beat complex derived from data collected over an entire period of EKG monitoring of a patient, which may be used as a reference heart beat complex template. FIG. 40B shows an exemplary heart beat complex derived from EKG data collected from the same patient during circumictal periods only, which may be used as a state change heart beat complex template.

In the event a plurality of reference heart beat complex templates are used, one or more of the templates may be modified over time, based on observed changes in the patient's heart beat complexes, such as during non-state-change periods.

The at least portion of the heart beat complex and the corresponding portion of the reference heart beat complex template can be compared using any of the pattern matching techniques described herein. Because the reference heart beat complex template is taken from non-seizure heart beats, a failure to match between the at least portion of the heart beat complex and the corresponding portion of the reference heart beat complex template is an indirect indication of a seizure.

Quantification of the match between a portion of a heart beat complex and the corresponding portion of the reference heart beat complex template can also provide information about the duration of a seizure. In one embodiment, the method further comprises obtaining a time series of data relating to a plurality of heart beat complexes from the patient; comparing at least a portion of each of a sequential plurality of heart beat complexes with a corresponding portion of the first reference heart beat complex template; and indicating the termination of the state change based upon a determination that at least one heart beat complex of the sequential plurality matches the reference heart beat complex template, after an indication of an occurrence of a state change. Matched filters can be used in this determination, as described elsewhere herein.

In one embodiment, the determination further comprises analyzing one or more of a pulse shape, an R wave amplitude, an apex cardiogram, or a pressure wave, to validate or classify the state change.

In one embodiment, a heart beat complex fails to match a reference heart beat complex template if a matched filter output for said heart beat complex is less than a first matched filter threshold, or differs from a second matched filter threshold by at least a predetermined magnitude.

Also similarly to the heart rate derivatives described above, a state change can be indicated by quantifying the match of the portion of the heart beat complex to the reference heart beat complex template. This state change indication can be considered as the sole indication of a state change, it can be validated by other techniques of state change identification, or it can be used to verify state changes indicated by other techniques. Such other techniques include those described elsewhere herein, as well as others known to the person of ordinary skill in the art or others the subject of one or more patent applications, such as U.S. patent application Ser. No. 12/770,562, filed Apr. 29, 2010; Ser. No. 12/771,727, filed Apr. 30, 2010; and Ser. No. 12/771,783, filed Apr. 30, 2010.

Thus, in one embodiment, the method further comprises identifying an occurrence of a state change; wherein the obtaining, the comparing, and the indicating are performed in response to the identifying, to validate the identifying.

Particularly, the prior indicating can be performed using heart rate or HRV data, and in one embodiment, one or more heart beats taken from the reference heart rate parameter of the heart rate or HRV data can be used to define the reference heart beat complex template and one or more heart beats taken from the excursion of the heart rate or HRV data from its reference heart rate parameter can be used to as the heart beat complex from which a portion is matched with a corresponding portion from the reference heart beat complex template. By "zooming" from the heart rate or HRV shape into one or more individual heart beats giving rise to the heart rate or HRV shape, a state change indication from HRV data can be validated. For example, if the heart rate or HRV shape gives an indication of a state change, but one or more heart beat complexes from the putative state change match the reference heart beat complex template, the excursion of heart rate or HRV from the reference heart rate parameter may be considered to result from exercise or another non-seizure-event source.

In another embodiment, the method further comprises identifying an occurrence of a state change in response to said indicating, to validate said indicating. For example, identifying an occurrence of a state change to validate an indication can be performed by using a prior detection algorithm, using a second characteristic of the state change template, or matching at least a portion of a heart beat complex with a corresponding portion from a reference heart beat complex template, among other techniques.

The present disclosure also provides a method for identifying a state change template from cardiac data, comprising obtaining a time series of cardiac data from a patient during a first time window; determining a time of occurrence of at least one state change suffered by the patient during the first time window; and either (i) determining at least one state change template in the time series of cardiac data within the first time window and timewise correlated with the at least one state change, wherein the at least one state change template comprises at least one characteristic selected from a number of phases relative to a reference heart rate parameter, a number of extrema, a number of directions of change, a number of positive phases relative to said reference heart rate parameter, or a number of negative phases relative to said reference heart rate parameter, or (ii) determining at least one reference heart beat complex template in the time series of cardiac data within the first time window and not timewise correlated with the at least one state change.

In a particular embodiment, the at least one characteristic comprises at least one of the amplitude of at least one phase, the duration of at least one phase, the valence (positive or negative) of at least one phase, at least one slope of at least one phase, the arc length of at least one phase, the number of extrema in at least one phase, and the sharpness of the extrema of at least one phase.

The cardiac data can comprise one or more of heart rate data, HRV data, or heart beat complex data, such as data from at least a portion of each of a plurality of heart beat complexes, among others. The cardiac data can be derived from signals collected from or related to EKG, heart sounds (such as can be collected by a microphone mounted on the skin of the chest), blood pressure, apex cardiography, echocardiography, thermography, or blood flow velocities estimated by Doppler imaging, among other techniques known to the person of ordinary skill in the art.

The time of occurrence of the at least one state change can be determined by any appropriate technique, such as EEG, cardiac-based seizure detection (such as that disclosed in U.S. patent application Ser. No. 12/770,562, filed Apr. 29, 2010; Ser. No. 12/771,727, filed Apr. 30, 2010; and Ser. No. 12/771,783, filed Apr. 30, 2010), testing of the patient's responsiveness (such as that disclosed in U.S. patent application Ser. No. 12/756,065, filed Apr. 7, 2010, the disclosure of which is hereby incorporated herein by reference), among other techniques known to the person of ordinary skill in the art or otherwise available.

The finding of a timewise correlation of at least one state change template with a state change, or the finding of a non-timewise correlation of at least one reference heart beat complex template with a state change, can be performed by any appropriate technique. "Timewise correlation" refers to any substantially repeated duration between a putative template and a state change, and includes putative templates taking place before a state change, during a state change, or after a state change.

The state change template can be further defined according to at least one second characteristic selected from a magnitude of cardiac data value change relative to the reference heart rate parameter cardiac data series, a slope of cardiac data value change, a duration of one or more phases, a duration from a cardiac data excursion from the reference heart rate parameter cardiac data series to a peak or a trough cardiac data series, a total duration of a cardiac data excursion from the reference heart rate parameter cardiac data series, or a duration of a constant slope of cardiac data series change.

In another embodiment, the present disclosure relates to a method for determining at least one property of a pattern indicative of an occurrence of a state change. In one embodiment, this method comprises obtaining a time series of cardiac data from a patient; determining if at least one heart rate derivative shape forms at least one pattern; and determining at least one property of the pattern.

For example, in one embodiment, the at least one property of the pattern comprises a shape of the pattern, a time of occurrence of the pattern, a time elapsed between occurrences of the pattern, and an association of the pattern with a state change of a body organ.

Any state change of any body organ may be considered. In one embodiment, the at least one property of the pattern is an association of the pattern with a state change of the brain. In a further embodiment, the state change of the brain is an epileptic seizure.

The state change template or reference heart beat complex template produced by the present method can be used in a method as described above.

However the state change is identified, and regardless of the state change template, the timescale, and the subperiod of the circumictal period in which state changes are detected, in some embodiments, an indication of a state change can be used as the basis for taking a responsive action selected from warning, logging the time of a state change, computing and storing one or more state change severity indices, treating the state change, or two or more thereof. In one embodiment, quantification of one or more state change severity indices can be performed through comparisons of matched filtering outputs, although scaling and/or other appropriate transformation may be required when the shapes are similar but their sizes are not.

A state change warning may be given as, for example, a warning tone or light, vibration, pressure, or scent implemented by a medical device or a device adapted to receive indications of the state change; as an automated email, text message, telephone call, or video message sent from a medical device or a unit in communication with a medical device to the patient's cellular telephone, PDA, computer, television, 911 or another emergency contact number for paramedic/EMT services, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

The time may be logged by receiving an indication of the current time and associating the indication of the current time with an indication of the state change.

State change severity indices may be calculated and stored by appropriate techniques and apparatus.

In an exemplary embodiment of the present disclosure, any method of indicating a seizure can further comprise taking a responsive action based upon the identifying the state change. The responsive action may include providing a warning and/or notifying the patient or a caregiver, logging the time of a state change, computing and storing one or more state change severity indices, or treating the state change.

In one embodiment of the present disclosure, treating the state change comprises providing a neurostimulation therapy. The neurostimulation therapy may involve applying an electrical, mechanical, magnetic, electro-magnetic, photonic, acoustic, cognitive, sensori-perceptual and/or chemical signal to a neural structure of the body. The neural structure may be a brain, a spinal cord, a peripheral nerve, a cranial nerve, or another neural structure. In a particular embodiment, the responsive action comprises treating the state change by providing a cranial nerve stimulation therapy. Cranial nerve stimulation has been proposed to treat a number of medical conditions pertaining to or mediated by one or more structures of the nervous system, including epilepsy, movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode. In one embodiment, the treatment comprises at least one of applying an electrical signal to a neural structure of a patient; delivering a drug to a patient; or cooling a neural structure of a patient. When the treatment comprises applying an electrical signal to a portion of a neural structure of a patient, the neural structure may be at least one of a portion of a brain structure of the patient, a portion of a cranial nerve of a patient, a portion of a spinal cord of a patient, a portion of a sympathetic nerve structure of the patient, a portion of a parasympathetic nerve structure of the patient, and/or a portion of a peripheral nerve of the patient.

The above methods can be performed alone. In one embodiment, the above methods can be performed in combination with a continuous or open-loop therapy for epilepsy. In one embodiment, the above methods are performed to take action in response to an indication of a state change, and at all or most other times, a chronic therapy signal is applied to a target structure in the patient's body. In one embodiment, the target structure is a cranial nerve, such as the vagus nerve.

Figure 22:
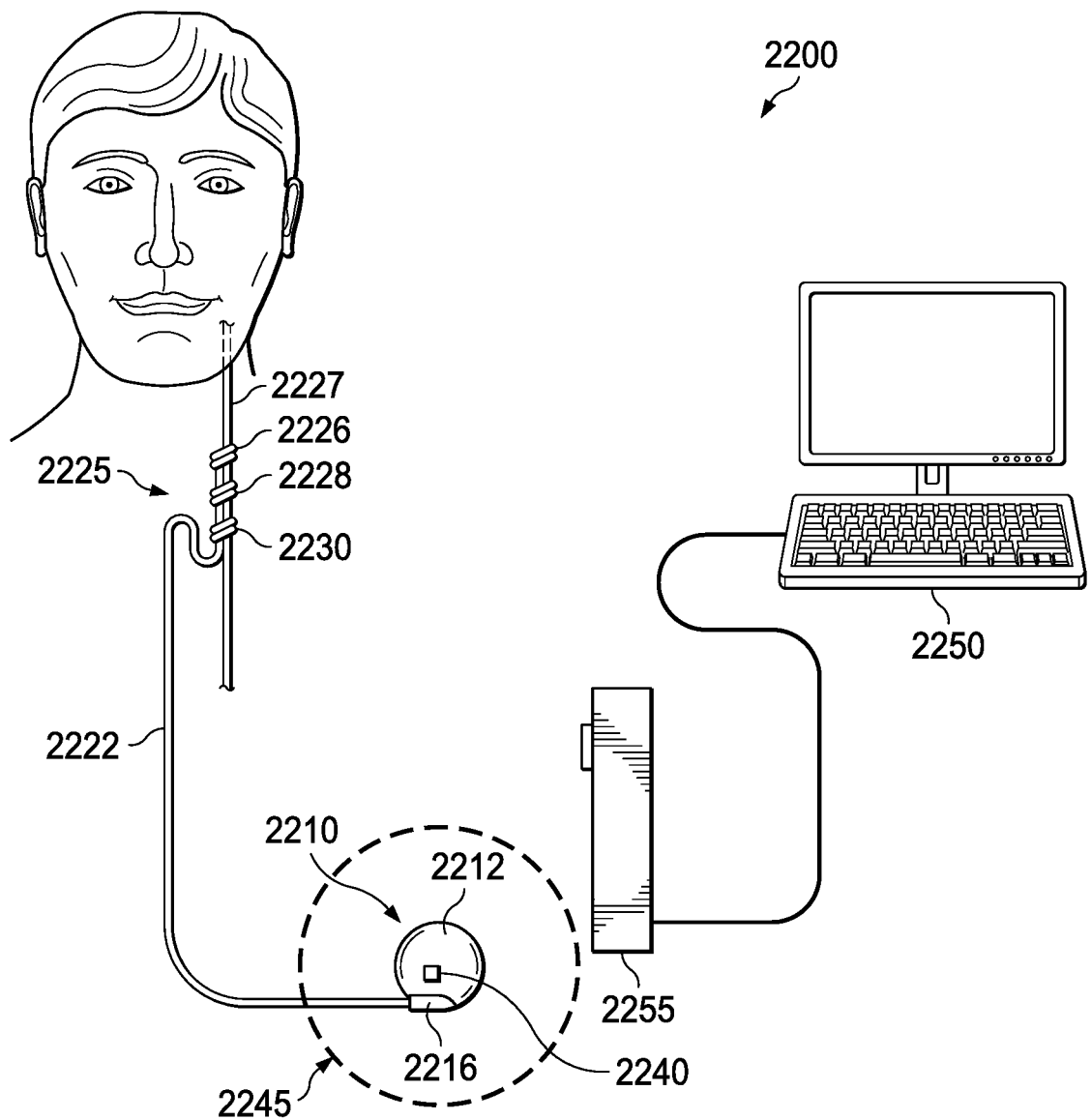
FIG. 22 provides a stylized diagram of a medical device implanted into a patient's body for providing a therapeutic electrical signal to a neural structure of the patient's body, in accordance with one illustrative embodiment of the present disclosure.

Although not limited to the following, an exemplary system capable of implementing embodiments of the present disclosure is described below. FIG. 22 depicts a stylized implantable medical system (IMD) 2200 for implementing one or more embodiments of the present disclosure. An electrical signal generator 2210 is provided, having a main body 2212 comprising a case or shell with a header 2216 for connecting to an insulated, electrically conductive lead assembly 2222. The generator 2210 is implanted in the patient's chest in a pocket or cavity formed by the implanting surgeon just below the skin (indicated by a dotted line 2245), similar to the implantation procedure for a pacemaker pulse generator.

A nerve electrode assembly 2225, preferably comprising a plurality of electrodes having at least an electrode pair, is conductively connected to the distal end of the lead assembly 2222, which preferably comprises a plurality of lead wires (one wire for each electrode). Each electrode in the electrode assembly 2225 may operate independently or alternatively, may operate in conjunction with the other electrodes. In one embodiment, the electrode assembly 2225 comprises at least a cathode and an anode. In another embodiment, the electrode assembly comprises one or more unipolar electrodes.

Lead assembly 2222 is attached at its proximal end to connectors on the header 2216 of generator 2210. The electrode assembly 2225 may be surgically coupled to the vagus nerve 2227 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 2225 comprises a bipolar stimulating electrode pair 2226, 2228 (i.e., a cathode and an anode). Suitable electrode assemblies are available from Cyberonics, Inc., Houston, Texas, USA as the Model 302 electrode assembly. However, persons of skill in the art will appreciate that many electrode designs could be used in the present disclosure. In one embodiment, the two electrodes are wrapped about the vagus nerve, and the electrode assembly 2225 may be secured to the vagus nerve 2227 by a spiral anchoring tether 2230 such as that disclosed in U.S. Pat. No. 4,979,511, issued Dec. 25, 1990 to Reese S. Terry, Jr. Lead assembly 2222 may be secured, while retaining the ability to flex with movement of the chest and neck, by a suture connection to nearby tissue (not shown).

In alternative embodiments, the electrode assembly 2225 may comprise temperature sensing elements, blood pressure sensing elements, and/or heart rate sensor elements. Other sensors for other body parameters may also be employed. Both passive and active stimulation may be combined or delivered by a single IMD according to the present disclosure. Either or both modes may be appropriate to treat a specific patient under observation.

The electrical pulse generator 2210 may be programmed with an external device (ED) such as computer 2250 using programming software known in the art. A programming wand 2255 may be coupled to the computer 2250 as part of the ED to facilitate radio frequency (RF) communication between the computer 2250 and the pulse generator 2210. The programming wand 2255 and computer 2250 permit non-invasive communication with the generator 2210 after the latter is implanted. In systems where the computer 2250 uses one or more channels in the Medical Implant Communications Service (MICS) bandwidths, the programming wand 2255 may be omitted to permit more convenient communication directly between the computer 2250 and the pulse generator 2210.

Figure 23A:
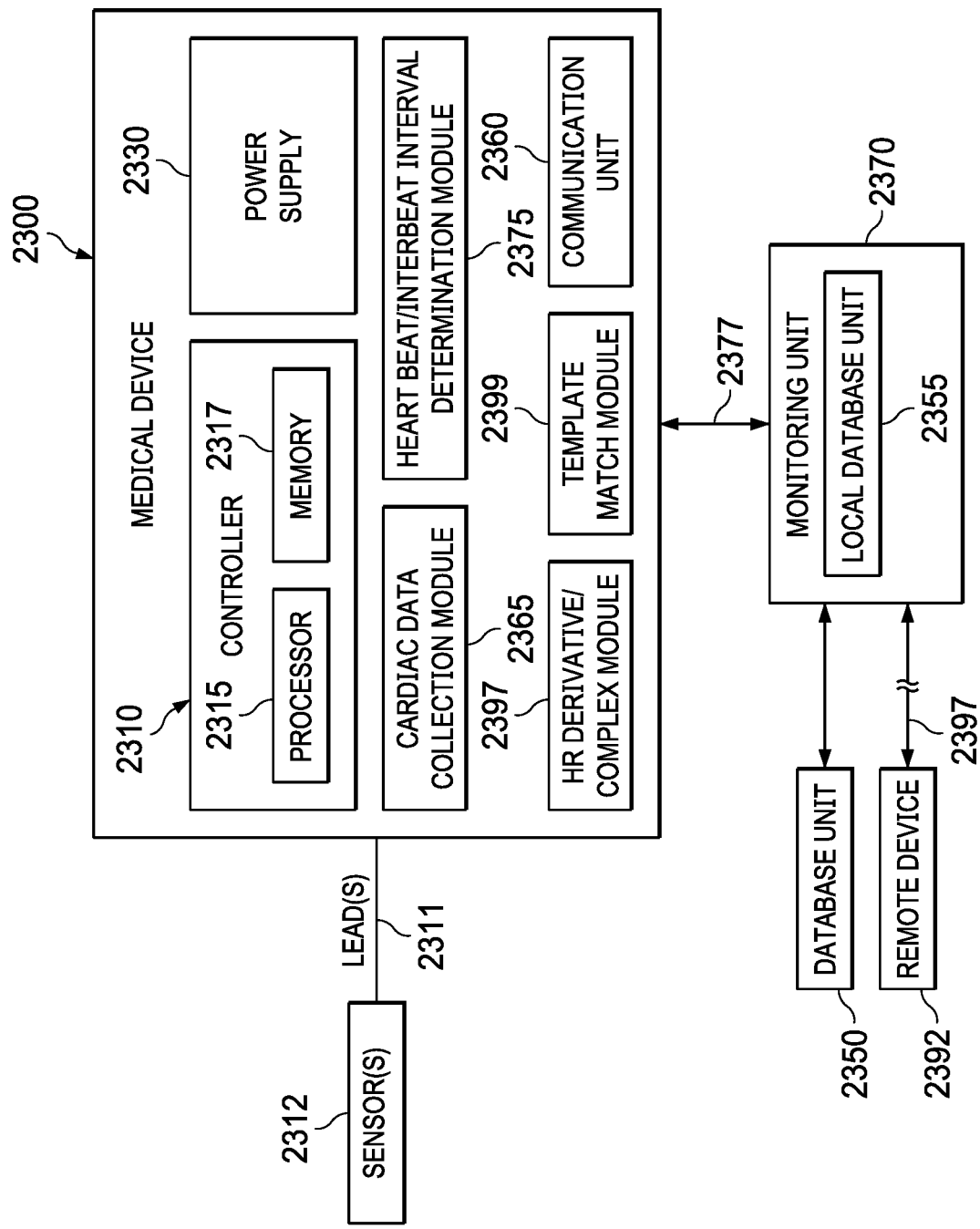
FIG. 23A is a block diagram of a medical device system that includes a medical device and an external unit, in accordance with one illustrative embodiment of the present disclosure.

Turning now to FIG. 23A, a block diagram depiction of a medical device 2300 is provided, in accordance with one illustrative embodiment of the present disclosure.

In some embodiments, the medical device 2300 may be implantable (such as implantable electrical signal generator 2210 from FIG. 22), while in other embodiments the medical device 2300 may be completely external to the body of the patient.

The medical device 2300 (such as generator 2210 from FIG. 22) may comprise a controller 2310 capable of controlling various aspects of the operation of the medical device 2300. The controller 2310 is capable of receiving internal data or external data, and in one embodiment, is capable of causing a stimulation unit 2320 (FIG. 23B) to generate and deliver an electrical signal to target tissues of the patient's body for treating a medical condition. For example, the controller 2310 may receive manual instructions from an operator externally, or may cause the electrical signal to be generated and delivered based on internal calculations and programming. In other embodiments, the medical device 2300 does not comprise a stimulation unit 2320 (FIG. 23A). In either embodiment, the controller 2310 is capable of affecting substantially all functions of the medical device 2300.

The controller 2310 may comprise various components, such as a processor 2315, a memory 2317, etc. The processor 2315 may comprise one or more microcontrollers, microprocessors, etc., capable of performing various executions of software components. The memory 2317 may comprise various memory portions where a number of types of data (e.g., internal data, external data instructions, software codes, status data, diagnostic data, etc.) may be stored. The memory 2317 may comprise one or more of random access memory (RAM), dynamic random access memory (DRAM), electrically erasable programmable read-only memory (EEPROM), flash memory, etc.

Figure 23B:
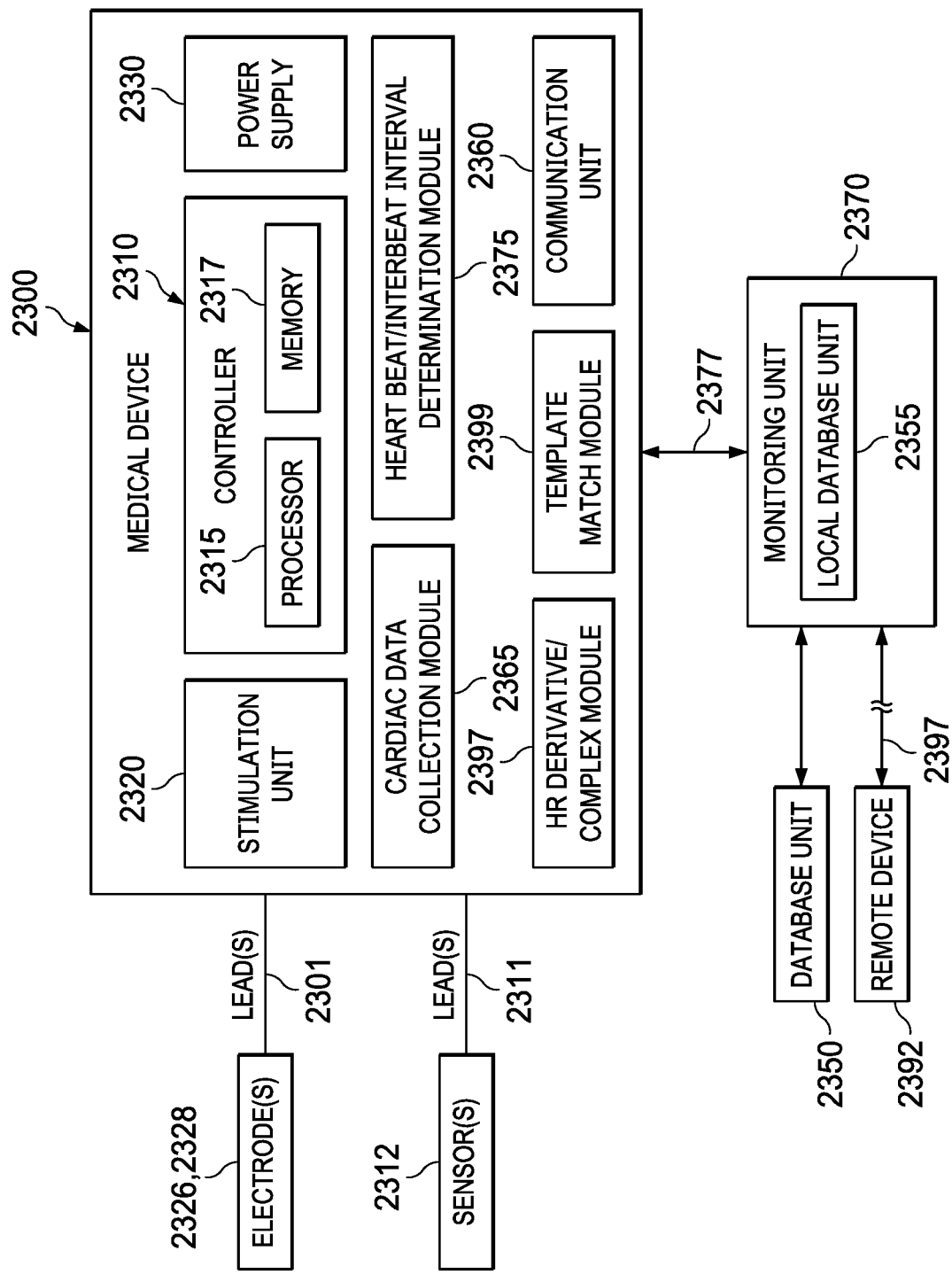
FIG. 23B is a block diagram of a medical device system that includes a medical device and an external unit, in accordance with one illustrative embodiment of the present disclosure.

As stated above, in one embodiment, the medical device 2300 may also comprise a stimulation unit 2320 capable of generating and delivering electrical signals to one or more electrodes 1326, 1328 via leads 2301 (FIG. 23B). A lead assembly such as lead assembly 2222 (FIG. 22) may be coupled to the medical device 2300. Therapy may be delivered to the leads 2301 comprising the lead assembly 2222 by the stimulation unit 2320 based upon instructions from the controller 2310. The stimulation unit 2320 may comprise various circuitry, such as electrical signal generators, impedance control circuitry to control the impedance "seen" by the leads, and other circuitry that receives instructions relating to the delivery of the electrical signal to tissue. The stimulation unit 2320 is capable of delivering electrical signals over the leads 2301 comprising the lead assembly 2222. As should be apparent, in certain embodiments, the medical device 2300 does not comprise a stimulation unit 2320, lead assembly 2222, or leads 2301.

In other embodiments, a lead 2301 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 2300 may also comprise a power supply 2330. The power supply 2330 may comprise a battery, voltage regulators, capacitors, etc., to provide power for the operation of the medical device 2300, including delivering the therapeutic electrical signal. The power supply 2330 comprises a power source that in some embodiments may be rechargeable. In other embodiments, a non-rechargeable power source may be used. The power supply 2330 provides power for the operation of the medical device 2300, including electronic operations and the electrical signal generation and delivery functions. The power supply 2330 may comprise a lithium/thionyl chloride cell or a lithium/carbon monofluoride (LiCFx) cell if the medical device 2300 is implantable, or may comprise conventional watch or 9V batteries for external (i.e., non-implantable) embodiments. Other battery types known in the art of medical devices may also be used.

The medical device 2300 may also comprise a communication unit 2360 capable of facilitating communications between the medical device 2300 and various devices. In particular, the communication unit 2360 is capable of providing transmission and reception of electronic signals to and from a monitoring unit 2370, such as a handheld computer or PDA that can communicate with the medical device 2300 wirelessly or by cable. The communication unit 2360 may include hardware, software, firmware, or any combination thereof.

The medical device 2300 may also comprise one or more sensor(s) 2312 coupled via sensor lead(s) 2311 to the medical device 2300. The sensor(s) 2312 are capable of receiving signals related to a physiological parameter, such as the patient's heart beat, blood pressure, and/or temperature, and delivering the signals to the medical device 2300. In one embodiment, the sensor(s) 2312 may be the same as implanted electrode(s) 2226, 2228 (FIG. 22). In other embodiments, the sensor(s) 2312 are external structures that may be placed on the patient's skin, such as over the patient's heart or elsewhere on the patient's torso.

In one embodiment, the medical device 2300 may comprise a cardiac data collection module 2365 that is capable of collecting cardiac data comprising fiducial time markers of each of a plurality of heart beats. The cardiac data collection module 2365 may also process or condition the cardiac data. The cardiac data may be provided by the sensor(s) 2312. The cardiac data collection module 2365 may be capable of performing any necessary or suitable amplifying, filtering, and performing analog-to-digital (A/D) conversions to prepare the signals for downstream processing. The cardiac data collection module, in one embodiment, may comprise software module(s) that are capable of performing various interface functions, filtering functions, etc., to process fiducial time markers of each of a plurality of heart beats. In another embodiment the cardiac data collection module 2365 may comprise hardware circuitry that is capable of performing these functions. In yet another embodiment, the cardiac data collection module 2365 may comprise hardware, firmware, software and/or any combination thereof. A more detailed illustration of the cardiac data collection module 2365 is provided in FIG. 24A and accompanying description below.

The cardiac data collection module 2365 is capable of collecting cardiac data comprising fiducial time markers of each of a plurality of candidate heart beats and providing the collected cardiac data to a heart beat/interval determination module 2375. Based upon the signals processed by the cardiac data collection module 2365, the heart beat/interval determination module 2375 may calculate an interbeat interval from a consecutive pair of the fiducial time markers and store such interbeat interval or forward it on for further processing/analysis. The heart beat/interval determination module 2375 may comprise software module(s) that are capable of performing various interface functions, filtering functions, etc., to calculate interbeat intervals. In another embodiment the heart beat/interval determination module 2375 may comprise hardware circuitry that is capable of performing these functions. In yet another embodiment, the heart beat/interval determination module 2375 may comprise hardware, firmware, software and/or any combination thereof. Further description of the heart beat/interval determination module 2375 is provided in FIG. 24B and accompanying description below.

The heart beat/interval determination module 2375 is capable of calculating an interbeat interval and providing the interbeat interval to the heart rate/heart rate variability (HRV)/complex module 2397. Based upon one or more interbeat intervals received from the heart beat/interval determination module 2375, and/or signals of sufficient sampling rate to provide information regarding the heart beat complex received from the cardiac data collection module 2365, the HR derivative/complex module 2397 determines at least one or more of an heart rate (such as from an interbeat interval determined from a consecutive pair of fiducial time markers), a heart rate variability (such as from two consecutive interbeat intervals determined from fiducial time markers), or at least a portion of a heart beat complex.

The HR derivative/complex module 2397 may comprise software module(s) that are capable of performing various interface functions, filtering functions, etc., to calculate the various values. In another embodiment the HR derivative/complex module 2397 may comprise hardware circuitry that is capable of performing these functions. In yet another embodiment, the HR derivative/complex module 2397 may comprise hardware, firmware, software and/or any combination thereof. Further description of the HR derivative/complex module 2397 is provided in FIG. 24E and accompanying description below.

The HR derivative/complex module 2397 is capable of forwarding the calculated information to template match module 2399. Based upon the information received by the template match module 2399, it performs any operations desired to indicate a state change. For example, the template match module 2399 may indicate a state change based on one or more of a heart rate shape matching an appropriate state change template, an HRV shape matching an appropriate state change template, a portion or more of a heart beat complex failing to match a reference heart beat complex template, or two or more of the foregoing. The template match module 2399 may comprise software module(s) that are capable of performing various interface functions, filtering functions, etc., to indicate a state change. In another embodiment the template match module 2399 may comprise hardware circuitry that is capable of performing these functions. In yet another embodiment, the template match module 2399 may comprise hardware, firmware, software and/or any combination thereof. Further description of the template match module 2399 is provided in FIG. 24F and accompanying description below.

In addition to components of the medical device 2300 described above, an implantable medical system may comprise a storage unit to store an indication of at least one of state change or an increased risk of a state change. The storage unit may be the memory 2317 of the medical device 2300, another storage unit of the medical device 2300, or an external database, such as the local database unit 2355 or a remote database unit 2350. The medical device 2300 may communicate the indication via the communications unit 2360. Alternatively or in addition to an external database, the medical device 2300 may be adapted to communicate the indication to at least one of a patient, a caregiver, or a healthcare provider.

In various embodiments, one or more of the units or modules described above may be located in a monitoring unit 2370 or a remote device 2392, with communications between that unit or module and a unit or module located in the medical device 2300 taking place via communication unit 2360. For example, in one embodiment, one or more of the cardiac data collection module 2365, the heart beat/interval determination module 2375, the HR derivative/complex module 2397, or the template match module 2399 may be external to the medical device 2300, e.g., in a monitoring unit 2370. Locating one or more of the cardiac data collection module 2365, the heart beat/interval determination module 2375, the HR derivative/complex module 2397, or the template match module 2399 outside the medical device 2300 may be advantageous if the calculation(s) is/are computationally intensive, in order to reduce energy expenditure and heat generation in the medical device 2300 or to expedite calculation.

The monitoring unit 2370 may be a device that is capable of transmitting and receiving data to and from the medical device 2300. In one embodiment, the monitoring unit 2370 is a computer system capable of executing a data-acquisition program. The monitoring unit 2370 may be controlled by a healthcare provider, such as a physician, at a base station in, for example, a doctor's office. In alternative embodiments, the monitoring unit 2370 may be controlled by a patient in a system providing less interactive communication with the medical device 2300 than another monitoring unit 2370 controlled by a healthcare provider. Whether controlled by the patient or by a healthcare provider, the monitoring unit 2370 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 2370 may download various parameters and program software into the medical device 2300 for programming the operation of the medical device, and may also receive and upload various status conditions and other data from the medical device 2300. Communications between the monitoring unit 2370 and the communication unit 2360 in the medical device 2300 may occur via a wireless or other type of communication, represented generally by line 2377 in FIG. 23. This may occur using, e.g., wand 2255 (FIG. 22) to communicate by RF energy with an implantable signal generator 2210. Alternatively, the wand may be omitted in some systems, e.g., systems in which the MD 2300 is non-implantable, or implantable systems in which monitoring unit 2370 and MD 2300 operate in the MICS bandwidths.

In one embodiment, the monitoring unit 2370 may comprise a local database unit 2355. Optionally or alternatively, the monitoring unit 2370 may also be coupled to a database unit 2350, which may be separate from monitoring unit 2370 (e.g., a centralized database wirelessly linked to a handheld monitoring unit 2370). The database unit 2350 and/or the local database unit 2355 are capable of storing various patient data. These data may comprise patient parameter data acquired from a patient's body, therapy parameter data, state change severity data, and/or therapeutic efficacy data.

The database unit 2350 and/or the local database unit 2355 may comprise data for a plurality of patients, and may be organized and stored in a variety of manners, such as in date format, severity of disease format, etc. The database unit 2350 and/or the local database unit 2355 may be relational databases in one embodiment. A physician may perform various patient management functions (e.g., programming parameters for a responsive therapy and/or setting thresholds for one or more detection parameters) using the monitoring unit 2370, which may include obtaining and/or analyzing data from the medical device 2300 and/or data from the database unit 2350 and/or the local database unit 2355. The database unit 2350 and/or the local database unit 2355 may store various patient data.

One or more of the blocks illustrated in the block diagram of the medical device 2300 in FIG. 23A or FIG. 23B, may comprise hardware units, software units, firmware units, or any combination thereof. Additionally, one or more blocks illustrated in FIG. 23A-B may be combined with other blocks, which may represent circuit hardware units, software algorithms, etc. Additionally, any number of the circuitry or software units associated with the various blocks illustrated in FIG. 23A-B may be combined into a programmable device, such as a field programmable gate array, an ASIC device, etc.

Figure 24A:
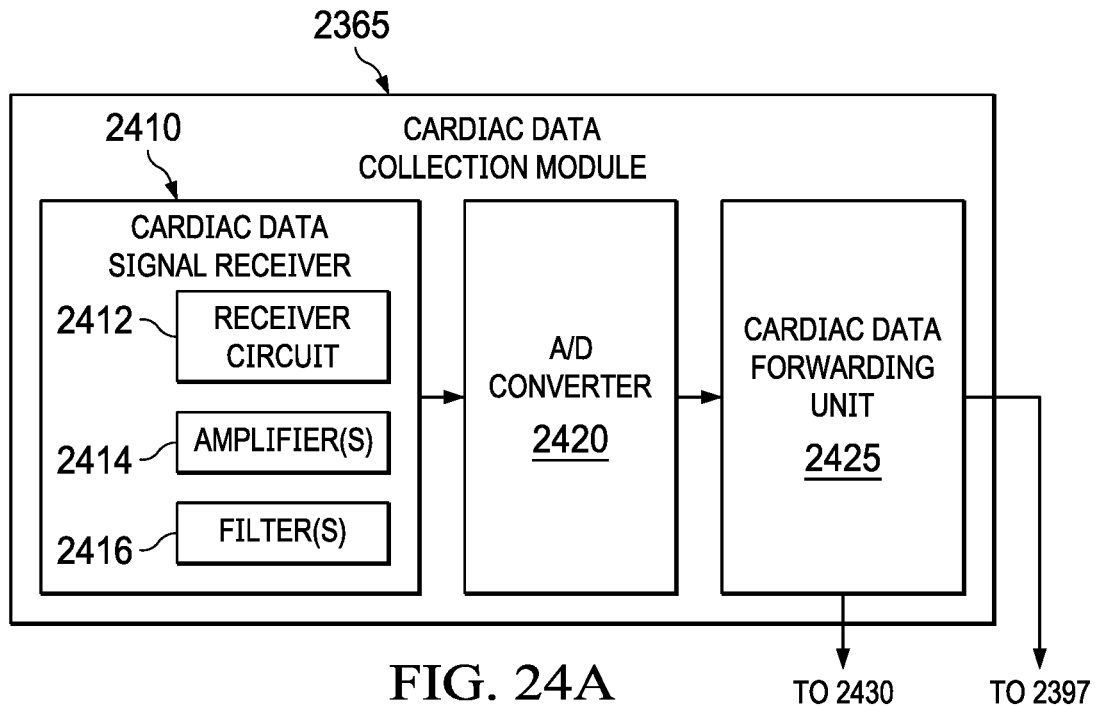
FIG. 24A is a stylized block diagram of a cardiac data collection module of a medical device, in accordance with one illustrative embodiment of the present disclosure.

Turning now to FIG. 24A, a more detailed stylized depiction of the cardiac data collection module 2365 of FIG. 23, in accordance with one illustrative embodiment of the present disclosure is depicted. In one embodiment, the cardiac data collection module 2365 comprises a cardiac data signal receiver 2410, an analog-to-digital converter (A/D Converter) 2420, and a cardiac data forwarding unit 2425. The cardiac data signal receiver 2410 is capable of receiving the signals from the sensor(s) 2312 via receiver circuit 2412. The signal that is received by the receiver circuit 2412 is processed and filtered to enable the data to be further analyzed and/or processed for determining cardiac data, such as that described above.

The cardiac data signal receiver 2410 may comprise amplifier(s) 2414 and filter(s) 2416. The amplifiers 2414 are capable of buffering and amplifying the input signals received by the receiver circuit 2412. In many cases, the heart beat signal may be attenuated and may be characterized by significantly low amplitude responses and signal noise. The amplifier(s) 2414 are capable of buffering (amplification by unity) and amplifying the signals for further processing. In one embodiment, the amplifier 2414 may comprise op amp circuit(s), digital amplifier(s), buffer amplifiers, and/or the like.

The cardiac data signal receiver 2410 may also comprise one or more filters 2416. The filters 2416 may comprise analog filter(s), digital filter(s), filters implemented by digital signal processing (DSP) means or methods, etc. The amplified and buffered signal may be filtered to remove various noise signals residing on the signal. The filter 2416, for example, is capable of filtering out various noise signals caused by external magnetic fields, electrical fields, noise resulting from physiological activity, etc. Signal noise due to breathing or other signals produced by the patient's body may be filtered.

The cardiac data signal receiver 2410 provides amplified, filtered signals to the A/D converter 2420. The A/D converter 2420 performs an analog-to-digital conversion for further processing. The A/D converter 2420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a cardiac data forwarding unit 2425. In an alternative embodiment, the A/D conversion may be performed prior to filtering or signal processing of the heart beat signal. The converted digital signal is then provided to a cardiac data forwarding unit 2425.

The cardiac data forwarding unit 2425 is capable of organizing, correlating, stacking, and otherwise processing the digitized, buffered, and filtered cardiac data and forwarding it to the heart beat/interval determination module 2375, and/or directly to the HR derivative/complex module 2397.

Figure 24B:
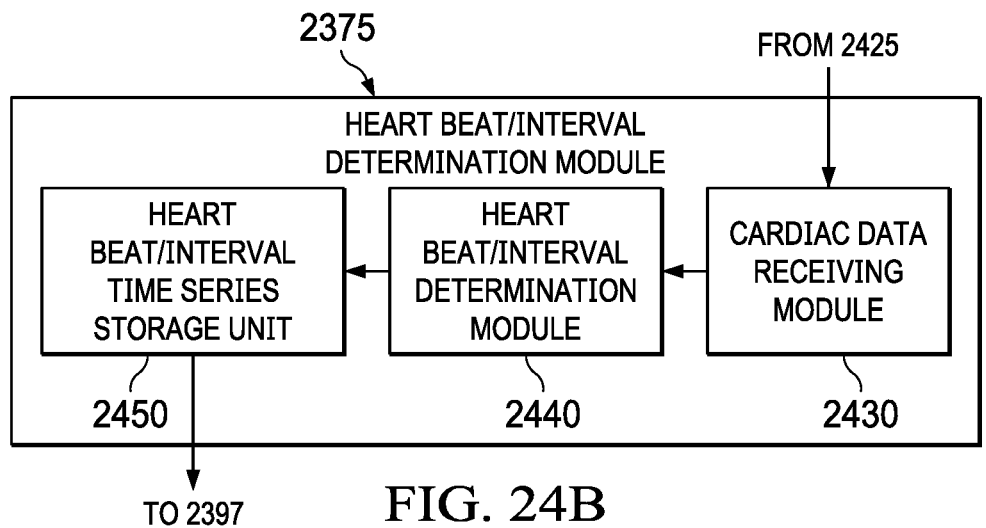
FIG. 24B is a stylized block diagram of a heart beat/interval determination module of a medical device, in accordance with one illustrative embodiment of the present disclosure.

Turning now to FIG. 24B, a more detailed stylized depiction of the heart beat/interval determination module 2375 of FIG. 23, in accordance with one illustrative embodiment of the present disclosure, is depicted. The heart beat/interval determination module 2375 may comprise a cardiac data receiving module 2430, for receiving a time stamp sequence of candidate heart beats, a heart beat/interval determination module 2440, and a heart beat/interval time series storage unit 2450. The heart beat/interval determination module 2375 may determine interbeat intervals for adjacent candidate heart beats as they appear in the time series of signals via the cardiac data receiving module 2430. For example, cardiac data receiving module 2430 may characterize certain data points in the time series of signals as being fiducial time markers corresponding to the start, the peak, or the end of an R-wave of a patient's cardiac cycle.

Once fiducial time markers are determined from the time series of signals, the heart beat/interval determination module 2440 may determine the interval between consecutive beats ("interbeat interval") and forward this information to heart beat/interval time series storage 2450, which may store one or both of a time stamp series associated with fiducial markers indicating of an individual heart beat and a time stamp series of adjacent interbeat intervals. In some embodiments, the heart beat/interval determination module 2440 may calculate a heart rate, heart rate variability (HRV), or at least a portion of a heart beat complex. In other embodiments, heart beat/interval determination module 2440 may calculate a heart rate, heart rate variability (HRV), or both.

Figure 24C:
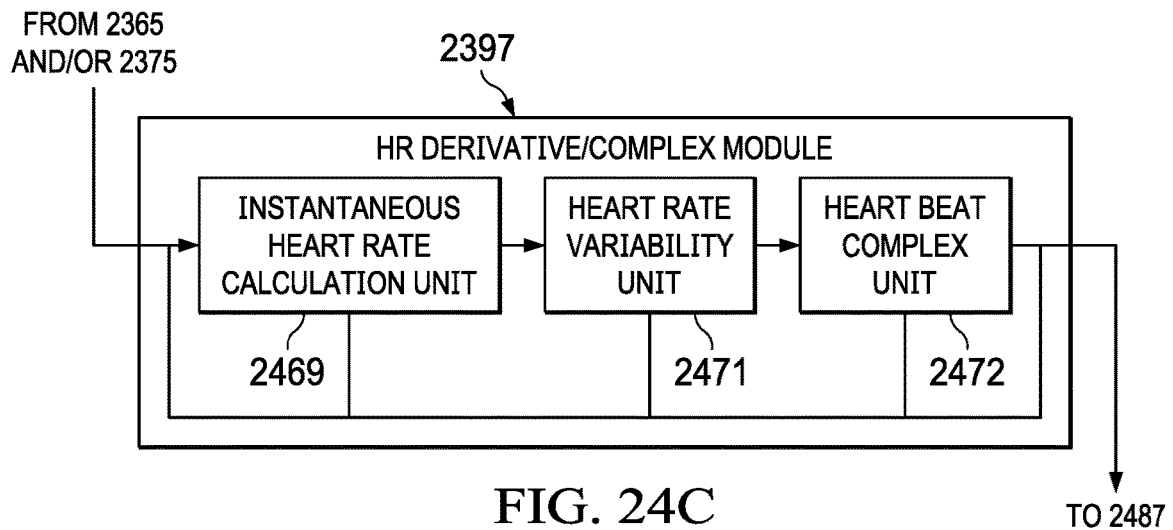
FIG. 24C is a stylized block diagram of a HR derivative/complex module of a medical device, in accordance with one illustrative embodiment of the present disclosure.

Turning now to FIG. 24C, a more detailed stylized depiction of the HR derivative/complex module 2397 of FIG. 23, in accordance with one illustrative embodiment of the present disclosure, is depicted. In one embodiment, the HR derivative/complex module 2397 may receive various cardiac data indicative from the cardiac data collection module 2365 or the heart beat/interval determination module 2375. In the embodiment depicted in FIG. 24C, the HR derivative/complex module 2397 comprises units that perform various calculations, for example, a heart rate calculation unit 2469 may determine a heart rate from some or all interbeat intervals and/or pairs of heart beats collected and/or identified by modules 2365 or 2375. Certain embodiments of the disclosure may also include a heart rate variability unit 2471 which determines an HRV value from some or all interbeat intervals and/or pairs of heart beats collected and/or identified by modules 2365 or 2375, and/or a heart beat complex unit 2472 which analyzes one or more portions of a heart beat complex, e.g., relative R-wave and P-wave amplitudes, P-wave to R-wave temporal separations, or the like. Of course, one or more of units 2469, 2471, and 2472 may be omitted, if desired.

The HR derivative/complex module 2397 need not perform all steps 2469-2472.

Any steps the HR derivative/complex module 2397 performs may be in any order, not necessarily that shown.

Although the heart rate calculation unit 2469, the heart rate variability unit 2471, and the heart beat complex unit 2472 are shown in FIG. 24C as components of HR derivative/complex module 2397, in various other embodiments, one or more of these units can be included in other modules.

Figure 24D:
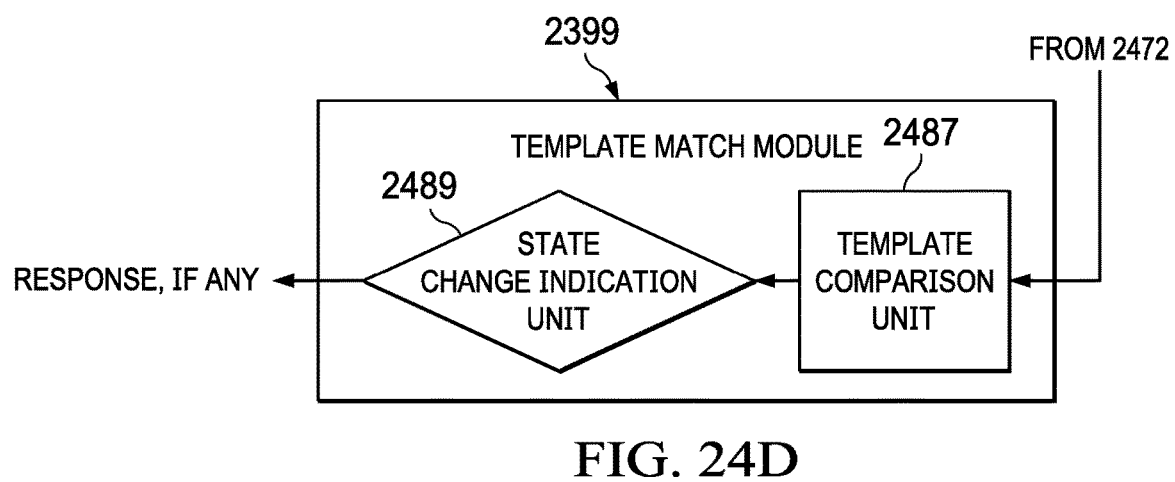
FIG. 24D is a stylized block diagram of a template match module of a medical device, in accordance with one illustrative embodiment of the present disclosure.

Turning now to FIG. 24D, a more detailed stylized depiction of the template match module 2399 of FIG. 23, in accordance with one illustrative embodiment of the present disclosure, is depicted. The template match module 2399 may receive various data from the HR derivative/complex module 2397, including, for example, one or more a heart rate shape characteristics, one or more HRV shape characteristics, information regarding one or more portions of a heart beat complex, etc. Based upon data from the HR derivative/complex module 2397, the template match module 2399 is capable of indicating a state change, such as described above.

In the exemplary depiction shown in FIG. 24D, data received from the HR derivative/complex module 2397 is forwarded to a template comparison unit 2487, which determines whether one or more of the heart rate shape, HRV shape, or portion of the heart beat complex matches a relevant template. The determination of a match can be performed by known mathematical techniques, such as matched filtering, or the like. A signal indicative of the occurrence of a state change is provided by state change indication unit 2489 if the template comparison is indicative of a state change, such as a seizure.

If a state change is identified by template match module 2399, in one embodiment, a response may be implemented, such as those described by U.S. patent application Ser. No. 12/770,562, filed Apr. 29, 2010; Ser. No. 12/771,727, filed Apr. 30, 2010; and Ser. No. 12/771,783, filed Apr. 30, 2010.

Figure 25:
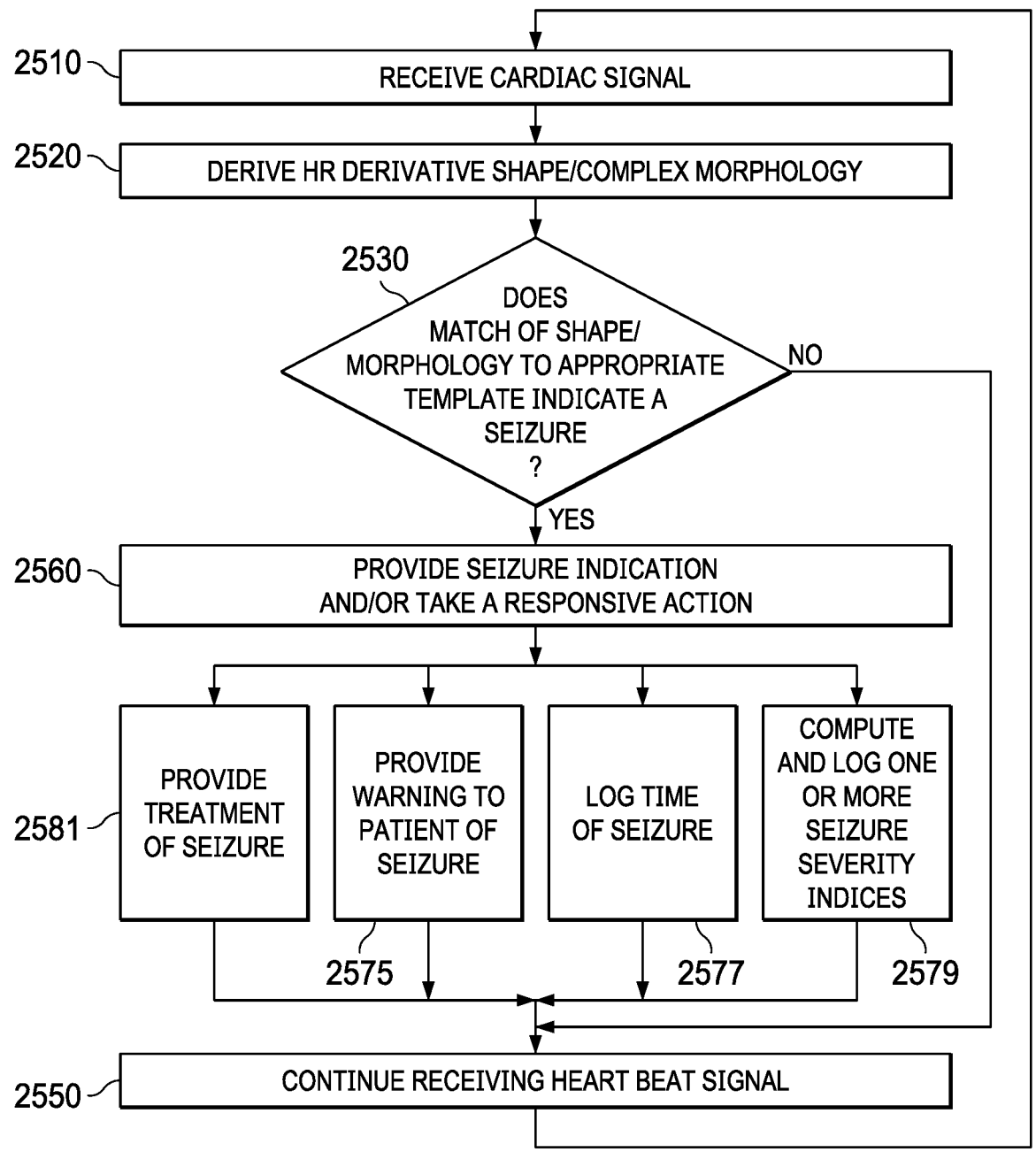
FIG. 25 illustrates a flowchart depiction of a method for detecting a state change and taking one or more responsive actions, in accordance with an illustrative embodiment of the present disclosure.

Turning now to FIG. 25, a stylized flowchart depiction of detecting one particular type of state change, namely, a seizure, in accordance with one illustrative embodiment of the present disclosure, is provided. The medical device 2300 receives a cardiac signal (block 2510). In specific embodiments, the cardiac data collection module 2365 (FIGS. 23 and 24A) of the medical device 2300 receives the cardiac signal. After performing buffering, amplification, filtering, and A/D conversion of the cardiac signal, the heart beat/interval determination module 2375 and/or HR derivative/complex module 2397 processes the heart beat signal to derive HR derivative shapes or heart beat complex morphology (block 2520). From the derived shapes or characteristics, it is decided from one or more template matching operations if a state change is indicated (block 2530). This decision may be performed by template match module 2399.

Based upon the decision (block 2530), if no state change is indicated, the medical device 2300 continues to receive the heart beat signal (block 2550, returning flow to block 2510).

However, if a state change is indicated in block 2530, the medical device 2300 or an external unit 2370 may provide an indication of the state change occurrence and/or take a responsive action (block 2560), such as providing a warning to the patient or his or her caregivers, physician, etc. (block 2575); logging a time of state change (block 2577); computing and optionally logging one or more state change severity indices (block 2579); and/or providing treatment of the state change (block 2581). More details on logging, warning, computing seizure severity, and providing treatment are provided in U.S. patent application Ser. No. 12/770,562, filed Apr. 29, 2010; Ser. No. 12/771,727, filed Apr. 30, 2010; Ser. No. 12/771,783, filed Apr. 30, 2010; and Ser. No. 12/756,065, filed Apr. 7, 2010.

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

In various embodiments, the present disclosure relates to the subject matter of the following numbered paragraphs:

34. A method for identifying a state change template from cardiac data, comprising:
   obtaining a time series of cardiac data from a patient during a first time window;
   determining a time of occurrence of at least one state change suffered by said patient during said first time window; and
   either
   (i) determining at least one state change template in the time series of cardiac data within the first time window and timewise correlated with the at least one state change, wherein the at least one state change template comprises at least one characteristic selected from a number of phases relative to a reference heart rate parameter, a number of extrema, area under the curve of at least one phase, a number of directions of change, a number of positive phases relative to said reference heart rate parameter, or a number of negative phases relative to said reference heart rate parameter, or
   (ii) determining at least one reference heart beat complex template in said time series of cardiac data within said first time window and not timewise correlated with said at least one state change.

35. The method of number 34, wherein said cardiac data comprises heart rate data, heart rate variability data, or heart rate volatility data.

36. The method of number 34, wherein said cardiac data comprises at least a portion of each of a plurality of heart beat complexes.

37. The method of number 34, wherein said at least one characteristic comprises at least one of the amplitude of at least one phase, the duration of at least one phase, the valence (positive or negative) of at least one phase, the area under the curve of at least one phase, at least one slope of at least one phase, the arc length of at least one phase, the number of extrema in at least one phase, and the sharpness of the extrema of at least one phase.

38. A method for obtaining a state change template indicative of an occurrence of a state change of interest, comprising:
   obtaining a first time series of cardiac data from a patient, the first time series not associated with said state change of interest;
   determining at least one reference heart rate parameter from said first time series of cardiac data;

obtaining a second time series of cardiac data from said patient, the second time series being associated with said state change of interest;

determining at least one property of said heart rate derivative, said property comprising at least one of a number of phases relative to said reference heart rate parameter, the perimeter of at least one phase, a number of extrema of said heart rate derivative, the sharpness of said extrema, a number of directions of change of said heart rate derivative, an area under the curve of at least one phase, a number of positive phases, or a number of negative phases; and determining that the at least one property of said heart rate derivative of the state of interest is different from the same at least one property of the heart rate derivative not associated with the state of interest obtaining a state change template associated with said state change of interest and comprising said at least one property, from said heart rate derivative and using it as a matched filter to detect said state change.

39. The method of number 38, wherein the at least one property of said pattern comprises a shape of said pattern, a time of occurrence of said pattern, a time elapsed between occurrences of said pattern, and an association of said pattern with a state change of a body organ.

40. The method of number 39, wherein said at least one property of said pattern is an association of said pattern with a state change of the brain.

41. The method of number 40, wherein said state change of the brain is a epileptic seizure.

42. The method of number 38, wherein said heart rate derivative is heart rate.

43. The method of number 38, wherein said heart rate derivative is heart rate variability or heart rate volatility.

44. A method for indicating an occurrence of a state change, comprising:

providing a first template comprising at least one of a microscopic state change template, a mesoscopic state change template, and a macroscopic state change template;

obtaining a time series of cardiac data from a patient;

determining a first cardiac data derivative shape from said time series of cardiac data; and, indicating an occurrence of a state change based upon a determination that said first cardiac data derivative shape matches said first template.

45. The method of number 44, further comprising:

providing a second template comprising at least one of said microscopic state change template, said mesoscopic state change template, and said macroscopic state change template, wherein said second template is not based upon a state change template included in said first template;

determining a second cardiac data derivative shape from said time series of cardiac data;

and wherein said indicating is based upon a determination that said first cardiac data derivative shape matches said first template and said second cardiac data derivative shape matches said second template.

46. The method of number 44, wherein said determination comprises using a matched filter on a moving window of said first cardiac data derivative, calculating a time series of outputs of said matched filter, and declaring said match if said time series of outputs is substantially equal to a time series of expected output values.

101. A method for indicating an occurrence of a state change, comprising:

obtaining a time series of cardiac data from a patient;

selecting at least one parameter from said cardiac data time series;

determining the magnitude, duration, direction and rate of change of said parameter during a reference state wherein said parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

indicating the occurrence of a state change when at least one of said values is greater or lower than at least one reference state parameter value, e.g., for a certain time period.

102. The method of number 101 wherein the parameters' values are treated as phases and extrema endowed with shape, curvature, arc length and inflection points;

indicating the occurrence of a state change when at least one of the parameters' values is greater or lower than at least one reference state parameter values, e.g., for a certain time period.

103. The method of number 101 wherein the cardiac data parameter's value's temporal scale is macroscopic.

104. The method of number 101 wherein the cardiac data parameter's value's temporal scale is mesoscopic.

105. The method of number 101 wherein the cardiac data parameter's value's temporal scale is microscopic.

106. A method for indicating an occurrence of a state change, comprising:

obtaining a time series of cardiac data from a patient during a reference state;

selecting at least one parameter from said cardiac data during said reference state wherein said reference parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

constructing a reference template using said at least one reference parameter value and using said template as a reference matched filter;

indicating an occurrence of a state change based upon a determination that the output of said at least one reference matched filter reaches a value outside the range of values characteristic of the reference state.

107. The method of number 106 wherein the reference matched filter's scale is macroscopic.

108. The method of number 106 wherein the reference matched filter's scale is mesoscopic.

109. The method of number 106 wherein the reference matched filter's scale is microscopic.

110. A method for indicating an occurrence of a state change, comprising:

obtaining a time series of cardiac data from a patient during a non-reference state;

selecting at least one parameter from said cardiac data during said non-reference state wherein said non-reference parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

constructing a non-reference template using said at least one non-reference parameter value and using said non-reference template as a non-reference matched filter;
indicating an occurrence of a state change based upon a determination that the output of said at least one non-reference matched filter reaches a value characteristic of the non-reference state values.

111. The method of number 110, wherein the non-reference matched filter's scale is macroscopic.

112. The method of number 110, wherein the non-reference matched filter's scale is mesoscopic.

113. The method of number 110, wherein the non-reference matched filter's scale is microscopic.

114. A method for indicating an occurrence of a state change, comprising:
obtaining a time series of cardiac data from a patient;
selecting at least one reference parameter and at least one non-reference parameter from said cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;
constructing a reference template using said at least one reference parameter value and using said reference template as a reference matched filter;
constructing a non-reference template using said at least one non-reference parameter value and using said non-reference template as a non-reference matched filter;
indicating an occurrence of a state change based upon a determination that the output of said at least one reference matched filter reaches a value outside the values characteristic of the reference state values and the output of said at least one non-reference matched filter reaches a value characteristic of the non-reference state values.

115. The method of number 114, wherein the scales of the reference and of the non-reference matched filters are macroscopic.

116. The method of number 114, wherein the scales of the reference and of the non-reference matched filters are mesoscopic.

117. The method of number 114, wherein the scales of the reference and of the non-reference matched filters are microscopic.

118. A method for obtaining a state change template indicative of an occurrence of a state change of interest, comprising:
obtaining a first time series of cardiac data from a patient, the first time series not associated with said state change of interest;
determining at least one parameter from said first time series of cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;
obtaining a second time series of cardiac data from said patient, the second time series being associated with said state change of interest;
determining at least one parameter from said second time series of cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;
determining that the at least one parameter from said second time series of cardiac data associated with a state change of interest is different from the same at least one parameter of the first time series of cardiac data not associated with a state change of interest;
obtaining a state change template associated with said state change of interest and comprising said at least one property;
using said state change template as a matched filter to detect similar state changes.

119. The method of number 118, wherein the scale of said template and matched filter associated with a state change of interest is macroscopic.

120. The method of number 118, wherein the scale of said template and matched filter associated with a state change of interest is mesoscopic.

121. The method of number 118, wherein the scale of said template and matched filter associated with a state change of interest is microscopic.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed:

1. A method of treating a medical condition in a patient using an implantable medical device, the implantable medical device including a first electrode configured to be coupled to a first cranial nerve structure and a second electrode configured to be coupled to a second cranial nerve structure, the method comprising:
obtaining data relating to at least a portion of a heart beat complex from a patient;
comparing the at least the portion of the heart beat complex with a corresponding portion of a first reference heart beat complex template of the patient;
indicating an occurrence of a state change based upon a determination that the heart beat complex fails to match the first reference heart beat complex template;
providing a first electrical signal to the first cranial nerve structure of the patient, the first electrical signal is configured to induce action potentials in the first cranial nerve structure and a charge accumulates based on the first electrical signal; and
providing a second electrical signal to the second cranial nerve structure, the second electrical signal is configured to induce action potentials in the second cranial nerve structure where at least a portion of the second electrical signal comprises the accumulated charge from the first electrical signal.

2. The method of claim 1, further comprising verifying the occurrence of a seizure based upon the comparison.

3. The method of claim 2, wherein the verification of the occurrence of the seizure is based on a determination that the portion of the heart beat complex shape failed to match the corresponding portion of the reference heart beat complex shape template.

4. The method of claim 3, wherein the identifying further includes: determining a second reference heart rate derived shape from the time series of cardiac data where the second reference heart rate derived shape comprises a second characteristic selected from a second number of phases relative to the second reference heart rate derived shape; a second number of positive phases relative to the second reference heart rate derived shape; a second number of negative phases relative to the second reference heart rate derived shape; a second number of extrema of the second heart rate derivative; a second area under a second curve of a second phase; or a second number of directions of change of the second heart rate derivative.

5. The method of claim 4, wherein the identifying the occurrence of the seizure is further based upon a determination that the second reference heart rate derived shape matches a second seizure template in the second characteristic.

6. The method of claim 3, wherein the heart rate derivative is at least one of a heart rate and a heart rate variability.

7. The method of claim 1, wherein the identifying further includes: obtaining a time series of cardiac data from the patient; determining a reference heart rate derived shape from the time series of cardiac data where the reference heart rate derived shape comprises at least one characteristic selected from: a number of phases relative to the reference heart rate parameter; a number of extrema of a heart rate derivative; a number of directions of change of the heart rate derivative; an area under a first curve of a first phase; a number of positive phases; or a number of negative phases.

8. The method of claim 1, wherein the portion of the heart beat complex shape comprises at least one of: an amplitude of a P wave; a polarity of the P wave; an amplitude of an R wave; a polarity of a Q wave; a polarity of the R wave; an amplitude of an S wave; a polarity of the S wave; an amplitude of a T wave; a polarity of the T wave; an area under a curve of the P wave; an area under a curve of the Q wave; an area under a curve of the R wave; an area under a curve of the S wave; an area under a curve of the T wave; a width of the P wave; a width of the Q wave; a width of the R wave; a width of the S wave; a width of the T wave; a morphology of the P wave; a morphology of the Q wave; a morphology of the R wave; a morphology of the T wave; a magnitude of a change in a distance from the P wave to the Q wave; a magnitude of a change in a distance from the P wave to the R wave; a magnitude of a change in a distance from the Q wave to the R wave; a magnitude of a change in a distance from the R wave to the S wave; a magnitude of a change in a distance from the R wave to the T wave; a magnitude of a change in a distance from the S wave to the T wave; a magnitude of an S-T segment elevation; a magnitude of an S-T segment depression; a magnitude of a Q-T segment elevation; a magnitude of a Q-T segment depression; a P-R interval; an R-S interval; an S-T interval; an R-T interval; and a Q-T interval.

9. The method of claim 1, wherein the comparing further comprises comparing the portion of the heart beat complex shape with a corresponding portion of a second reference heart beat complex shape template of the patient, and wherein the verification is based upon a determination that the heart beat complex shape fails to match at least one of the reference heart beat complex shape template and the second reference heart beat complex shape template.

10. The method of claim 1, wherein the identifying the occurrence of the seizure is based upon a determination that a heart rate derived shape matches a seizure template in at least one characteristic.

11. The method of claim 1, wherein the comparing further comprises obtaining a corresponding portion of a second reference heart beat complex shape template of the patient and comparing the portion of the reference heart beat complex shape with the corresponding portion of a second reference heart beat complex shape template of the patient, and wherein the verification is based upon a determination that the heart beat complex shape fails to match both the reference heart beat complex shape template and the second reference heart beat complex shape template.

12. The method of claim 1, further comprising obtaining a second reference heart beat complex shape template and verifying an occurrence of the seizure is based upon both the determination that the heart beat complex shape fails to match the reference heart beat complex shape template and a second determination that the heart beat complex shape fails to match the second reference heart beat complex shape template.

13. The method of claim 12, wherein the method further comprises taking an action in response to the verification, wherein the action is at least one of: providing a warning of the seizure; logging a time of the seizure; computing one or more seizure indices; logging one or more computed seizure indices; and providing at least one treatment of the seizure.

14. The method of claim 12, wherein the obtaining further comprises obtaining data relating to at least a portion of a plurality of heart beat complex shapes and the verification is based upon a determination that at least one heart beat complex shape of the plurality of heart beat complex shapes fails to match the reference heart beat complex shape template.

* * * * *